(12) United States Patent
Morris et al.

(10) Patent No.: US 7,922,744 B2
(45) Date of Patent: Apr. 12, 2011

(54) COMPACT SUTURE PUNCH WITH MALLEABLE NEEDLE

(76) Inventors: John K. Morris, Ann Arbor, MI (US);
Robert A. Van Wyk, Largo, FL (US)

( * ) Notice: Subject to any disclaimer, the term of this patent is extended or adjusted under 35 U.S.C. 154(b) by 971 days.

(21) Appl. No.: 11/515,601

(22) Filed: Nov. 27, 2006

(65) Prior Publication Data

US 2007/0060953 A1    Mar. 15, 2007

Related U.S. Application Data

(63) Continuation of application No. 10/815,338, filed on Apr. 1, 2004, now abandoned, which is a continuation-in-part of application No. 10/165,468, filed on Jun. 7, 2002, now Pat. No. 7,112,208.

(60) Provisional application No. 60/310,220, filed on Aug. 6, 2001.

(51) Int. Cl.
*A61B 17/04* (2006.01)

(52) U.S. Cl. ........................................................ 606/222

(58) Field of Classification Search .......... 606/139–148, 606/222–233
See application file for complete search history.

(56) References Cited

U.S. PATENT DOCUMENTS

| | | | |
|---|---|---|---|
| 1,037,864 A | 9/1912 | Carlson et al. | |
| 2,023,807 A * | 12/1935 | Gruss et al. | ................ 606/225 |
| 3,349,772 A | 10/1967 | Rygg | |
| 3,470,875 A | 10/1969 | Johnson | |
| 3,946,740 A | 3/1976 | Bassett | |
| 4,164,225 A | 8/1979 | Johnson et al. | |
| 4,643,178 A | 2/1987 | Nastari et al. | |
| 4,660,559 A * | 4/1987 | McGregor et al. | ............ 606/226 |
| 4,836,205 A | 6/1989 | Barrett | |
| 4,890,615 A | 1/1990 | Caspari et al. | |
| 4,923,461 A | 5/1990 | Caspari et al. | |
| 4,932,961 A | 6/1990 | Wong et al. | |
| 4,957,498 A | 9/1990 | Caspari et al. | |
| 5,002,563 A | 3/1991 | Pyka et al. | |
| 5,013,292 A | 5/1991 | Lemay | |
| 5,037,433 A | 8/1991 | Wilk et al. | |
| 5,100,421 A | 3/1992 | Christoudias | |
| 5,181,919 A | 1/1993 | Bergman et al. | |
| 5,219,358 A | 6/1993 | Bendel et al. | |
| 5,234,443 A | 8/1993 | Phan et al. | |

(Continued)

FOREIGN PATENT DOCUMENTS

EP     0792621 A1     9/1997

(Continued)

*Primary Examiner* — Kevin T Truong
(74) *Attorney, Agent, or Firm* — Chalin A. Smith; Smith Patent Consulting, LLC

(57) ABSTRACT

A suture punch system that is capable of directly passing braided suture through tissue in a simple, one-step process. The system includes three principle components: a malleable needle capable of delivering the suture to the tissue, a hand-held instrument for grasping tissue and controlling needle placement, and a force-supplying mechanism to supply the force required for needle placement. Needle deformation begins at the tip of the instrument, which beneficially includes a curved segment. As the distal tip of the needle pierces the tissue, it continues its radial path through the tissue. When the proximal end of the needle exits from the instrument, the needle may be radial in shape and traverses an essentially radial path through the tissue. Once the needle has passed entirely through the tissue, it may be retrieved using the jaws of the punch or another instrument.

13 Claims, 50 Drawing Sheets

U.S. PATENT DOCUMENTS

| | | | |
|---|---|---|---|
| 5,250,055 A | 10/1993 | Moore et al. | |
| 5,254,126 A | 10/1993 | Filipi et al. | |
| 5,257,637 A | 11/1993 | El Gazayerli | |
| 5,261,917 A | 11/1993 | Hasson et al. | |
| 5,292,327 A | 3/1994 | Dodd et al. | |
| 5,318,577 A | 6/1994 | Li | |
| 5,387,221 A | 2/1995 | Bisgaard | |
| 5,389,103 A | 2/1995 | Melzer et al. | |
| 5,397,325 A | 3/1995 | Della Badia et al. | |
| 5,423,837 A | 6/1995 | Mericle et al. | |
| 5,431,678 A | 7/1995 | Rogers | |
| 5,454,823 A | 10/1995 | Richardson et al. | |
| 5,496,335 A | 3/1996 | Thomason et al. | |
| 5,522,820 A | 6/1996 | Caspari et al. | |
| 5,527,322 A | 6/1996 | Klein et al. | |
| 5,571,090 A | 11/1996 | Sherts | |
| 5,578,044 A * | 11/1996 | Gordon et al. | 606/144 |
| 5,607,435 A | 3/1997 | Schdeva et al. | |
| 5,643,292 A | 7/1997 | Hart | |
| 5,665,096 A | 9/1997 | Yoon | |
| 5,690,653 A | 11/1997 | Richardson et al. | |
| 5,728,112 A | 3/1998 | Yoon | |
| 5,730,747 A | 3/1998 | Ek et al. | |
| 5,749,879 A * | 5/1998 | Middleman et al. | 606/139 |
| 5,755,728 A | 5/1998 | Maki | |
| 5,776,152 A | 7/1998 | Sekons | |
| 5,797,927 A | 8/1998 | Yoon | |
| 5,817,107 A | 10/1998 | Schaller | |
| 5,843,099 A | 12/1998 | Nichols et al. | |
| 5,897,572 A * | 4/1999 | Schulsinger et al. | 606/224 |
| 5,908,428 A | 6/1999 | Scirica et al. | |
| 5,925,064 A | 7/1999 | Meyers et al. | |
| 5,928,267 A | 7/1999 | Bonutti et al. | |
| 5,928,268 A * | 7/1999 | Butwell et al. | 606/222 |
| 5,931,844 A | 8/1999 | Thompson et al. | |
| 5,935,149 A | 8/1999 | Ek | |
| 5,947,982 A | 9/1999 | Duran | |
| 5,954,732 A | 9/1999 | Hart et al. | |
| 5,964,773 A | 10/1999 | Greenstein | |
| 5,980,538 A | 11/1999 | Fuchs et al. | |
| 6,024,747 A | 2/2000 | Kontos | |
| 6,051,006 A | 4/2000 | Shulzas et al. | |
| 6,059,800 A | 5/2000 | Hart et al. | |
| 6,099,538 A | 8/2000 | Moses et al. | |
| 6,197,035 B1 | 3/2001 | Loubens et al. | |
| 6,200,329 B1 | 3/2001 | Fung et al. | |
| 6,332,889 B1 | 12/2001 | Sancoff et al. | |
| 6,517,552 B1 | 2/2003 | Nord et al. | |
| 6,595,911 B2 | 7/2003 | Lovuolo | |
| 6,599,298 B1 | 7/2003 | Forster et al. | |
| 6,623,492 B1 | 9/2003 | Berube et al. | |
| 6,638,283 B2 | 10/2003 | Thal | |
| 6,679,895 B1 | 1/2004 | Sancoff et al. | |
| 6,723,107 B1 | 4/2004 | Skiba et al. | |
| 6,770,084 B1 | 8/2004 | Bain et al. | |
| 2002/0103493 A1 | 8/2002 | Thal | |
| 2002/0128666 A1 | 9/2002 | Sancoff et al. | |
| 2002/0138084 A1 | 9/2002 | Weber | |
| 2003/0065337 A1 | 4/2003 | Topper et al. | |
| 2003/0078600 A1 | 4/2003 | O'Quinn et al. | |
| 2003/0083695 A1 | 5/2003 | Morris et al. | |
| 2003/0105474 A1 | 6/2003 | Bonutti | |
| 2003/0144674 A1* | 7/2003 | Loubens et al. | 606/148 |
| 2003/0176874 A1 | 9/2003 | Sauer | |
| 2003/0216756 A1 | 11/2003 | Klein et al. | |
| 2003/0220658 A1 | 11/2003 | Hatch et al. | |
| 2003/0233108 A1 | 12/2003 | Gellman et al. | |
| 2004/0193185 A1 | 9/2004 | McBrayer | |
| 2004/0199184 A1 | 10/2004 | Topper et al. | |
| 2004/0249394 A1 | 12/2004 | Morris et al. | |
| 2004/0260314 A1 | 12/2004 | Lizardi et al. | |

FOREIGN PATENT DOCUMENTS

| | | |
|---|---|---|
| EP | 1159920 A2 | 12/2001 |
| GB | 2260704 A | 4/1993 |
| GB | 2398012 A | 8/2004 |
| JP | 06-063052 | 3/1994 |
| JP | 11-216145 | 8/1999 |
| WO | WO 95/13021 A1 | 5/1995 |
| WO | WO 96/09796 | 4/1996 |
| WO | WO 99/47050 | 9/1999 |
| WO | WO 2004/071306 | 8/2004 |

* cited by examiner

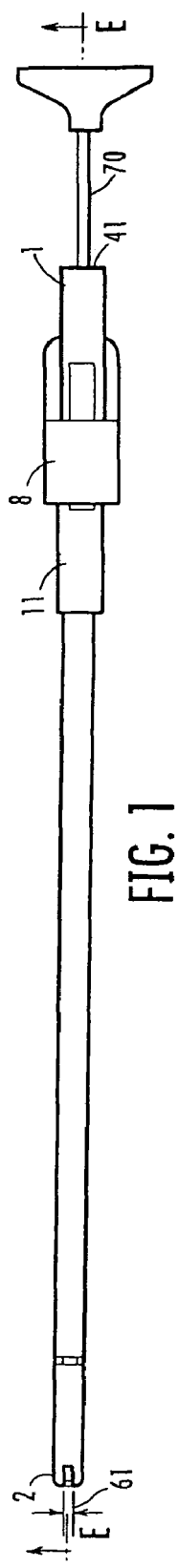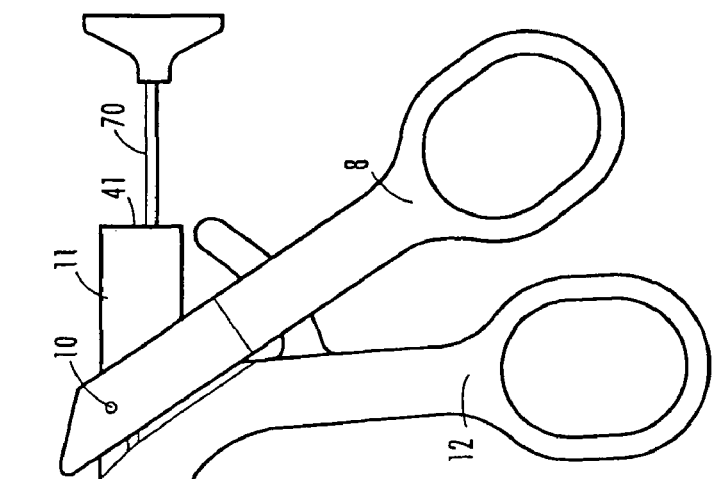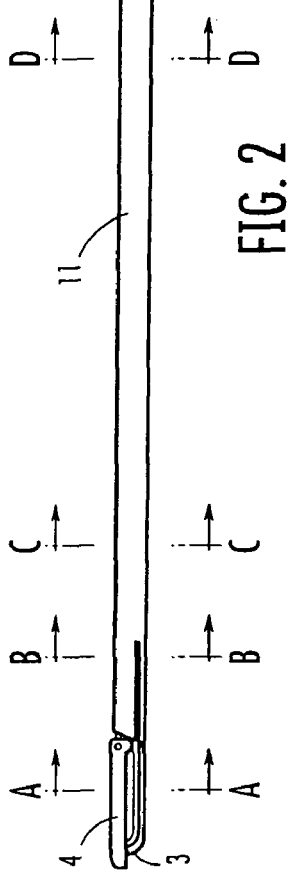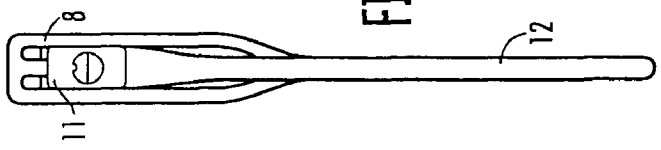
FIG. 1
FIG. 2
FIG. 3

SEC A-A

SEC B-B

SEC C-C

SEC D-D

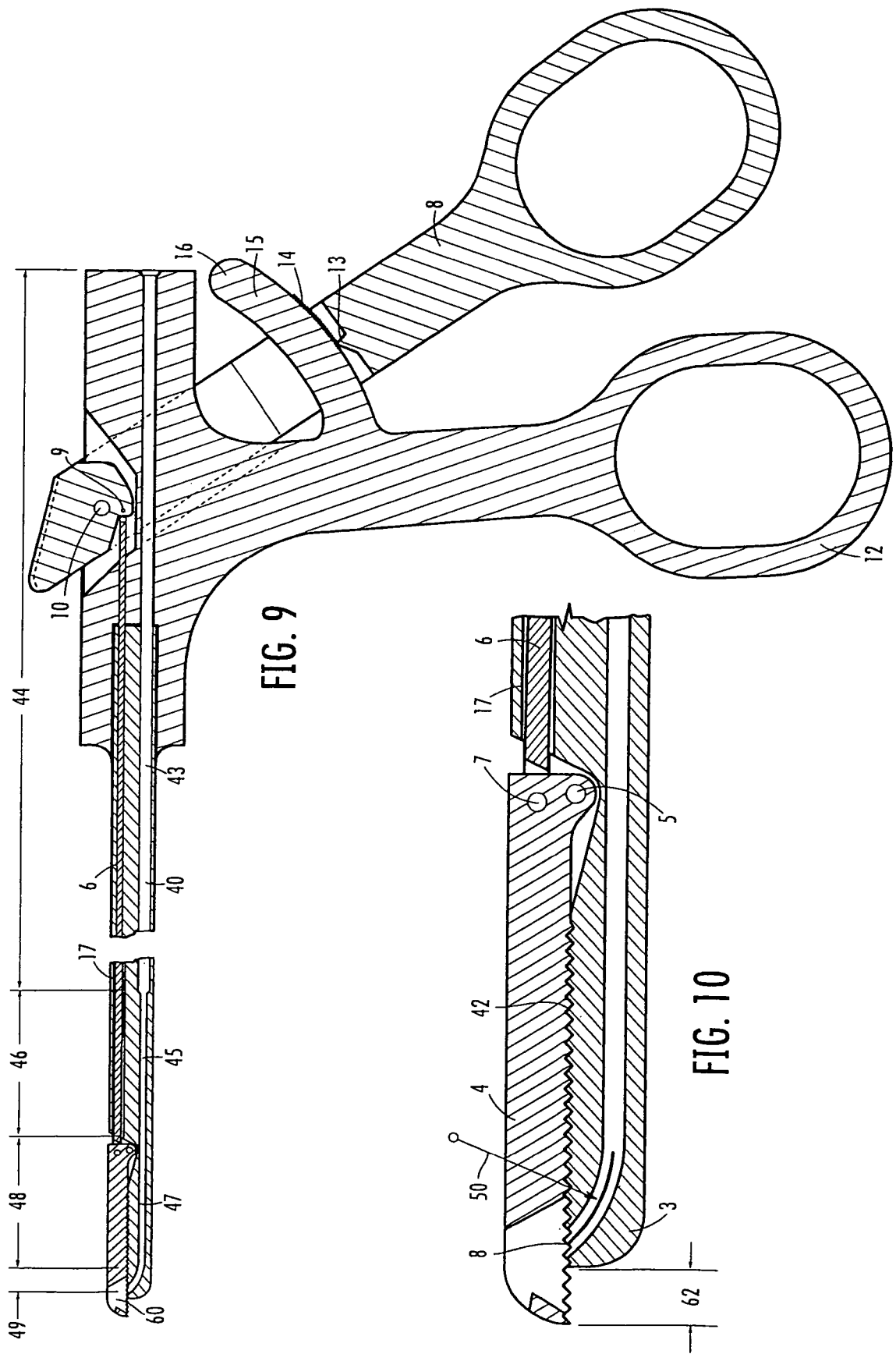

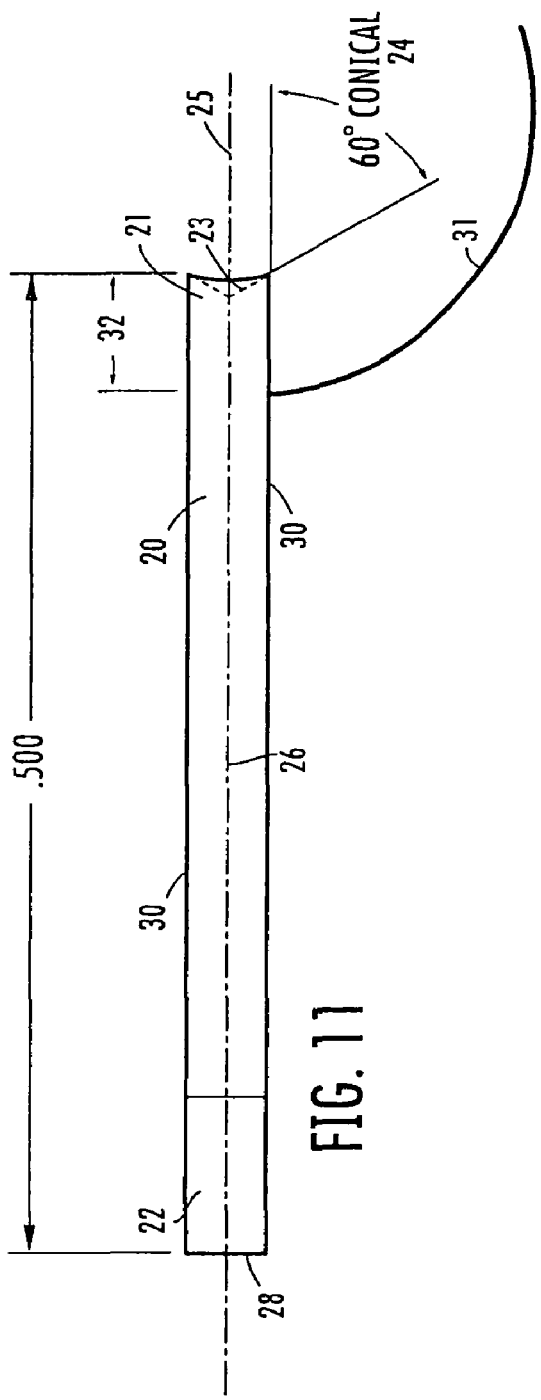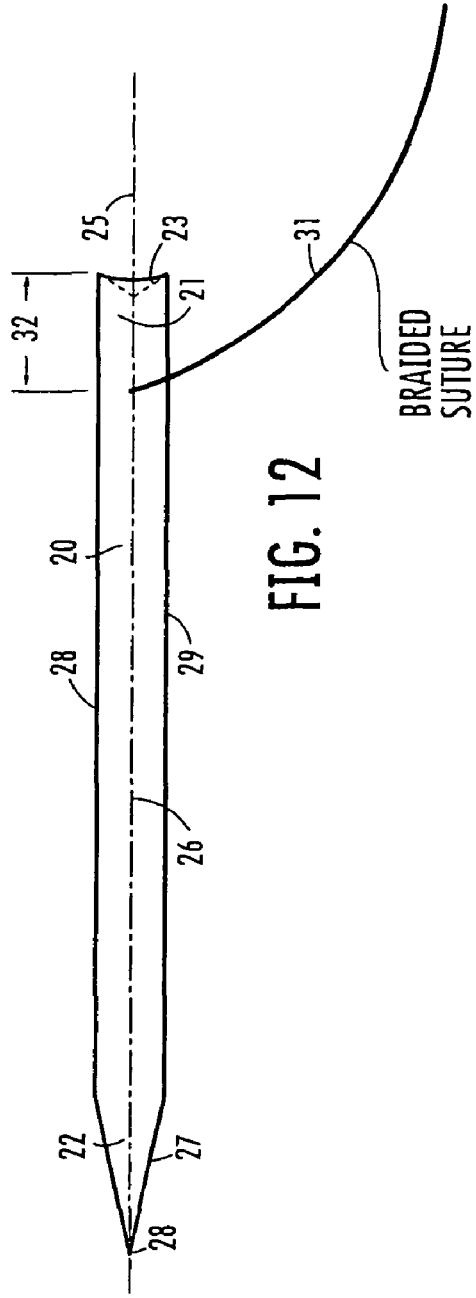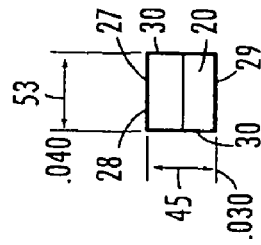

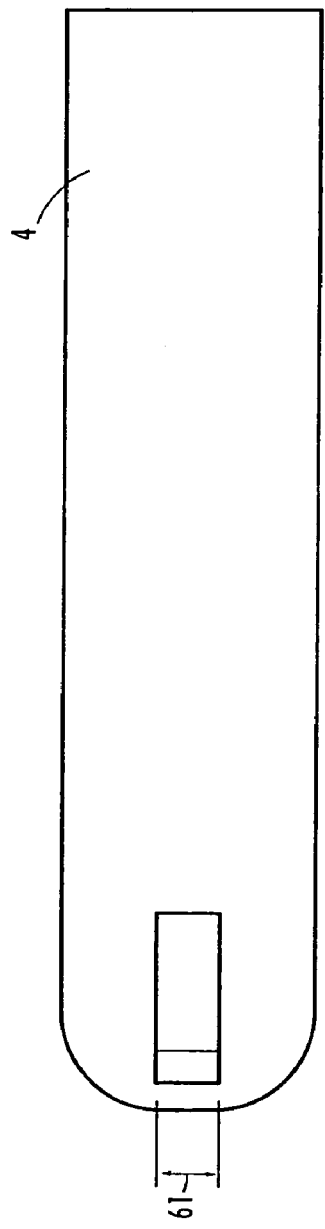
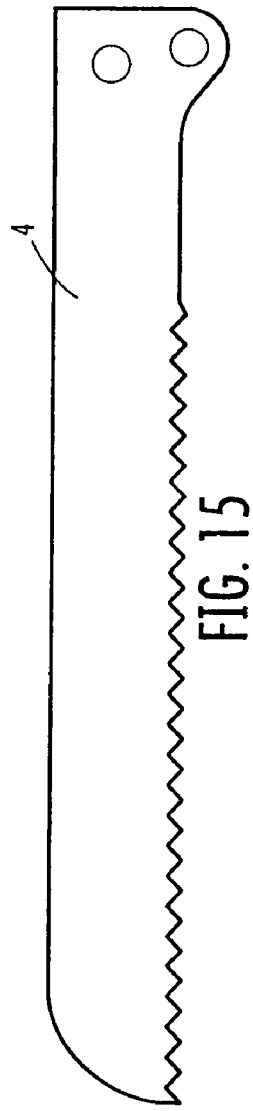
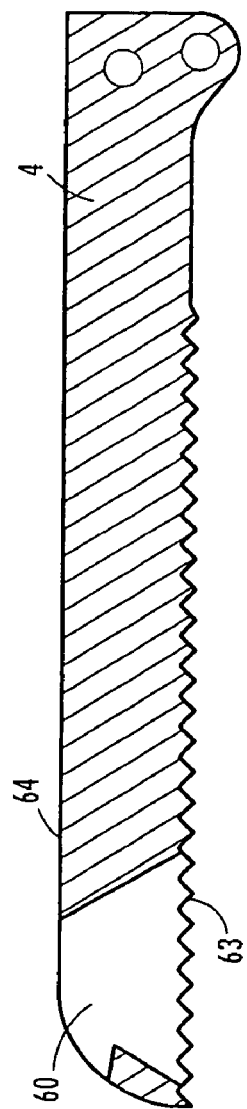
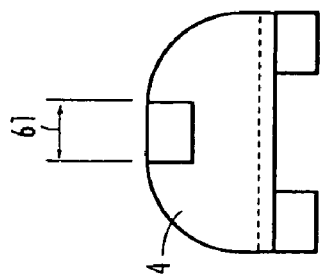

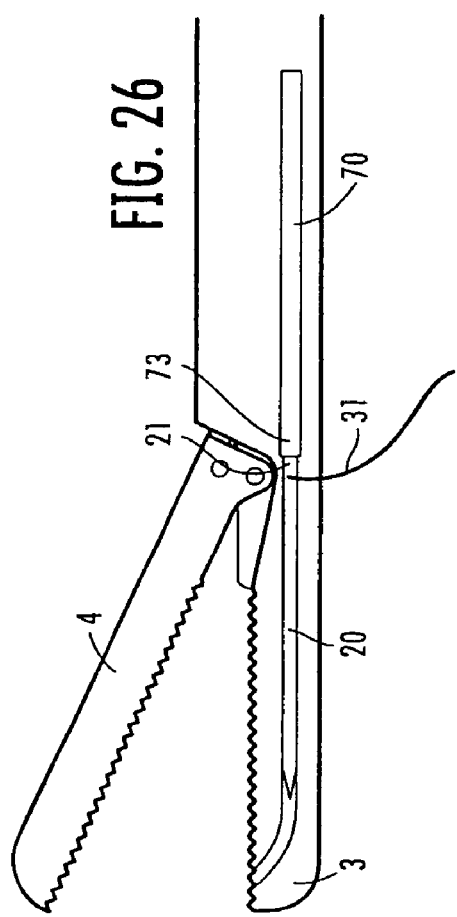
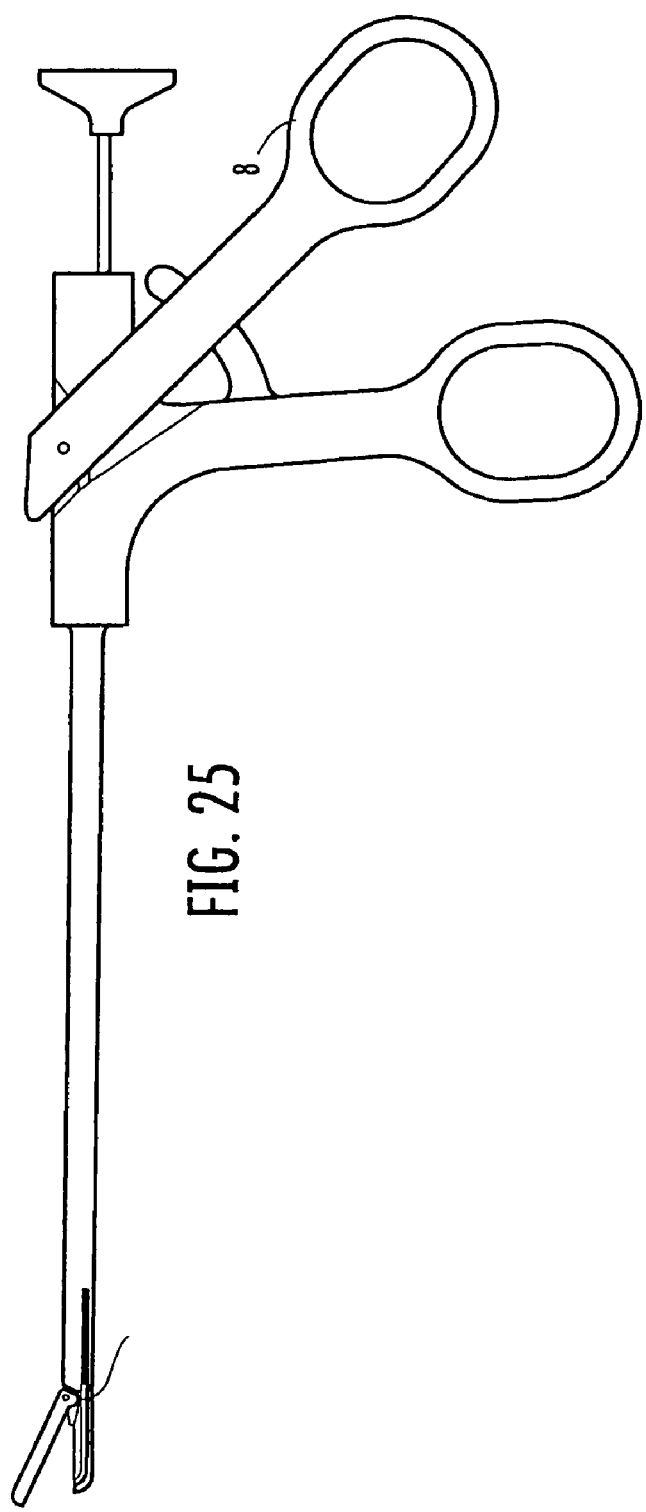

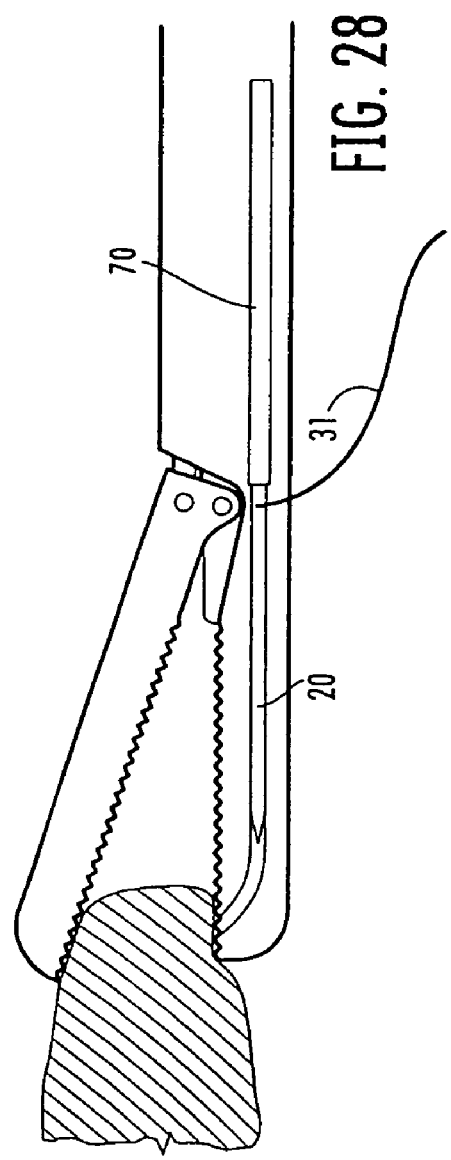
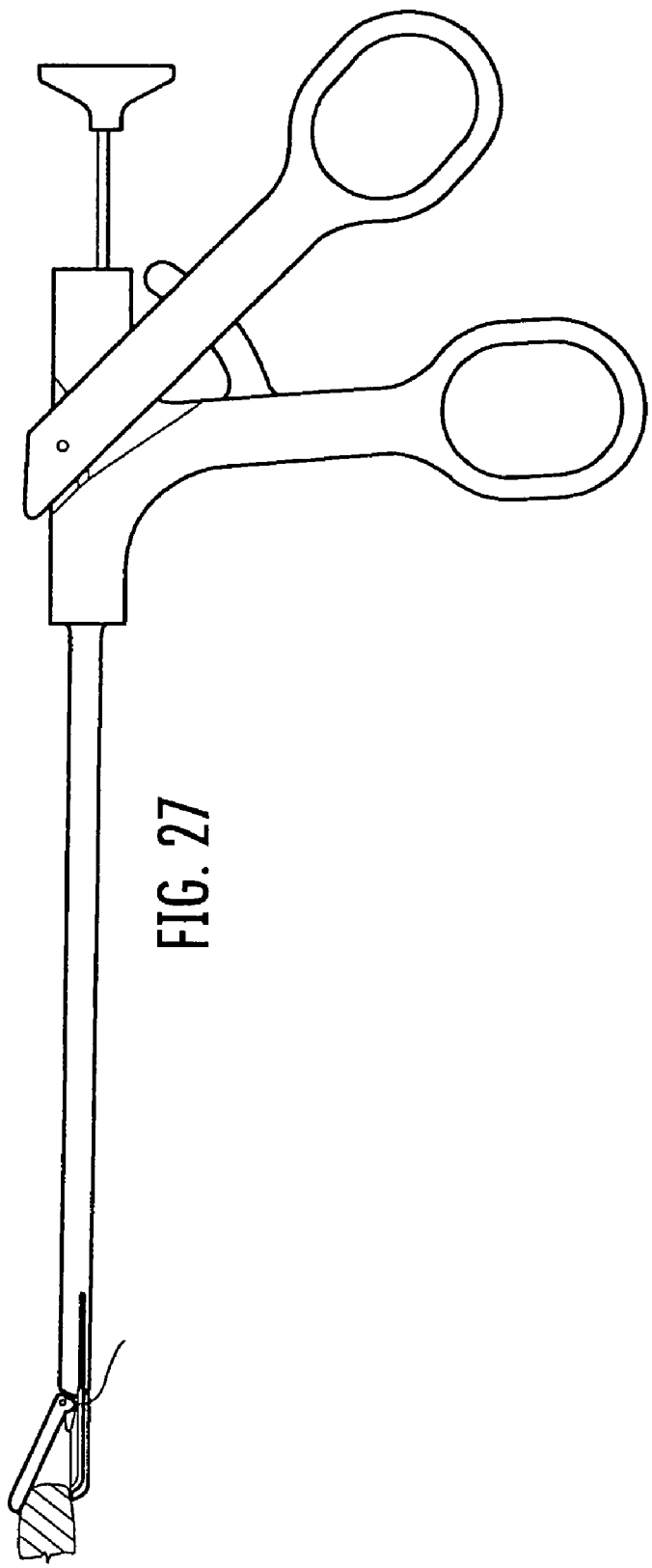
FIG. 28
FIG. 27

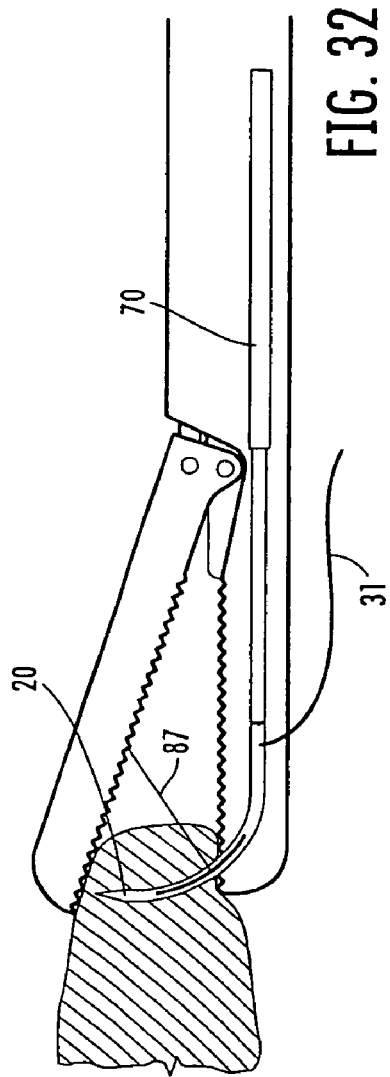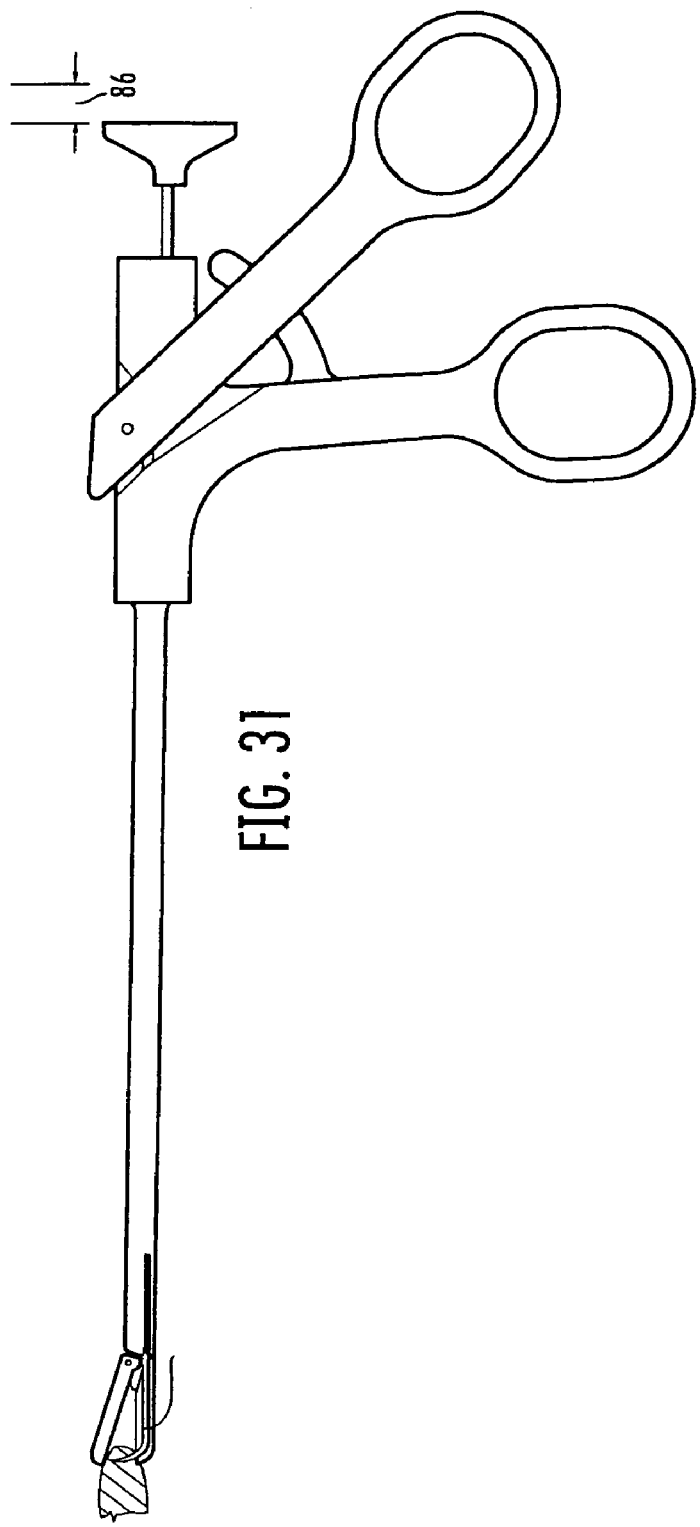

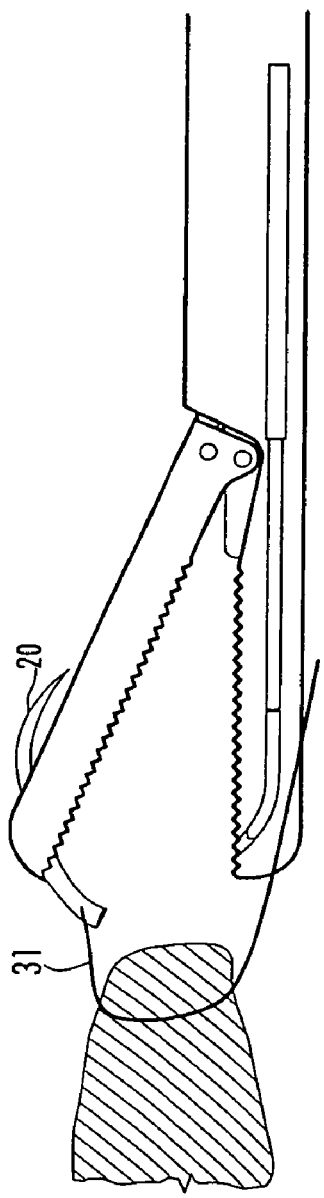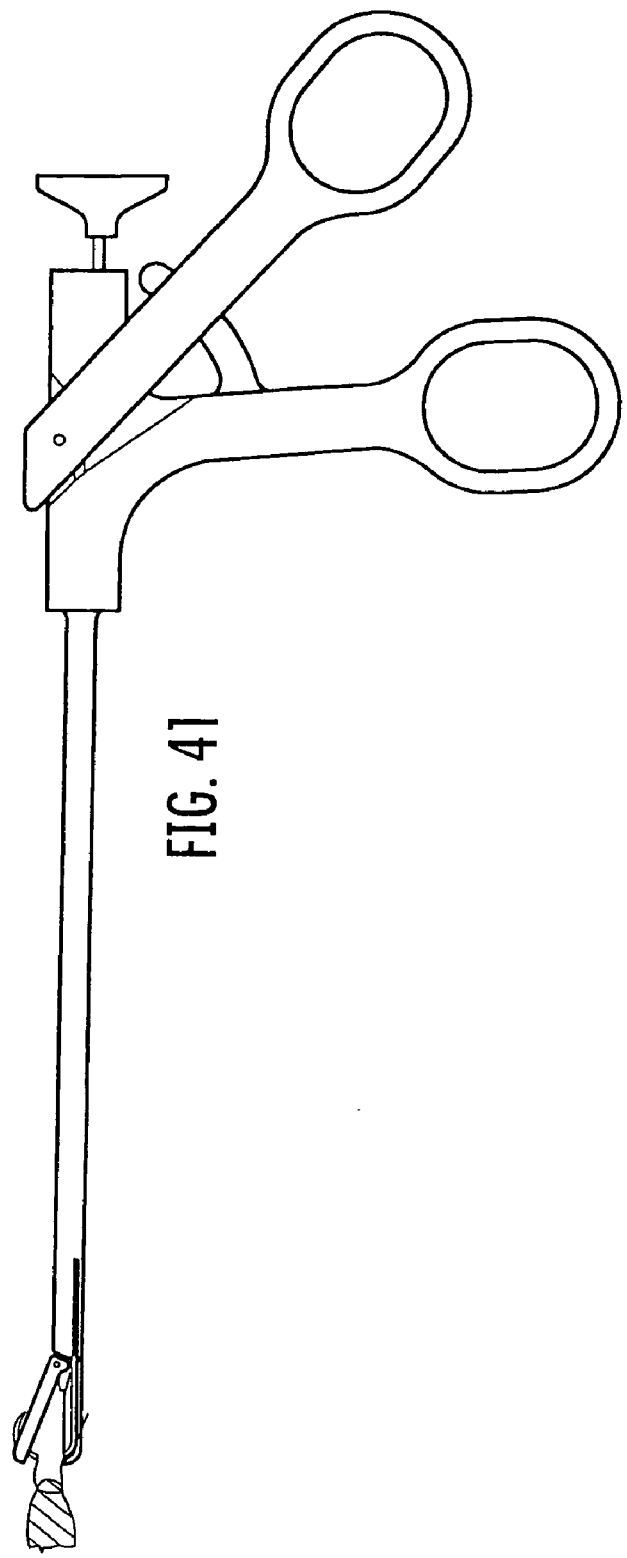
FIG. 42
FIG. 41

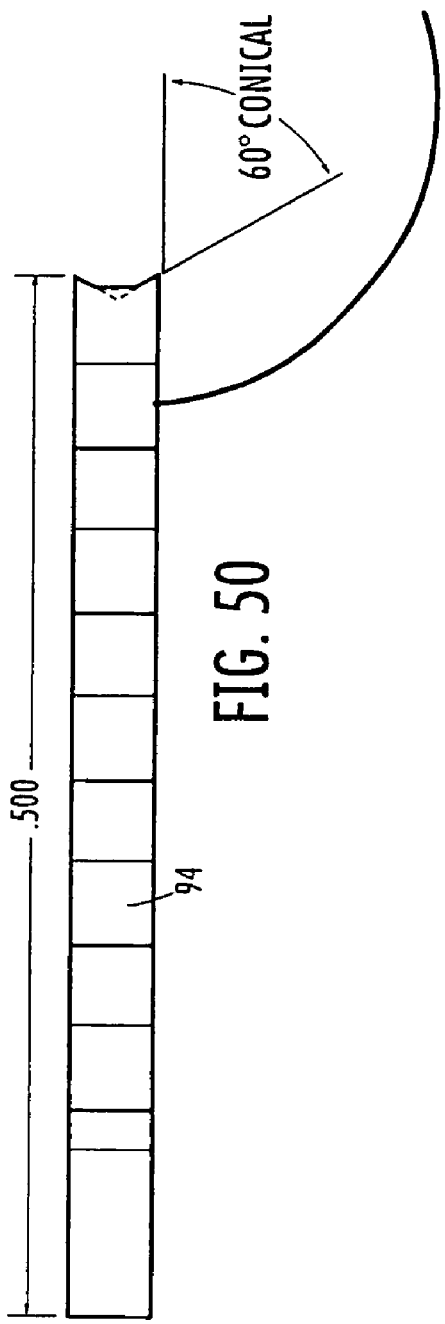
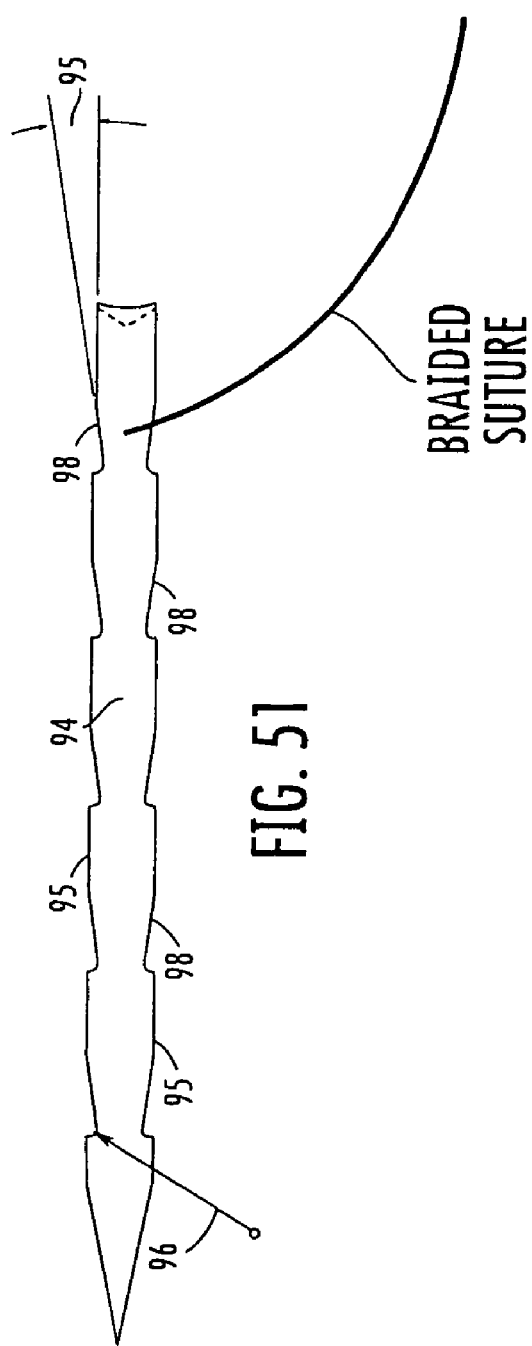
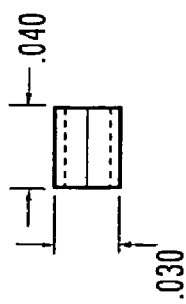

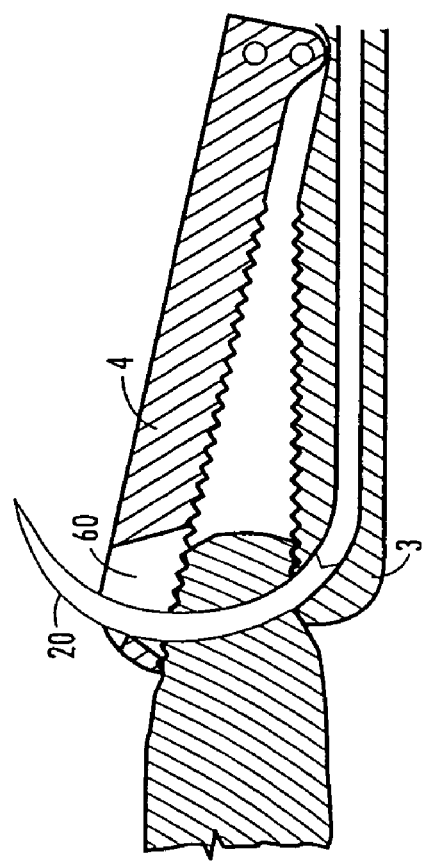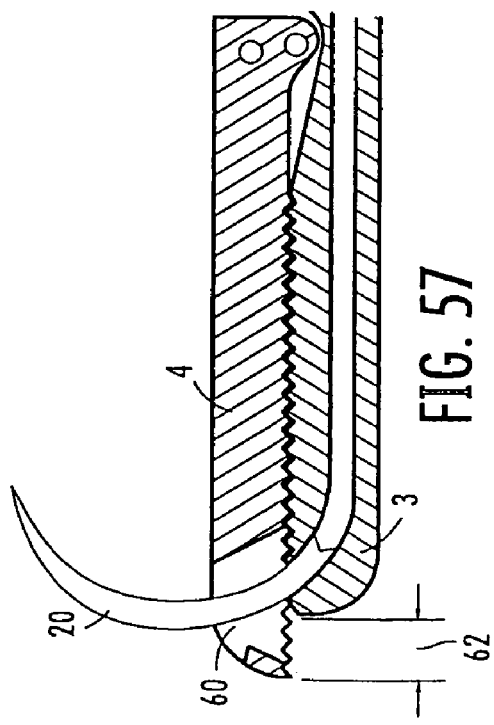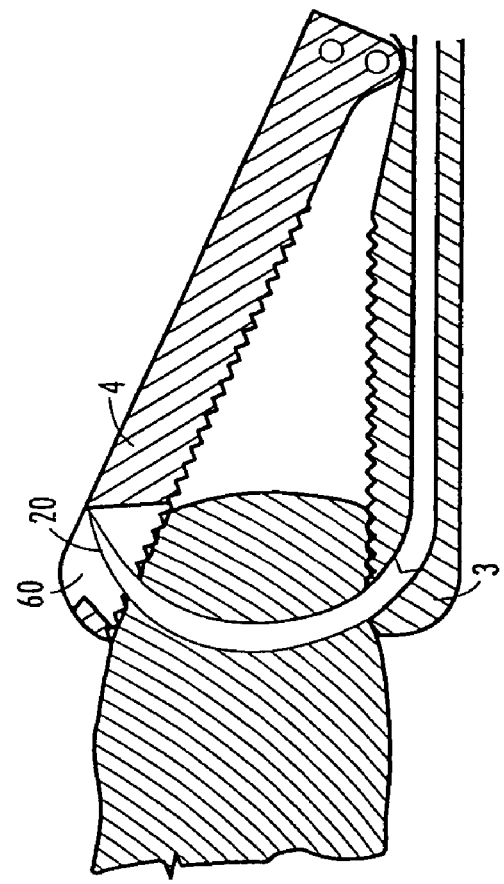

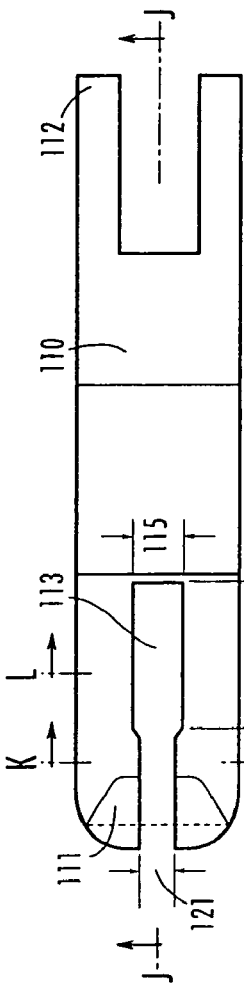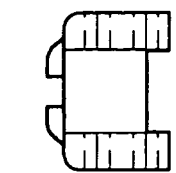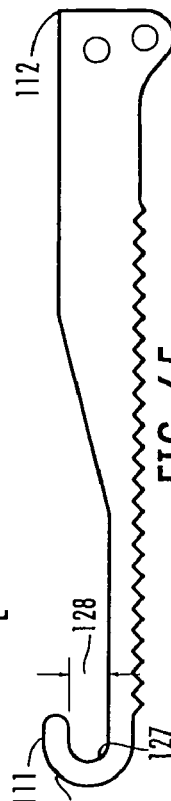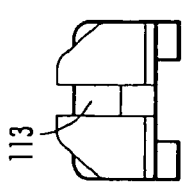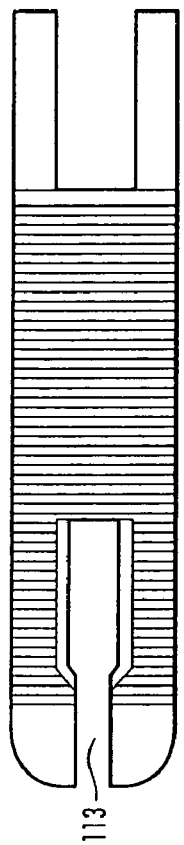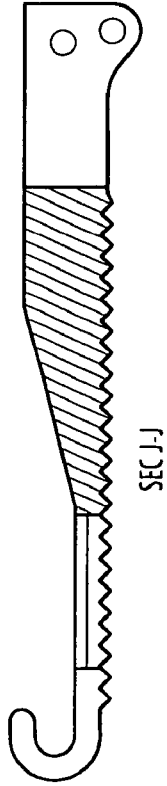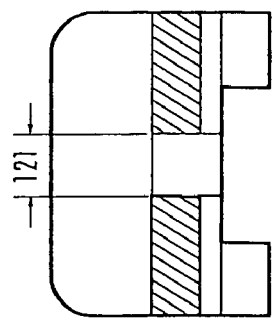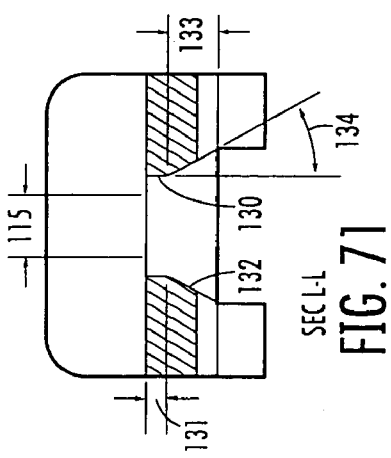

1

2

3

4

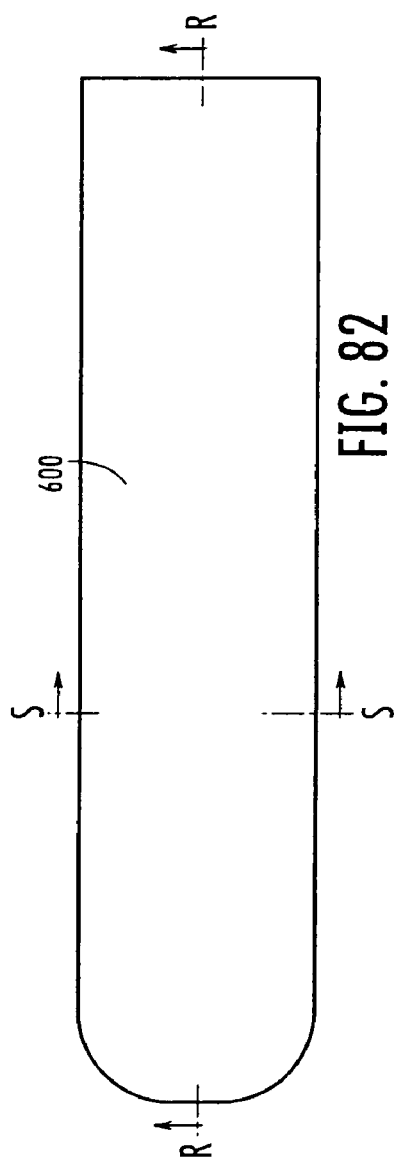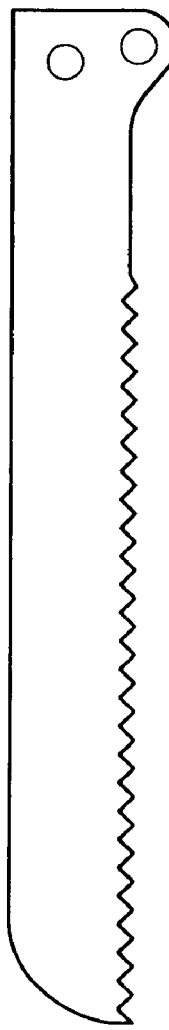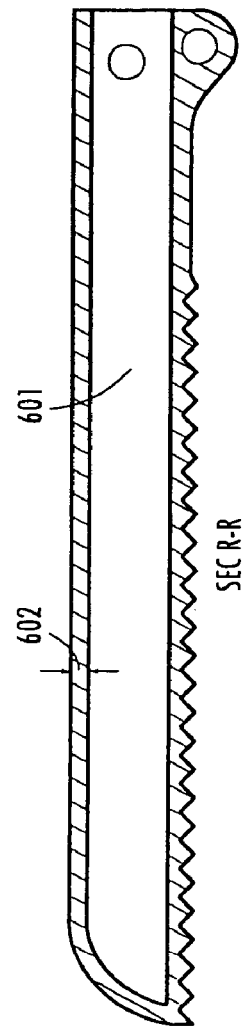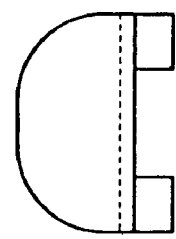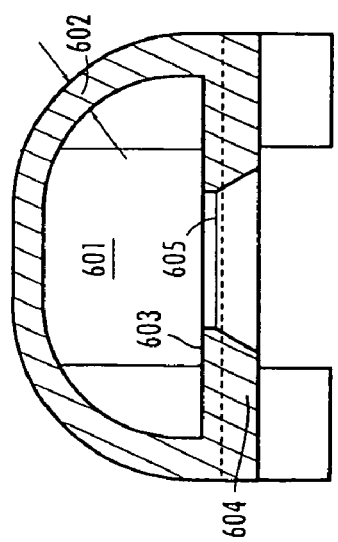

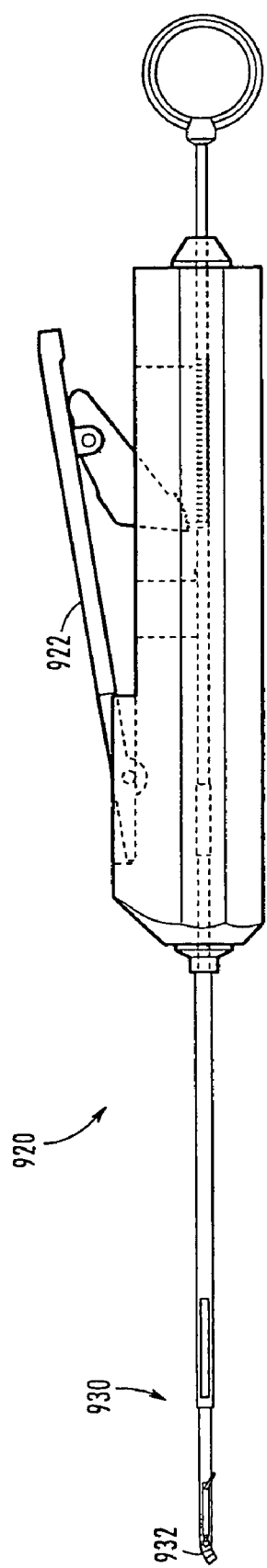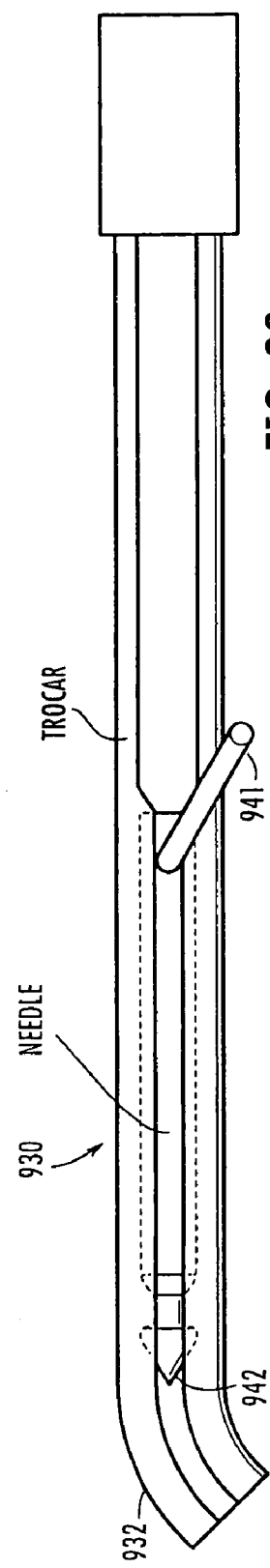

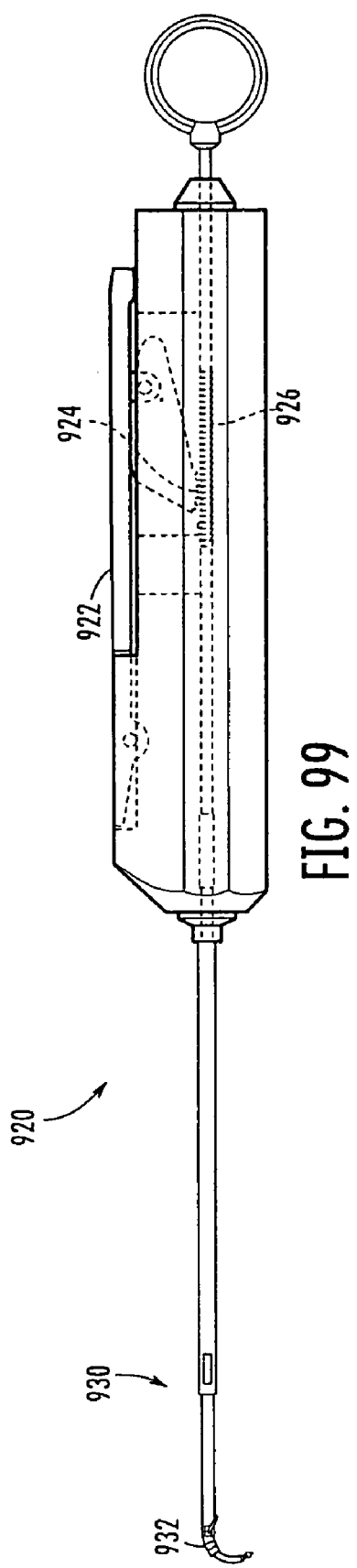

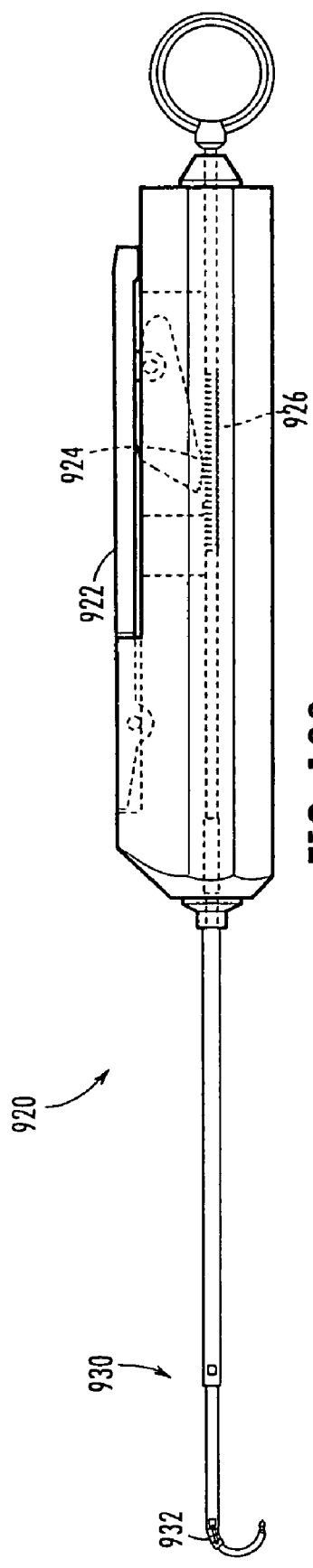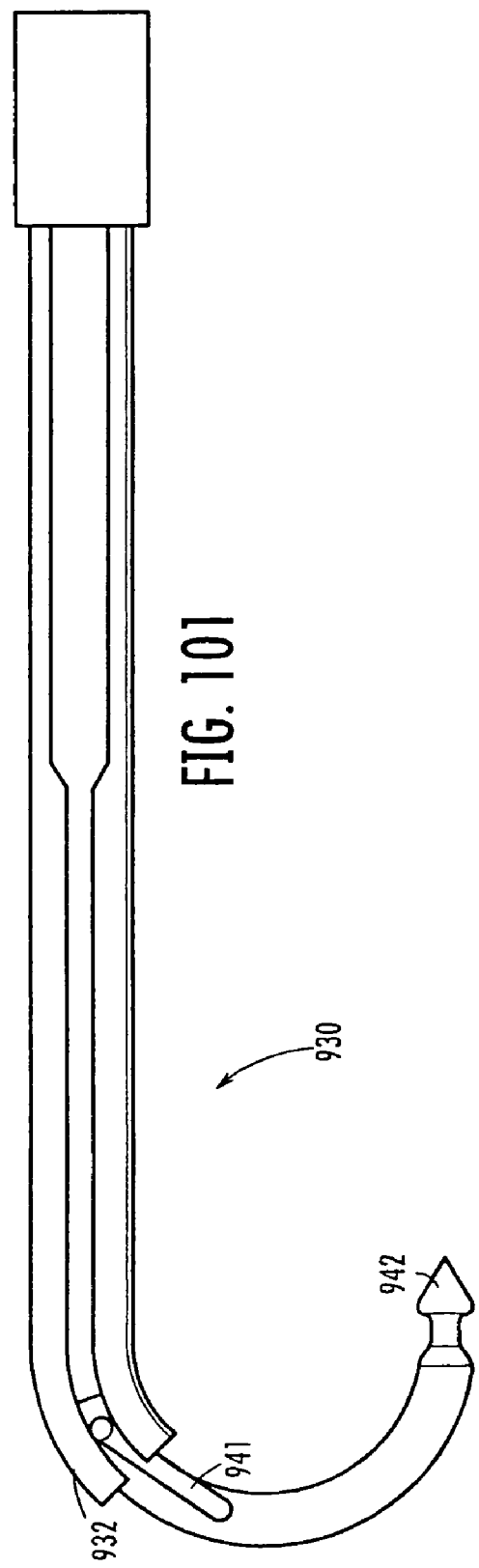
FIG. 100
FIG. 101

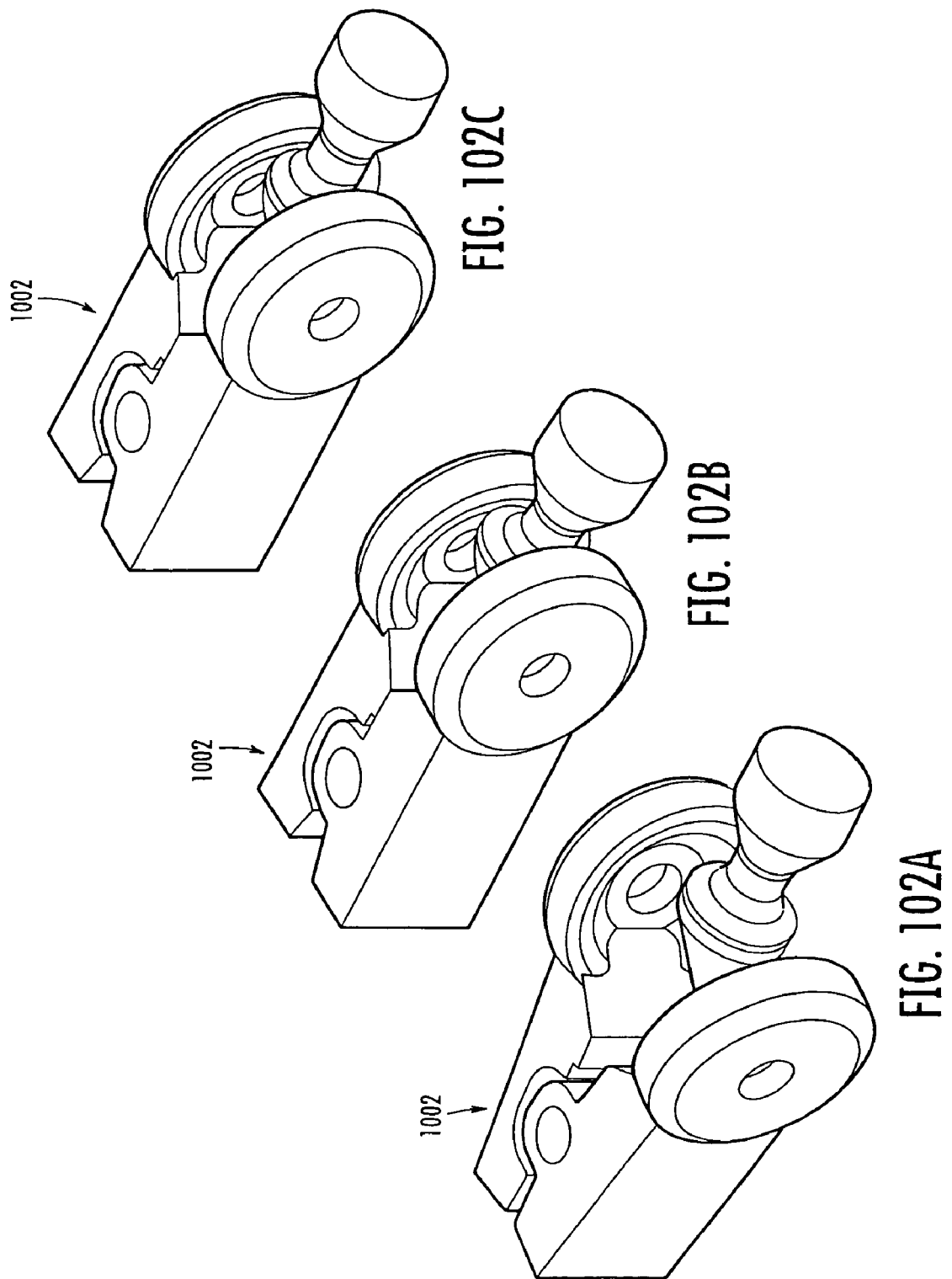

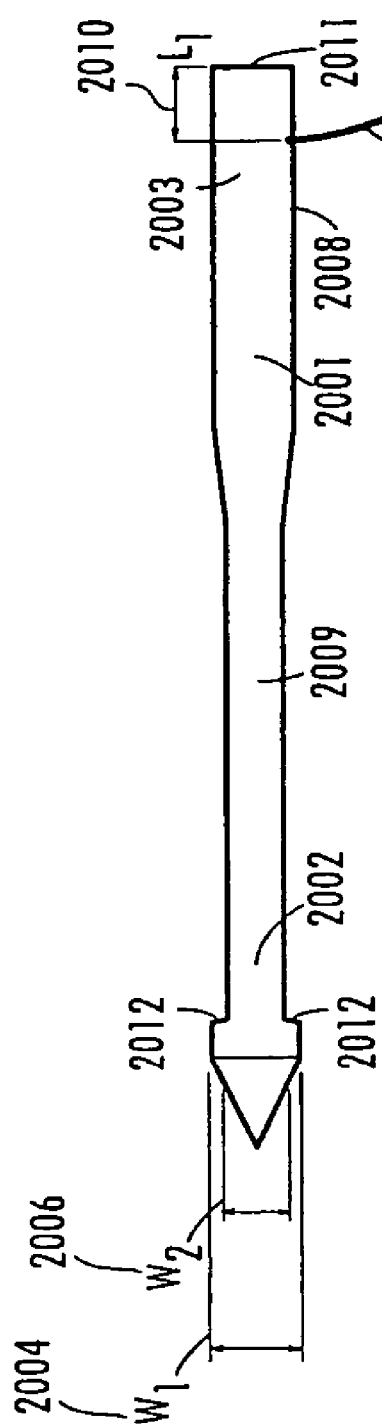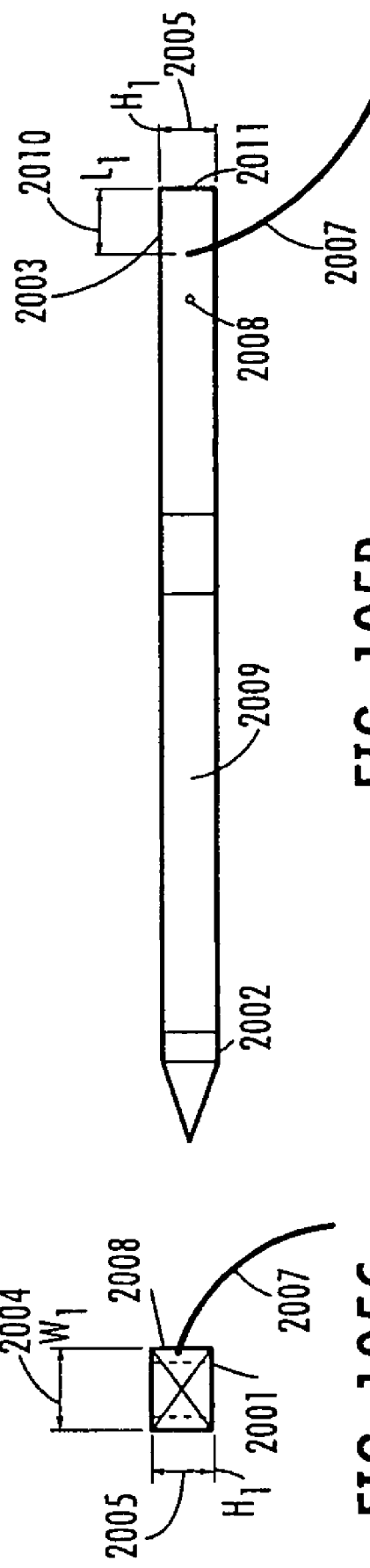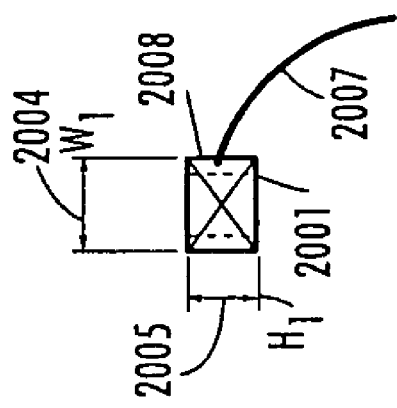
FIG. 105A
FIG. 105B
FIG. 105C

COMPACT SUTURE PUNCH WITH MALLEABLE NEEDLE

REFERENCE TO RELATED APPLICATION

This application is a continuation application of U.S. patent application Ser. No. 10/815,338, filed Apr. 1, 2004, which is a continuation-in-part application of U.S. patent application Ser. No. 10/165,468, filed Jun. 7, 2002, which claims priority to U.S. Provisional Patent Application Ser. No. 60/310,220, filed Aug. 6, 2001.

FIELD OF THE INVENTION

This invention relates generally to surgical suturing and, in particular, to improved articles, instrumentation, and methods therefore.

BACKGROUND OF THE INVENTION

Suture passing is problematic for the arthroscopic surgeon because the braided suture preferred by most arthroscopists cannot be pushed through a cannulated instrument. Braided suture must be pulled into location because applying a push force causes the braid to expand in diameter, thereby wedging in the instrument.

Various solutions have been devised for passing braided suture. The Caspari Suture Punch (Linvatec Corporation, Largo, Fla.) has been a very useful arthroscopic suture-passing instrument. Tissues may be approached head on, grasped and punctured with a cannulated needle, then monofilament suture wheeled through the tissue. A doubled monofilament may be used as a shuttle to pass another braided suture or, alternatively, a Linvatec Suture Shuttle may be wheeled through a slotted Caspari Suture Punch and used to shuttle suture. Surgical Dynamics has a similar device that shuttles a needle from one side of the punch to the other, passing the needle and attached thread through tissue.

The Caspari suturing instrument, described in U.S. Pat. Nos. 4,890,615, 4,923,461 and 4,957,498, includes a hollow needle for penetrating tissue to be sutured within the body while the tissue is clamped between relatively movable jaws, and a suture feed mechanism for feeding suture material through the hollow needle such that the jaws may be opened and the suturing instrument withdrawn from the body pulling the free end segment of the suture material with the instrument. A knot may be tied in the suture material externally of the body and the knot moved back into the body at a position adjacent the tissue.

U.S. Pat. No. 5,254,126 discloses an endoscopic suture punch for use in endosurgical procedures having an elongate frame and a handle mounted to one end of the frame. A pair of opposed jaws having tissue punches is mounted to the other end of the frame. One jaw is rigidly mounted to the frame while the other jaw is movably mounted to the frame, although both jaws may be movably mounted. An actuation handle is mounted to the frame for actuating the jaws. The suture punch has a suture pathway through the frame, the punches and the jaws for receiving the suture. There is a suture drive mechanism mounted to the frame for moving the suture through the suture pathway.

The surgical suturing apparatus described in U.S. Pat. No. 5,454,823 comprises upper and lower jaw elements selectively movable relative to one another between open and closed position. Each jaw element is provided with a respective recess arranged to receive a portion of an elongate incision member or length of surgical thread and securing means is provided arranged to selectively secure the surgical incision member or length of surgical thread in a respective recess. The jaw elements are typically provided at an end of an elongate positioning and operating arm making the device particularly useful for use in laparoscopic surgery.

More recently, U.S. Pat. No. 6,051,006 describes a suture-passing forceps having a first jaw with a mount which supports a needled suture and a second jaw having a passage, which when aligned with the mount, is positioned to receive the needled suture. The second jaw is positioned relative to the mount in a manner which allows delivery of the instrument to a surgical site in a low profile, delivery position (e.g., with the jaws spaced relatively closely). The surgical instrument includes an elongated shaft having a distal region for supporting the jaws. The second jaw is pivotable, with respect to the mount, between the delivery position in which the second jaw is spaced relatively closely to the mount with the passage misaligned with the mount and an open, misaligned position, the second jaw being axially translatable relative to the mount to an open, aligned position in which the passage is aligned with the mount.

A shortcoming of these and other such devices is the lack of room available to open the jaws sufficiently in tight spaces (a clearance issue), difficulty in forcing the tooth through the full thickness of the tissue (the tip gradually dulls and some tissue like the rotator cuff is just too thick) and fairly large diameter cannulas are required for passage.

Other "blitzes" and similar devices also have rather large diameter cannulated needles that pierce the tissue then deploy a loop or other mechanism to transport suture through the tissue. These are cumbersome to use, often requiring skillful rotation and pushing of the device by the surgeon to accomplish the selected result. Additionally, some concern exists with regard to the size of the hole placed in the tissue and the amount of damage requiring repair. This is especially true of the newer "Arthropierce" instrument currently in use.

Common to existing devices is a body capable undergoing elastic deformation during use but which retains a preformed shape when in an unconstrained condition. Of particular usefulness in these devices is Nitinol, a so-called "shape retention" alloy having an extremely high yield point. Nitinol components are formed during manufacture to a selected shape, and will return to this shape when in an unconstrained condition even after undergoing significant deformation. Preformed Nitinol needles and shuttles may be passed through cannulated instruments and will return to their original shapes when in an unconstrained state. This allows shuttle loops to be passed through cannulated instruments without permanent deformation. All Nitinol components may be formed to their selected shapes during manufacture.

As an example of an invention utilizing this effect, U.S. Pat. No. 5,607,435 describes a medical instrument including a tubular section having a leading end terminating in a sharp point and a surgical needle exhibiting "superelastic characteristics." As such, the needle may remain straight as it is inserted through the delivery tube without developing substantial permanent deformation. While in the delivery tube and in this substantially straight condition, the needle is delivered to the suturing site. Once at the suture site, the surgical needle is extended out of the leading end of the delivery tube, returning it to its original curved or bent shape for suturing. A suture thread or wire is operatively disposed in the bore of the tubular section with one end extending out the tip through a slot so as to remain in position to form a suture upon removal of the tubular needle from tissue. A tweezers instrument may then be used to grip and tie the thread into a suture knot.

Similarly, U.S. Pat. No. 5,749,879 discloses a cannulated instrument for use in conjunction with "an elastic needle." In the preferred embodiment, the needle is of a pseudoelastic shape memory alloy and has an arced shape while the needle's alloy is in a substantially austenitic phase, and the needle may be stressed into a more straight shape in which the needle's alloy enters an at least partially more martensitic phase. When the needle is held entirely within the cannula, the needle is straightened and contains more stress-induced-martensite phase. As the needle is extruded from the distal end portion of the cannula, that portion of the needle which extends beyond the cannula returns toward its original shape by a martensitic-to-austenitic shape memory phase change caused by at least partial relief of the stress-induced-martensite in the needle's alloy. A cannula insert includes a longitudinal bore which may be used to contain a suture attached to the needle. Suitably, the bore may extend longitudinally entirely through the cannula insert, to permit an unlimited length of suture to be pulled therethrough.

Despite these advances, the need remains for a suture punch capable of passing braided suture without the use of a shuttle or similar means. Beneficially, such an instrument would be capable of passing suture while not requiring multiple or complex sequential operations or a high level of surgeon skill. In other embodiments, it would also be beneficial that the suture punch pass through a small diameter (i.e., 8 mm or less) cannula, and that the hole created in the tissue for passage of the suture be as small as possible.

SUMMARY OF THE INVENTION

This invention overcomes deficiencies in the prior art by providing a suture punch system capable of directly passing suture material, such as braided suture material, through tissue in a simple, one-step process. The system includes three principle components: a malleable needle capable of delivering the suture material to the tissue, a handheld instrument for grasping tissue and controlling needle placement, and a trocar or other mechanism to supply the force required for needle formation and placement.

The needle differs from standard needles in terms of size, shape and material properties. In beneficial embodiments, the needle is shorter than standard needles, generally 10 to 13 mm in length, and has a cross-section which may be circular or non-circular, including rectangular with at least two parallel sides. The rectangular needles may have varying thicknesses and have a cross-section that ranges from substantially square to substantially flat. Additionally, the needle is made of a malleable material permitting it to be shaped within the handheld instrument and to retain its form while passing through tissue. The needle may also return to its form after passing through the tissue or once any bending force has been removed. Similarly, the distal portion of the trocar may be malleable, thereby permitting shaping within the handheld instrument.

In contrast to existing suture punches in which the needle or shuttle undergoes only an elastic deformation during use and the functional un-constrained shape of the needle or shuttle is produced during manufacture, the needle of the disclosed device may be inelastically formed to its functional shape during use, allowing the needle to traverse a nonlinear path. More particularly, when passing through the distal tip of the hand instrument, the needle may be inelastically formed by a radial path within the instrument, the plane of the radius being substantially unparallel to the tissue through which the suture is being passed. The formation of this radius is facilitated by the aforementioned parallel sides of the needle cross-section which are constrained by the instrument in such a manner as to place them essentially in the plane of the tissue.

Needle deformation begins as the tip of the needle passes through the radius within the instrument and continues as the needle is forced distally by a force-supplying mechanism. As the distal tip of the needle pierces the tissue, it continues its radial path through the tissue, the radius of the path being determined by the unconstrained radius of the needle. This unconstrained radius may be larger than that of the forming radius within the instrument due to "spring back" of the needle, the degree of which is determined by the material properties of the needle, its cross section, and features formed in the parallel surfaces of the needle during manufacture.

Forming of the needle along its length continues as it is passes from the distal tip of the instrument into the tissue. When the proximal end of the needle exits from the instrument, the needle may be entirely radial in shape and traverse an essentially radial path through the tissue. Due to the degree of spring back, the needle, in certain embodiments, may also return to its non-deformed shape. As used herein, the term "spring back" is meant to define the degree of elasticity of the malleable needle after it has exited the instrument. A "spring back" of 100 percent would apply to a needle that returns to its original shape whereas a needle having a "spring back" of 0 percent would maintain the shape of the curved segment of the instrument after the needle has exited the instrument. The present invention may use needles having a degree of spring back of from 0 to 100 percent. In select embodiments, wherein an inelastic material is used, the needle has a spring back of from 0 to about 10 percent. In alternative embodiments, wherein an elastic material is used, the needle has a spring back of from about 90 to about 100 percent.

After the proximal end of the needle exits the instrument, the needle may be propelled further along its radial path by the force-supplying mechanism, such as a trocar. Additionally, the distal portion of the mechanism may be formed to a radial shape by the instrument in the same manner as the needle. Additionally, the radial shapes of the needle and mechanism may also be coplanar. Engagement of the mechanism with the needle after the needle passes from the instrument may be facilitated by mating surfaces of the mechanism and needle, shaped, for example, to prevent radial or lateral displacement of the needle proximal and mechanism distal surfaces. The mechanism may also be engaged with the needle in a manner that connects the mechanism and needle together such that the connection is capable of being broken after the needle has exited the instrument.

The passage in the instrument within which the needle travels, and the forming radius in the instrument distal tip, each comprise open-sided channels allowing the suture carried by the needle to travel unimpeded during its forming and insertion into the tissue. As the force-supplying mechanism pushes the needle further into the tissue, the suture is carried along by the needle through the passage formed in the tissue to deliver the suture to the tissue.

During use, the tissue to be sutured is constrained by pressure applied through closure between the upper, moveable jaw of the instrument and the distal portion of the instrument which acts as a fixed jaw. The upper, movable jaw contains a shaped passageway that allows the curved needle to pass therethrough during use. After the force-supplying mechanism has been fully inserted into the instrument and the needle has achieved maximum travel into the tissue, the mechanism may be withdrawn from the instrument.

When suturing thin sections, the needle may be passed completely through the tissue and may then be ready for retrieval using the jaws of the punch or another instrument. In the case of thick tissue, 70 percent or more of the needle may protrude from the tissue after the force-supplying mechanism is fully inserted, such that opening the upper jaw slightly and moving the instrument in a proximal direction would cause the needle to wedge in the upper jaw passage, permitting the needle to be withdrawn completely from the tissue. Following this procedure, the needle may be retrieved using the punch or another instrument.

Accordingly, in one embodiment, the present invention provides suturing instrumentation for suturing tissue having a malleable needle portion having a sharpened distal tip and constructed and arranged to deliver a length of suture material to the tissue; a handheld instrument having a passageway and having a distal end terminating in a nonlinear portion having a first radius; and a force-supplying structure for applying a force to the needle portion, wherein the force-supplying structure includes a distal end capable of pushing the malleable needle portion through the nonlinear portion, such that when the distal end of the handheld instrument is positioned proximate to the tissue to be sutured and the malleable needle portion is pushed by the distal end of the force-supplying structure through the nonlinear portion, the needle portion is deformed, thereby causing the needle portion to deliver the suture material to the tissue.

In another embodiment, the present invention provides suturing instrumentation for suturing tissue having a malleable needle portion having a sharpened distal tip and constructed and arranged to deliver a length of suture material to the tissue; a handheld instrument having a passageway and having a distal end terminating in a nonlinear portion having a first radius; and a force-supplying structure for applying a force to the needle portion, wherein the force-supplying structure includes a distal end capable of pushing the malleable needle portion through the nonlinear portion, such that when the distal end of the handheld instrument is positioned proximate to the tissue to be sutured and the malleable needle portion is pushed by the distal end of the force-supplying structure through the nonlinear portion, the needle portion is deformed, thereby causing the needle portion to deliver the suture material to the tissue; and a jaw pivotally coupled to the distal end of the handheld instrument for holding tissue as the needle portion and suture material enters into the tissue.

In yet another embodiment, the present invention provides a suture needle adapted for use with a handheld instrument defining an axis and having an off-axis distal end, the needle including a length of material having a sharpened distal tip and constructed and arranged to deliver a length of suture material; and the material of the needle being malleable, such that when the needle is pushed through the handheld instrument, it elastically deforms in accordance with the off-axis distal end.

In still another embodiment, the present invention provides a suturing system having a malleable needle portion having a sharpened distal tip and constructed and arranged to deliver a length of suture material; a handheld instrument having a passageway and having a distal end terminating in a nonlinear portion; and a push member configured for movement in the passageway of the handheld instrument, the push member being operative to push the malleable needle portion through the nonlinear portion, such that when the distal end of the handheld instrument is positioned proximate to a tissue to be sutured and the needle portion is pushed by the push member through the nonlinear portion, the needle portion is deformed and enters into the tissue and delivers the suture material to the tissue being sutured.

In yet another embodiment, the present invention provides a method for suturing, including the steps of providing a malleable needle portion having a sharpened distal tip; positioning the needle in a passageway of a handheld instrument; providing a suture material to be delivered by the needle portion; and using a push member to push the needle portion in the handheld instrument, the needle portion upon exiting the handheld instrument penetrating the tissue being sutured and delivering the suture material to the tissue being sutured.

In still another embodiment, the present invention provides a system and method for suturing using a smaller suture wherein the needle is designed such that the suture may be looped back directly into the needle. As such, when the push member pushes the needle portion into and/or through the tissue, the needle delivers a loop of suture material that may then be used as an eyelet or other mechanism for the transfer of other suture. Alternatively, a smaller needle may be used during delivery of the suture to create a loop of suture material in the tissue to be sutured.

BRIEF DESCRIPTION OF THE DRAWINGS

FIG. 1 is a plan view of a suture punch formed in accordance with the principles of this invention;
FIG. 2 is a side view of the instrument of FIG. 1;
FIG. 3 is an end view of the instrument of FIG. 1;
FIG. 9 is a sectional view of the instrument at location E-E with the trocar and needle removed;
FIG. 10 is an expanded view of the distal tip of the instrument;
FIG. 11 is a plan view of a needle constructed in accordance with the principles of this invention;
FIG. 12 is a side view of the needle of FIG. 5;
FIG. 13 is an end view of the needle of FIG. 5;
FIG. 14 is a plan view of the upper jaw of the instrument;
FIG. 15 is a side view of the upper jaw of FIG. 14;
FIG. 16 is a sectional view of the upper jaw of FIG. 14;
FIG. 17 is an end view of the upper jaw of FIG. 14;
FIG. 25 shows a needle and trocar loaded and the upper jaw open in preparation for use;
FIG. 26 is an expanded view of the distal end of the instrument of FIG. 25;
FIG. 27 depicts the instrument grasping tissue in preparation for passing a needle with suture therethrough;
FIG. 28 is an expanded view of the distal end of the instrument grasping tissue as shown in FIG. 27;

FIG. 31 shows the trocar advanced so that the needle has approximately 90 percent penetration of tissue grasped between the instrument jaws;

FIG. 32 is an expanded view of the distal end of the instrument shown in FIG. 31;

FIG. 41 is similar to FIG. 30, but with the distal end retracted proximally from the tissue so that the needle is pulled from the tissue by the moveable jaw;

FIG. 42 is an expanded view of the distal end of FIG. 41;

FIG. 50 is a plan view of yet a further alternate needle configuration according to the invention;

FIG. 51 is a side view of the alternate needle configuration of FIG. 50;

FIG. 52 is an end view of the alternate needle configuration of FIG. 50;

FIG. 57 is a sectional view of upper and lower jaws with jaws closed and needle fully extended;

FIG. 58 is a sectional view of upper and lower jaws with jaws opened 50 percent and needle fully extended;

FIG. 59 is a sectional view of upper and lower jaws with jaws opened 100 percent and needle fully extended;

FIG. 64 is a plan view of an alternate construction of the upper/moveable jaw;

FIG. 65 is a side view of the alternate construction of the upper/moveable jaw of FIG. 64;

FIG. 66 is a bottom-side plan view of the alternate construction of the upper/moveable jaw of FIG. 64;

FIG. 67 is an end view of the alternate construction of the upper/moveable jaw of FIG. 64 from the proximal end;

FIG. 68 is an end view of the alternate construction of the upper/moveable jaw of FIG. 64 from the distal tip;

FIG. 69 is a sectional view of the alternate construction of the upper/moveable jaw of FIG. 64 in direction J-J;

FIG. 70 Is a sectional view of the alternate construction of the upper/moveable jaw of FIG. 64 in direction K-K;

FIG. 71 is a sectional view of the alternate construction of the upper/moveable jaw of FIG. 64 in direction L-L;

FIG. 82 is a plan view of an alternate top jaw according to the invention;

FIG. 83 is a side view of the alternate top jaw of FIG. 82;

FIG. 84 is a side sectional view of the alternate top jaw of FIG. 82;

FIG. 85 is an end view of the alternate top jaw of FIG. 82;

FIG. 86 is an expanded lateral sectional view of the alternate top jaw of FIG. 82;

FIG. 97 is a side-view showing the trocar being advanced by pushing on the proximal end of the pusher rods;

FIG. 98 shows the needle being pushed passed the breached loading position, with the suture material extending out from a slot;

FIG. 99 shows the needle being deformed and pushed out the distal end;

FIG. 100 shows the needle fully advanced, now free of the distal tip of the instrument;

FIG. 101 is a close-up, detail view of the needle emerging from the curved distal tip of the instrument;

FIG. 102A shows the jaws open ready to grab the tip of the needle;

FIG. 102B shows the needle grasped;

FIG. 102C shows how, even once grasped, the tip of the needle may rotate within the jaws;

FIG. 105A is a first view of a needle according to the invention particularly suited to certain shoulder procedures;

FIG. 105B is a different view of the needle of FIG. 105A;

FIG. 105C is a end-on view of the needle of the FIGS. 105A and 105B;

DETAILED DESCRIPTION OF THE INVENTION

Figure 4:
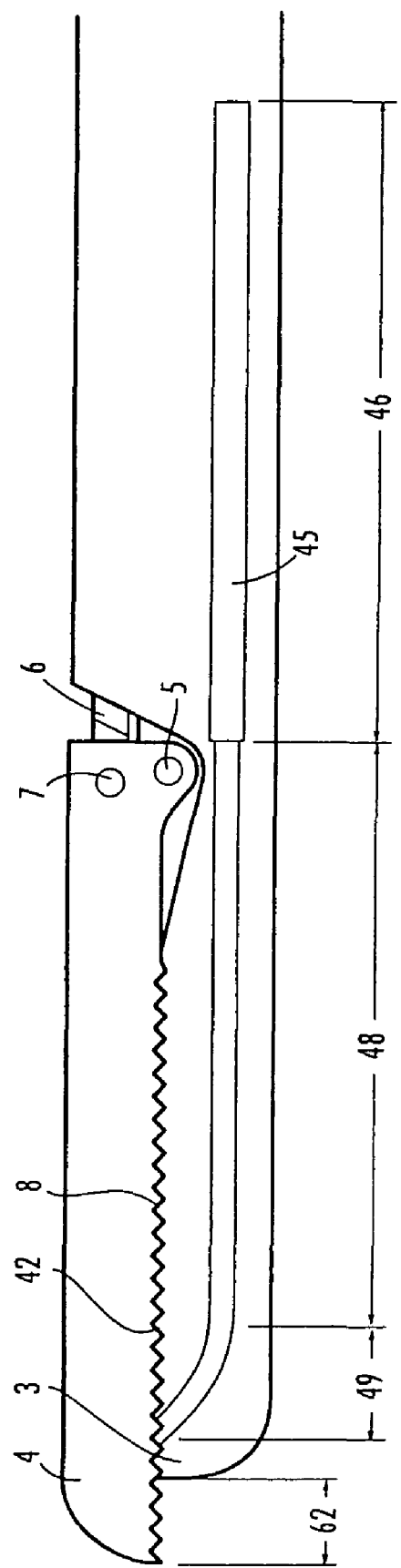
FIG. 4 is an expanded view of the distal tip of the instrument of FIG. 1.

The present invention is more particularly described in the following examples that are intended to be illustrative only since numerous modifications and variations therein will be apparent to those skilled in the art. As used in the specification and in the claims, the singular form "a," "an," and "the" may include plural referents unless the context clearly dictates otherwise. Also, as used in the specification and in the claims, the term "comprising" may include the embodiments "consisting of" and "consisting essentially of."

The present invention will now be further described through the following drawings. It is to be understood that these drawings are non-limiting and are presented to provide a better understanding of various embodiments of the present invention and are not intended to represent every possible embodiment of the present invention.

Referring to the drawings, as best seen in FIGS. 1 through 9, the instrument body 11 has a proximal end 1 and a distal end 2. The distal end further includes a fixed portion (or fixed jaw) 3 and a movable portion (or moveable jaw) 4. The movable portion 4 is rotatable about pin 5 passing through the movable portion 4 and fixed portion 3 thereby forming a hinge.

The position of movable jaw 4 is determined by positioning rod 6 which transmits an opening or closing force to movable portion 4 via hinge pin 7. The position of positioning rod 6 is determined by the position of movable handle 8, which is connected to the proximal end of positioning rod 6 through pin 9. The positioning rod 6 passes through elongated section 18 of instrument body 11 and through passage 17.

Movable handle 8 is rotatably affixed to the instrument body 11 by pin 10 so that rotating movable handle 8 counter-clockwise opens movable jaw 4 and rotating movable handle 8 clockwise closes movable jaw 4 with a closure force proportional to that applied between movable handle 8 and fixed handle 12. Closure pressure between the jaws may be maintained by a ratcheting action created through the interaction between tooth section 13 of movable handle 8 and serrations 14 on arcuate section 15 of fixed handle 12.

Closure pressure may be released by elastically deforming arcuate section 15 upward with pressure applied to proximal end 16 of the arcuate section. Fixed jaw 3 and movable jaw 4 may include serrations 8 formed on their angularly transposed surfaces to facilitate the grasping of tissue placed between them. Removable trocar 70 protrudes from the proximal end of instrument body 11.

As is best seen in FIGS. 11 through 13, one embodiment of the needle 20 has a proximal end 21 and a distal end 22, and a rectangular cross-section 27 with upper surface 28, lower surface 29 and lateral surfaces 30. The proximal end 21 includes a contoured proximal surface 23, conical in shape in one embodiment, and having a conical angle 24 and a conical axis 25 coaxial with needle centerline 26. The distal end 22 is shaped to form a cutting edge 28 having included angle 27. Suture 31 is connected to a needle lateral surface 30 at a distance 32 from the needle proximal end.

Figure 7:
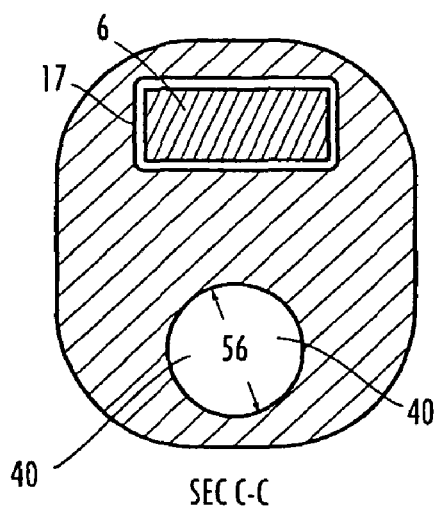
FIG. 7 is a sectional view of the instrument at location C-C.
Figure 8:
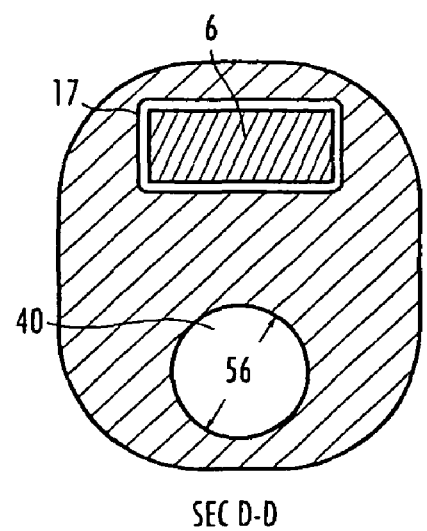
FIG. 8 is a sectional view of the instrument at location D-D.
Figure 20:
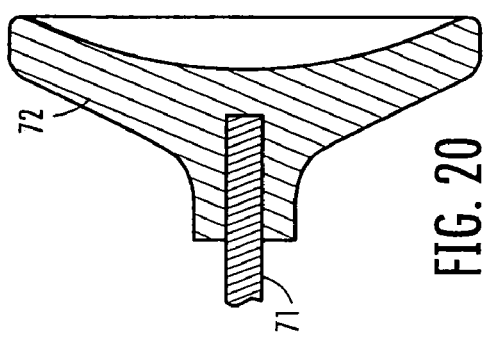
FIG. 20 is an expanded sectional view of the proximal end of the trocar of FIG. 18.
Figure 18:
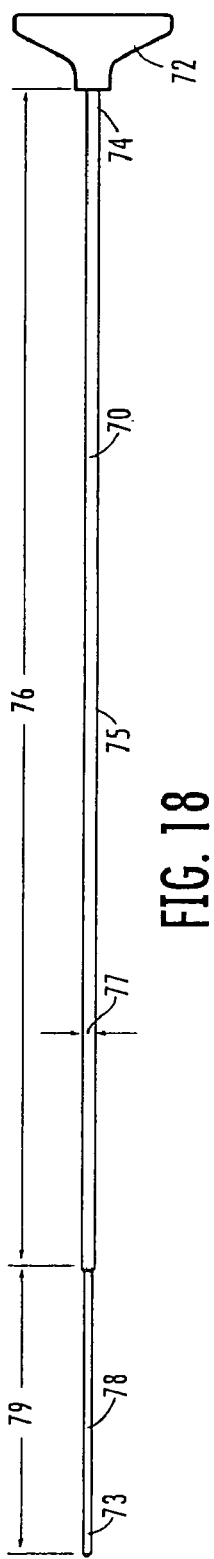
FIG. 18 is a trocar used in accordance with one embodiment of this invention.
Figure 19:
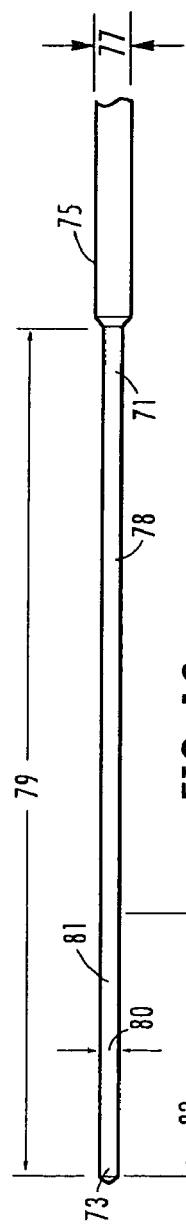
FIG. 19 is an expanded view of the distal end of the trocar of FIG. 18.
Figure 21:
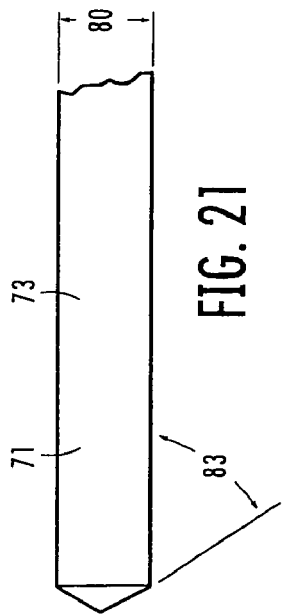
FIG. 21 is an expanded view of the distal portion of the trocar of FIG. 19.
Figure 22:
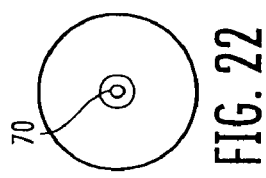
FIG. 22 is an end view of the trocar of FIG. 18.

As is best seen in FIGS. 4, 5, 9, and 10, the instrument body 11 has a continuous passage 40 of varying cross-section extending from the proximal-most face 41 of instrument body 11 to the upper surface 42 of fixed jaw 3 near the jaw's distal tip. In section 43, extending a distance 44 from proximal face 41, the passage has a cylindrical cross-section of a specified diameter 56 as shown in FIGS. 7 and 8. In section 45, extending a distance 46 from the distal end of section 43, the passage is a rectangular channel 44, the height of the channel 51 being slightly greater than the thickness 45 of needle 20. Distance 46 is sufficiently longer than the length of needle 20 to allow easy placement of the needle in the slot.

Figure 5:
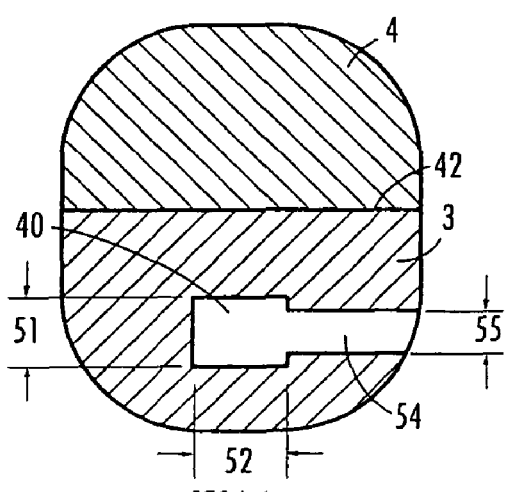
FIG. 5 is a sectional view of the distal tip of FIG. 2 at location A-A.
Figure 6:
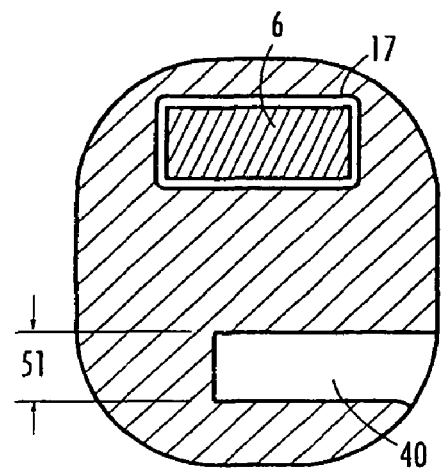
FIG. 6 is a sectional view of the distal tip of FIG. 2 at location B-B.

Section 47 of the slot extends from the distal end of section 45 to the termination of the slot at the top surface 42 of fixed jaw 3 and beneficially includes of a linear portion 48 and a radial portion 49 having a known radius 50. As is best seen in FIG. 5, the cross-section of channel 40 in section 47 is rectangular having a height 51 slightly greater than the thickness 45 of needle 20 and a width 52 slightly greater than width 53 of needle 20. A slot 54 having a height 55 less than height 51 of passage 40 extends through the entirety of section 47.

As is best seen in FIGS. 14 through 17, upper jaw 4 contains a shaped passageway 60 having a width 61 slightly larger than width 52 of passage 40 and extending from the jaw's lower surface 63 to upper surface 64. As best seen in FIGS. 4 and 10, upper jaw 4 protrudes distally a distance 62 beyond lower jaw 3.

Referring to FIGS. 18 through 22, the force-supplying mechanism is a trocar 70 that is an assembly including a stepped cylindrical rod 71 and hub 72 and having a distal end 73 and proximal end 74, with the hub being attached to proximal end 74. Stepped metallic cylindrical rod 71 features a larger diameter section 75 of specified length 76 and diameter 77, with the diameter being slightly smaller than diameter 56 of section 43 of passage 40 so allowing trocar 70 may move freely within instrument body 11 when inserted into passage 40. Cylindrical rod 71 has a smaller diameter section 78 of specified length 79 and diameter 80, with the diameter being slightly smaller than height 51 of sections 45 and 47 of passage 40 allowing trocar 70 to move freely within elongated section 18 of instrument body 11 when inserted into passage 40. Rod 71 is hardened throughout its length to prevent bending, except section 81 extending a length 82 from distal tip 73 is annealed for high malleability. Distal tip 73 is formed to a conical shape of conical angle 83, with the conical angle being equal to conical angle 24 on proximal end 21 of needle 20.

Figure 23:
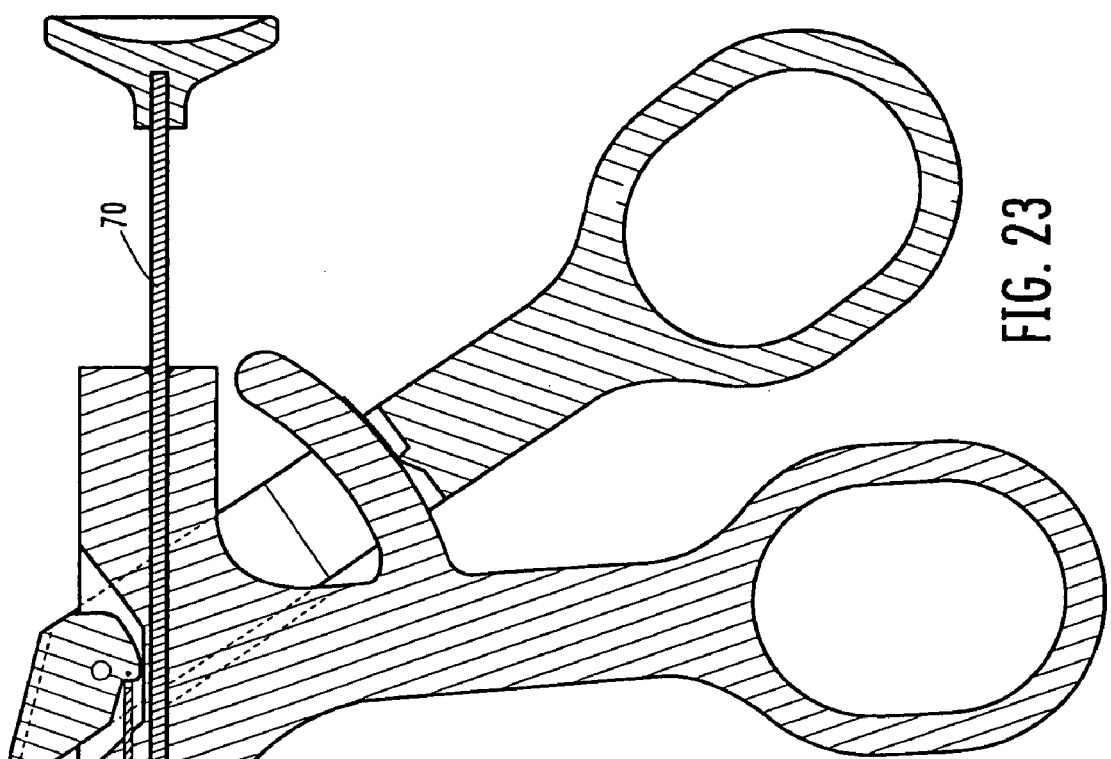
FIG. 23 is a sectional view of the instrument of FIG. 1 with trocar and needle in place.
Figure 24:
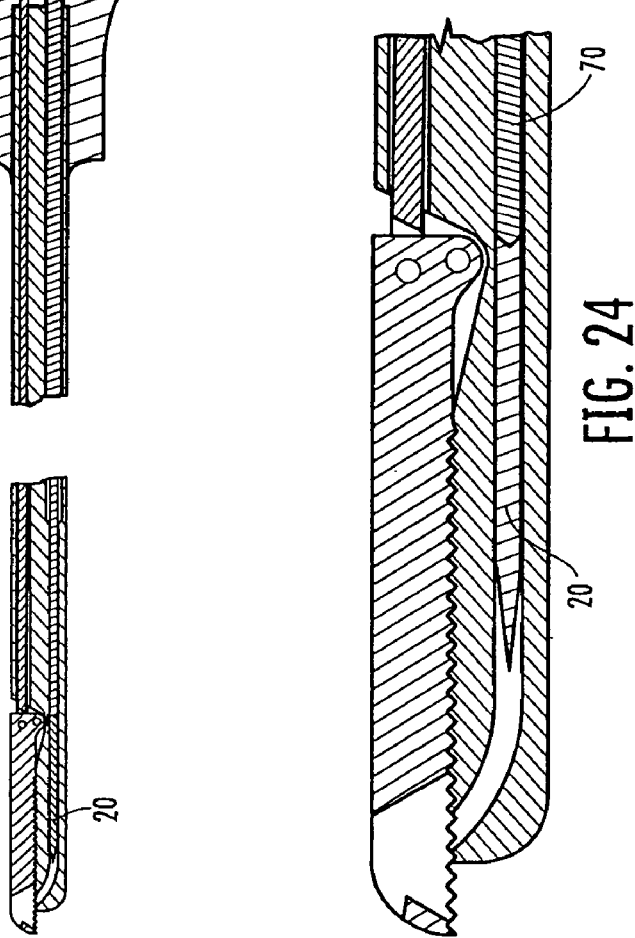
FIG. 24 is an expanded view of the distal portion of FIG. 23.

Referring to FIGS. 23 and 24, when prepared for use, needle 20 is inserted laterally into section 45 of passage 40 with the lateral surface 30 with suture 31 facing the open side of channel 40 and suture 31 extending from elongated section 18 of body 11. After insertion, needle 20 is moved distally to section 47 of channel 40; trocar 70 is inserted into channel 40 of instrument body 11, and positioned as shown in FIGS. 23 and 24.

Referring to FIGS. 25 and 26, when using the instrument to pass a suture the movable jaw 4 is opened using movable handle 8. Trocar 70 is inserted into instrument body 11 until trocar distal end 73 engages needle proximal end 21. Suture 31 carried by the needle 20 moves freely in slot 54.

Figure 30:
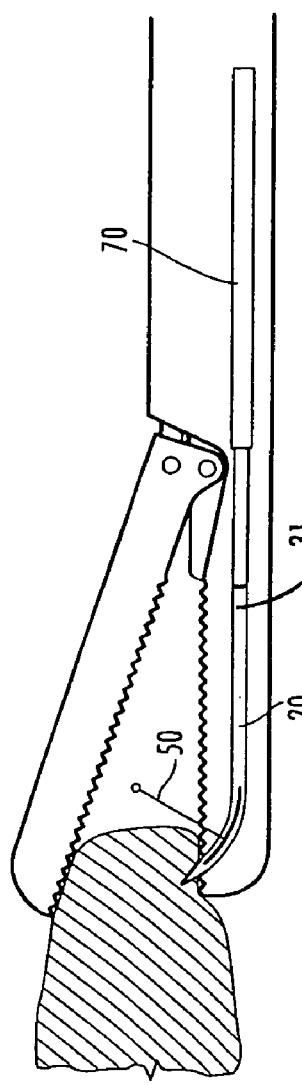
FIG. 30 is an expanded view of the distal end of the instrument shown in FIG. 29.
Figure 29:
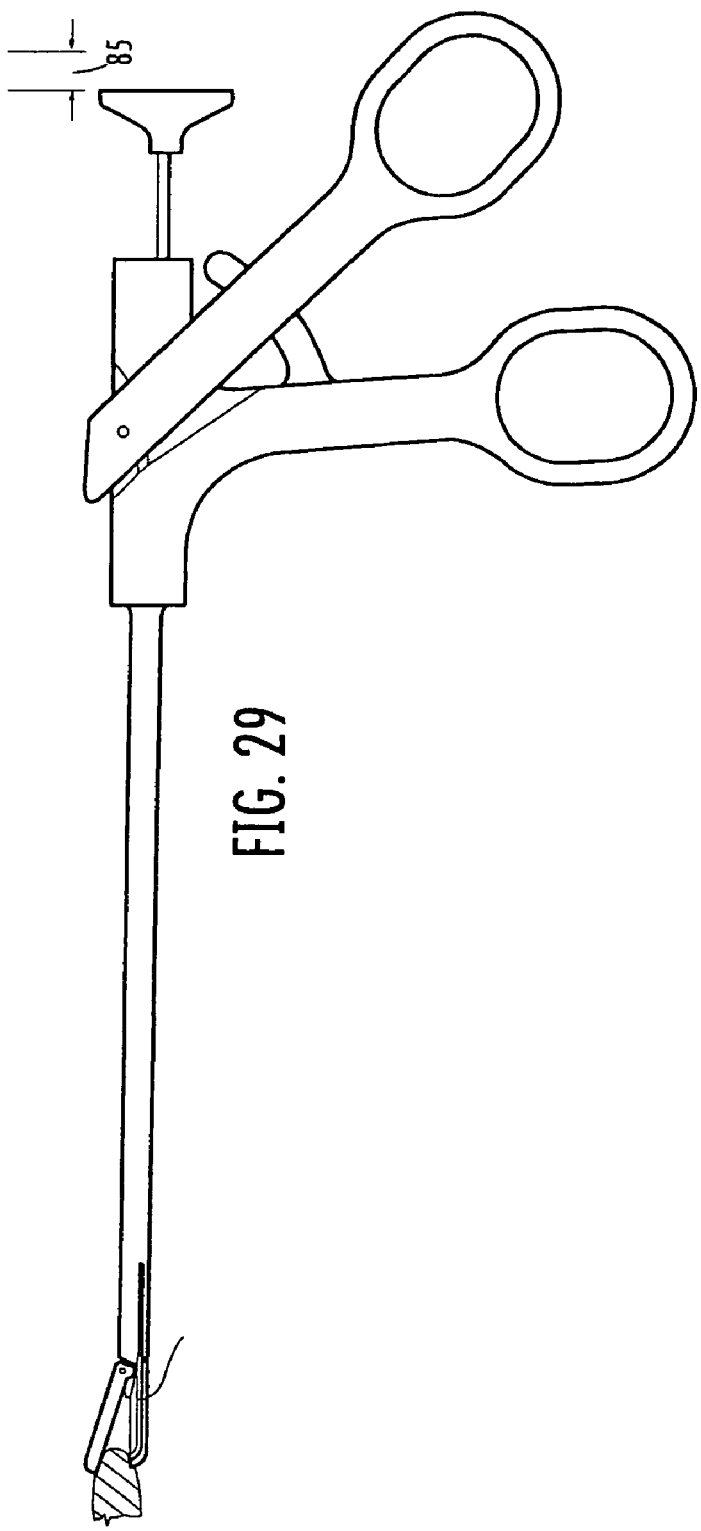
FIG. 29 shows the trocar now advanced so that the needle tip is beginning to pierce tissue grasped between the instrument jaws.

During use of the device, as seen best in FIGS. 27 and 28, tissue is grasped between upper jaw 4 and lower jaw 3. Referring to FIGS. 29 and 30, advancing trocar 70 a distance 85 distally causes needle 20 to move distally in channel 20, the distal portion of the needle being formed to a radius 50 by the radial portion 49 of passage 40.

Figure 34:
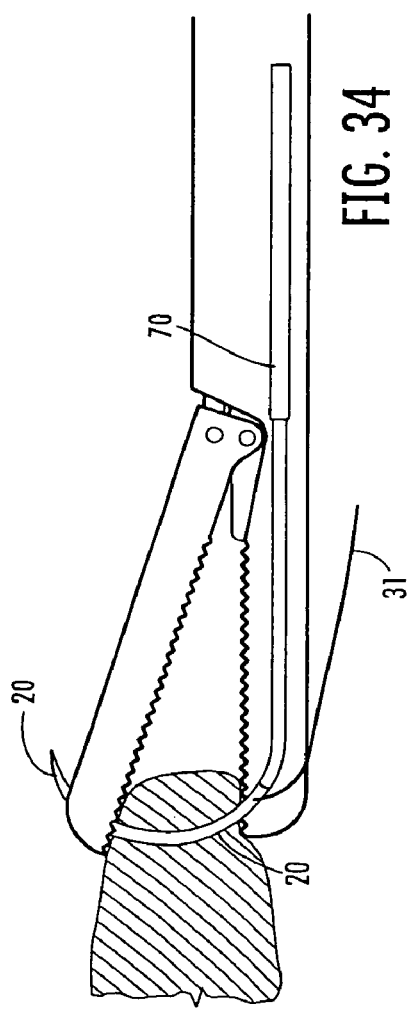
FIG. 34 is an expanded view of the distal end of the instrument of FIG. 33.
Figure 33:
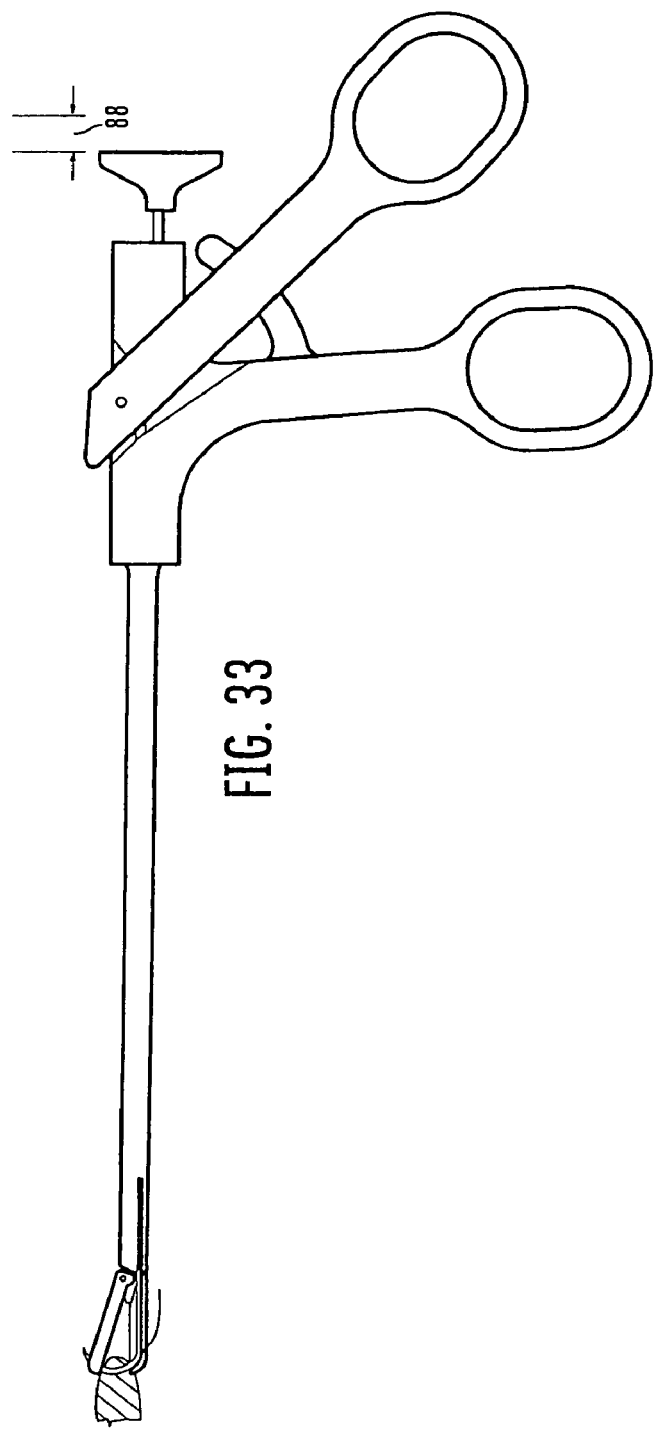
FIG. 33 shows the trocar advanced so that the needle has passed through tissue grasped between the instrument jaws and protrudes beyond the superior surface of the moveable jaw.

Referring to FIGS. 31 and 32, advancing the trocar an additional distance 86 causes needle 20 to be formed to a radial shape of radius 87, radius 87 being larger than radius 50 of section 49 of passage 40 due to spring back of the needle after leaving the passage radial section 49. Needle 20 follows a radial path through the tissue. Advancing trocar 70 an additional distance 88 (see FIGS. 33 and 34) causes needle 20 to advance along its radial path until needle distal tip protrudes above top surface 64 of movable jaw 4, having passed through jaw 4 via passage 60.

Figure 36:
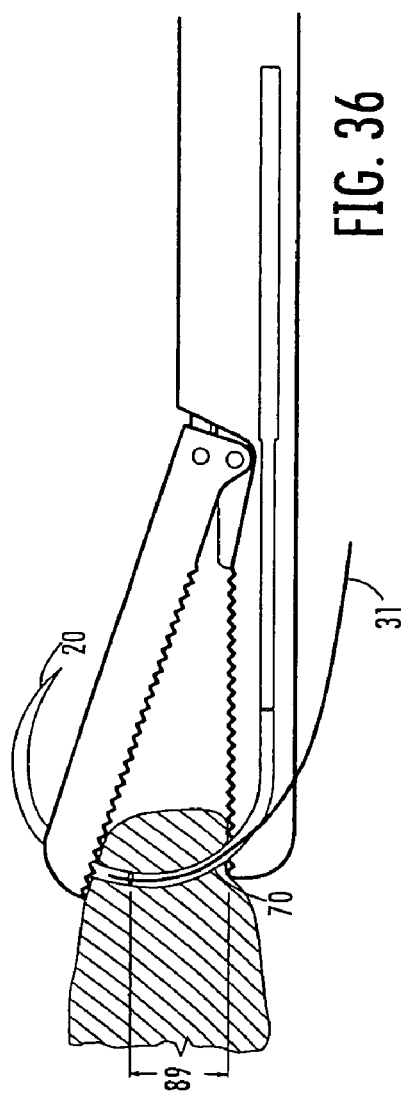
FIG. 36 is an expanded view of the distal end of the instrument of FIG. 35.
Figure 35:
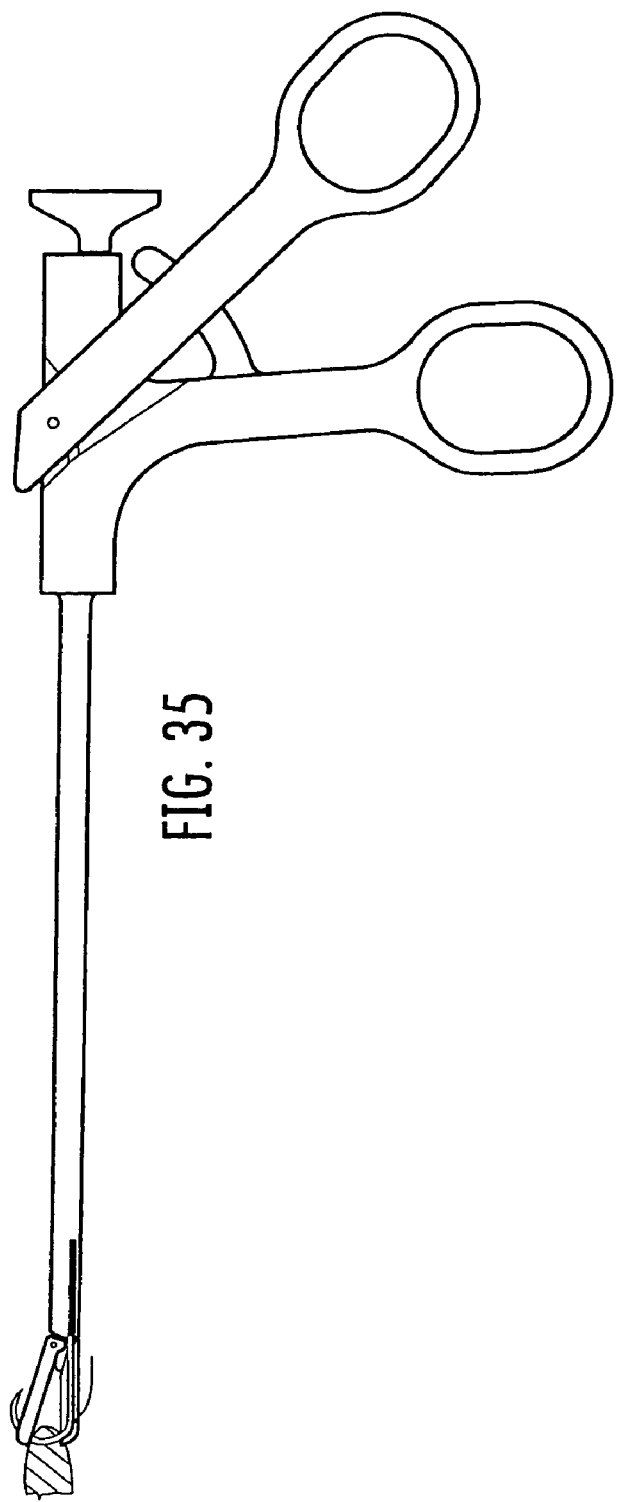
FIG. 35 shows the trocar fully advanced so that the trocar distal tip has forced the needle proximal end significantly through the tissue grasped between the instrument jaws.

As is best seen in FIGS. 35 and 36, advancing trocar 70 distally until hub 72 contacts distal face 41 of instrument body 11 advances needle 20 further through the tissue, with distal tip 73 of trocar 70 assuming a radial shape of radius 87 as it passes through radial portion 49 of passage 40. Alignment between trocar distal tip 73 and needle proximal end 21 is maintained by engagement of the needle proximal end conical recess with the with the trocar distal tip conical protrusion, needle proximal end conical radius 24 and trocar distal tip conical radius 83 being equal. In this manner, needle 20 and suture 31 are advanced a distance 89 into the tissue beyond the top surface of lower jaw 3.

Figure 38:
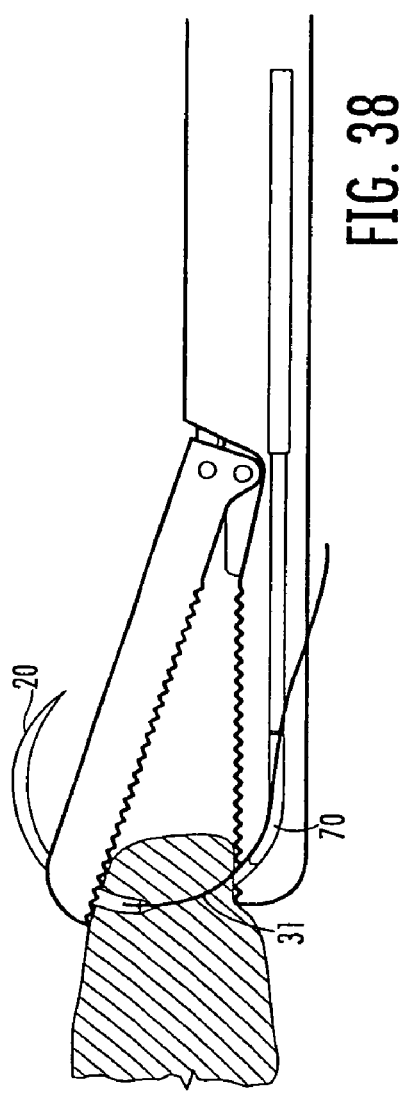
FIG. 38 is an expanded view of the distal end of the device of FIG. 37.
Figure 37:
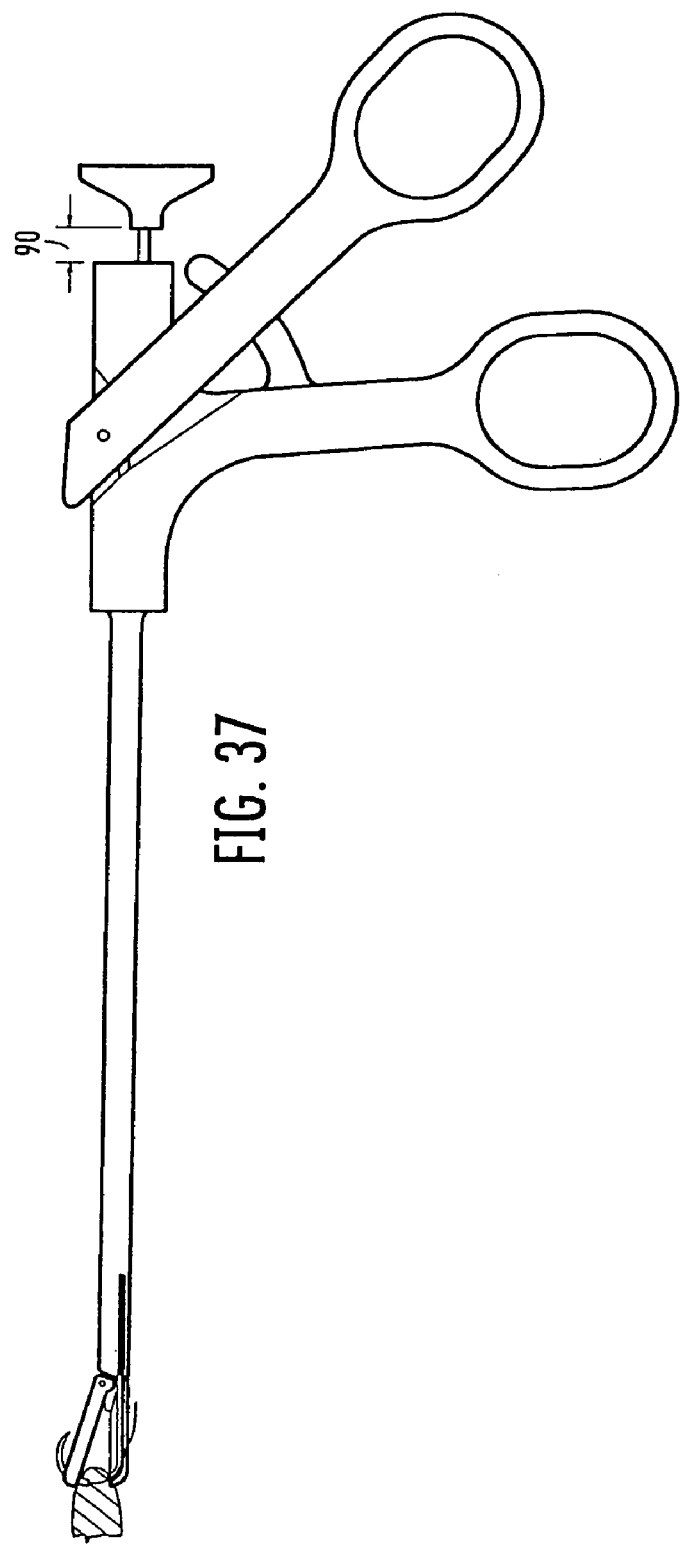
FIG. 37 is similar to FIG. 35, but with the trocar retracted so that only the needle and suture remain within the tissue.
Figure 40:
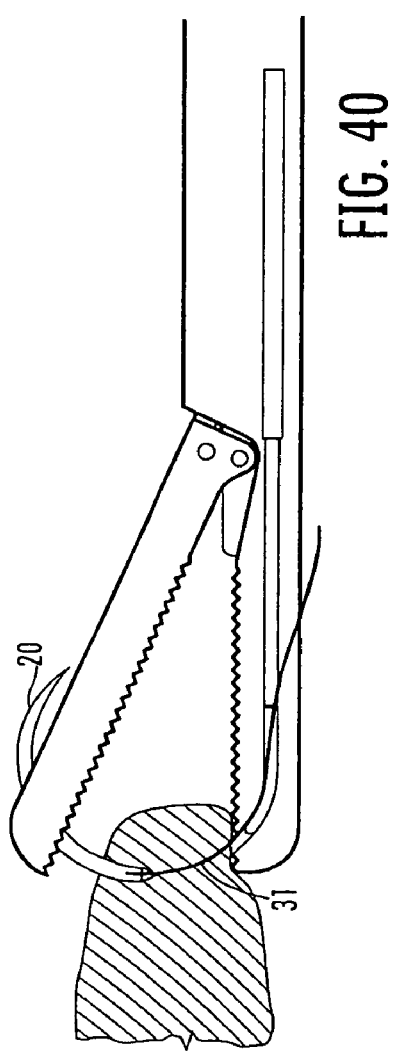
FIG. 40 is an expanded view of the distal end of FIG. 39.
Figure 39:
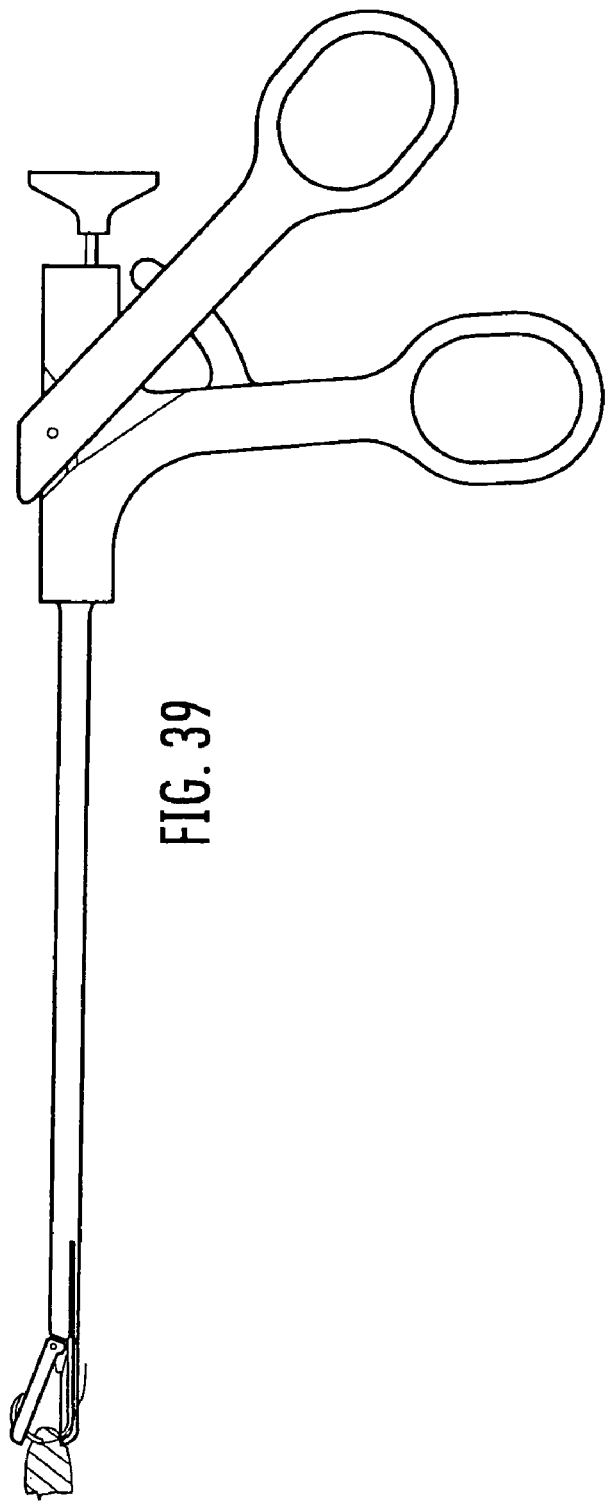
FIG. 39 is similar to FIG. 37, but with the moveable jaw retracted.
Figure 44:
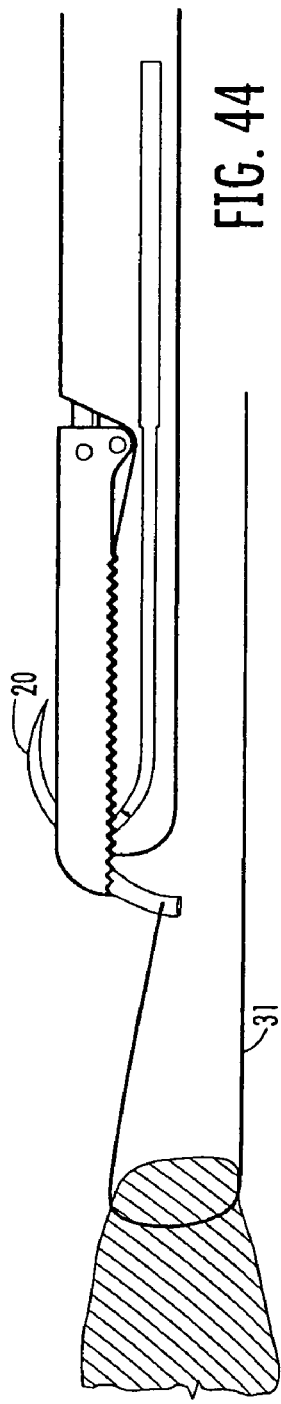
FIG. 44 is an expanded view of the distal end of FIG. 43.
Figure 43:
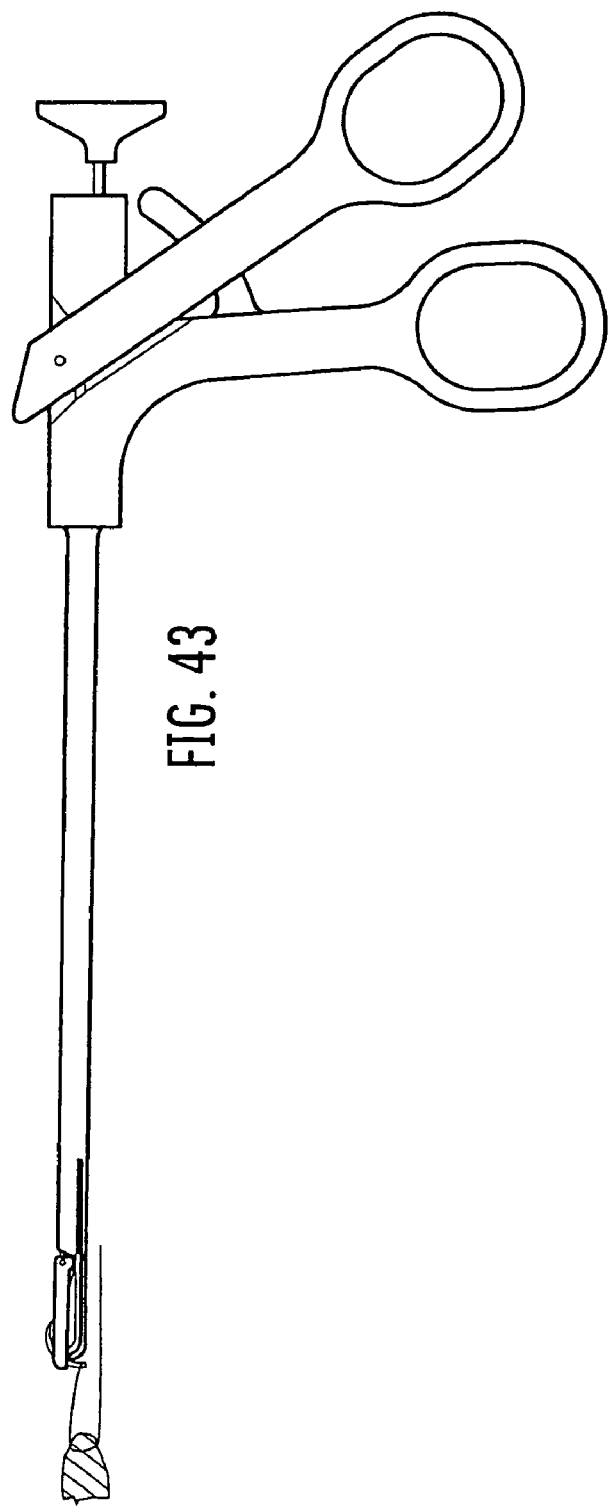
FIG. 43 is similar to FIG. 41, but with the needle grasped between the jaws of the instrument.
Figure 46:
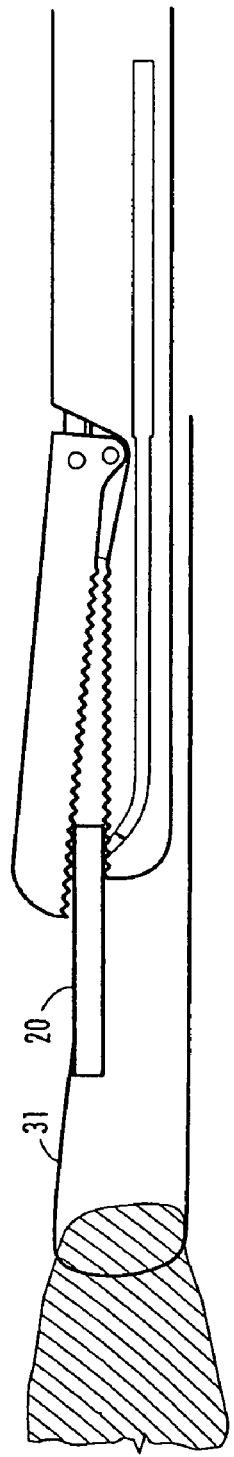
FIG. 46 is an expanded view of the distal end of FIG. 45.
Figure 45:
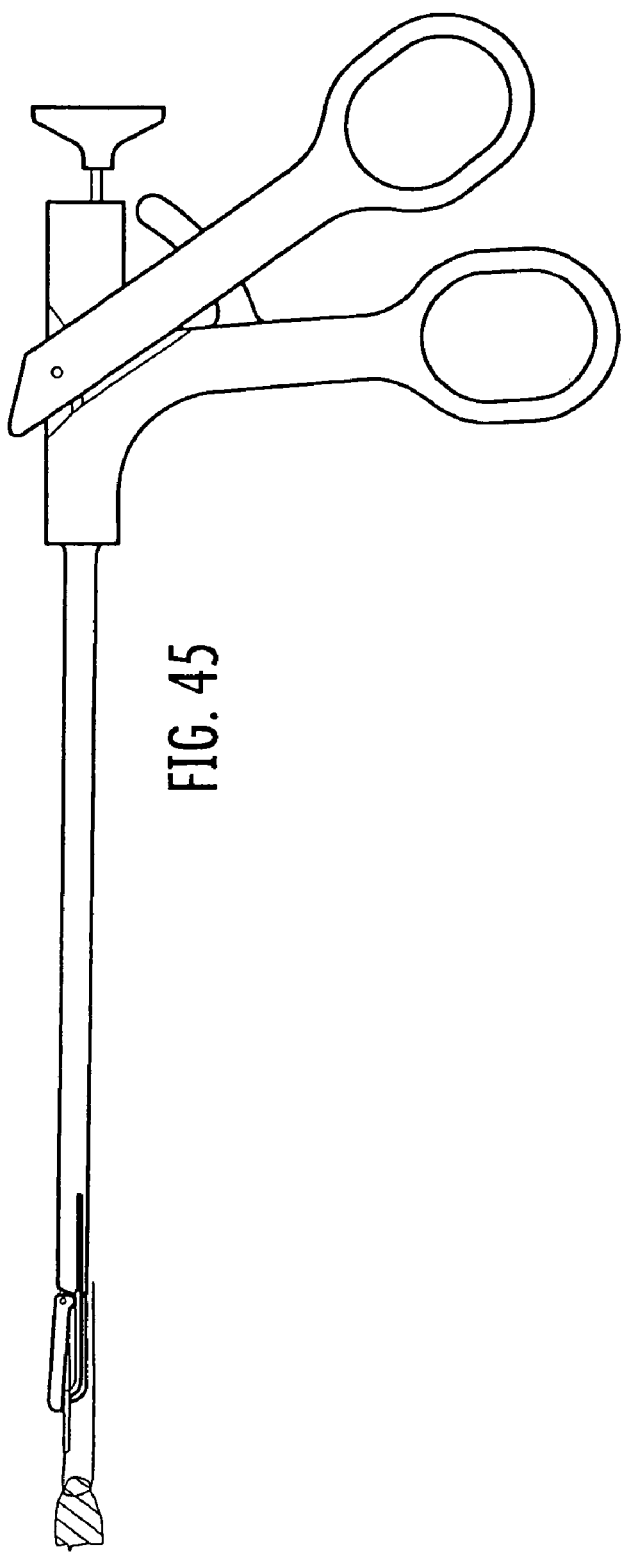
FIG. 45 is similar to FIG. 43, but with the needle rotated and grasped between the jaws in preparation for withdrawal through the cannula.

As is best seen in FIGS. 37 and 38, withdrawing trocar 70 a distance 90 causes the trocar distal tip 73 to be withdrawn from the tissue into the distal portion of passage 40, leaving needle 20 and suture 31 in the tissue, with needle distal tip 22 protruding well above the top surface of upper jaw 3. As seen in FIGS. 39 and 40, upper jaw 3 is now retracted with needle 20 moving freely within passage 60. Referring now to FIGS. 41 and 42, withdrawing the instrument axially causes needle 20 in slot 60 of upper jaw 3 to be pulled free from the tissue with suture 31 now passing through the tissue. Referring to FIGS. 43 and 44, closing jaw 3 causes it to grasp needle 20 thereby allowing further retraction of the needle and the suture. As seen in FIGS. 45 and 46, jaws 3 and 4 may be opened thereby freeing needle 20, and the needle rotated 90 degrees and re-grasped by jaws 3 and 4.

Figure 47:
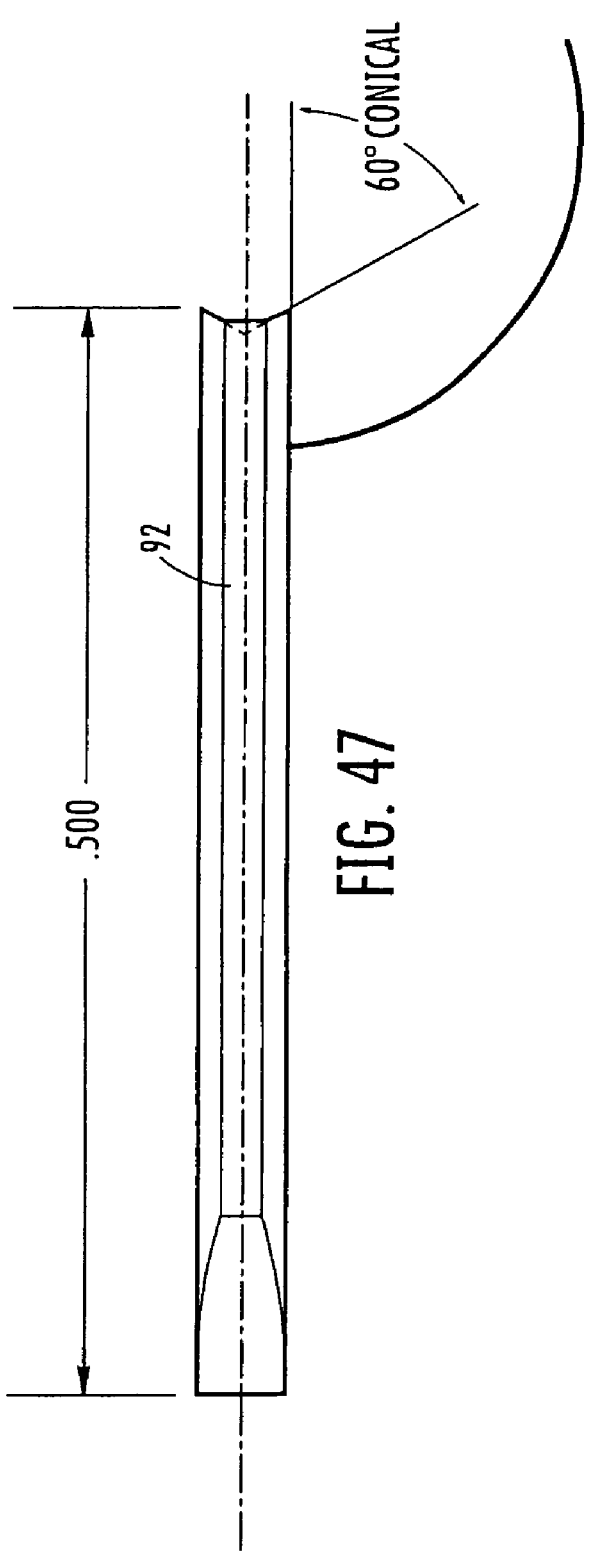
FIG. 47 is a plan view of an alternate needle configuration according to the invention.
Figure 48:
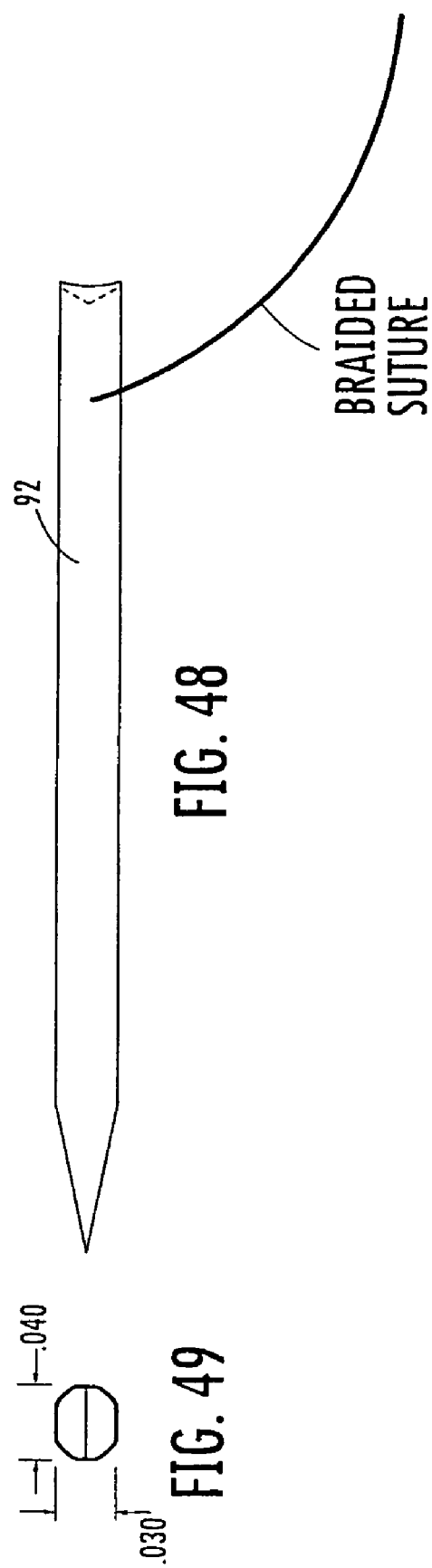
FIG. 48 is a side view of the needle configuration of FIG. 47.
Figure 49:
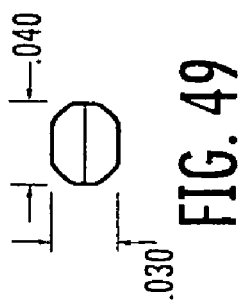
FIG. 49 is an end view of the needle configuration of FIG. 47.
Figure 47A:
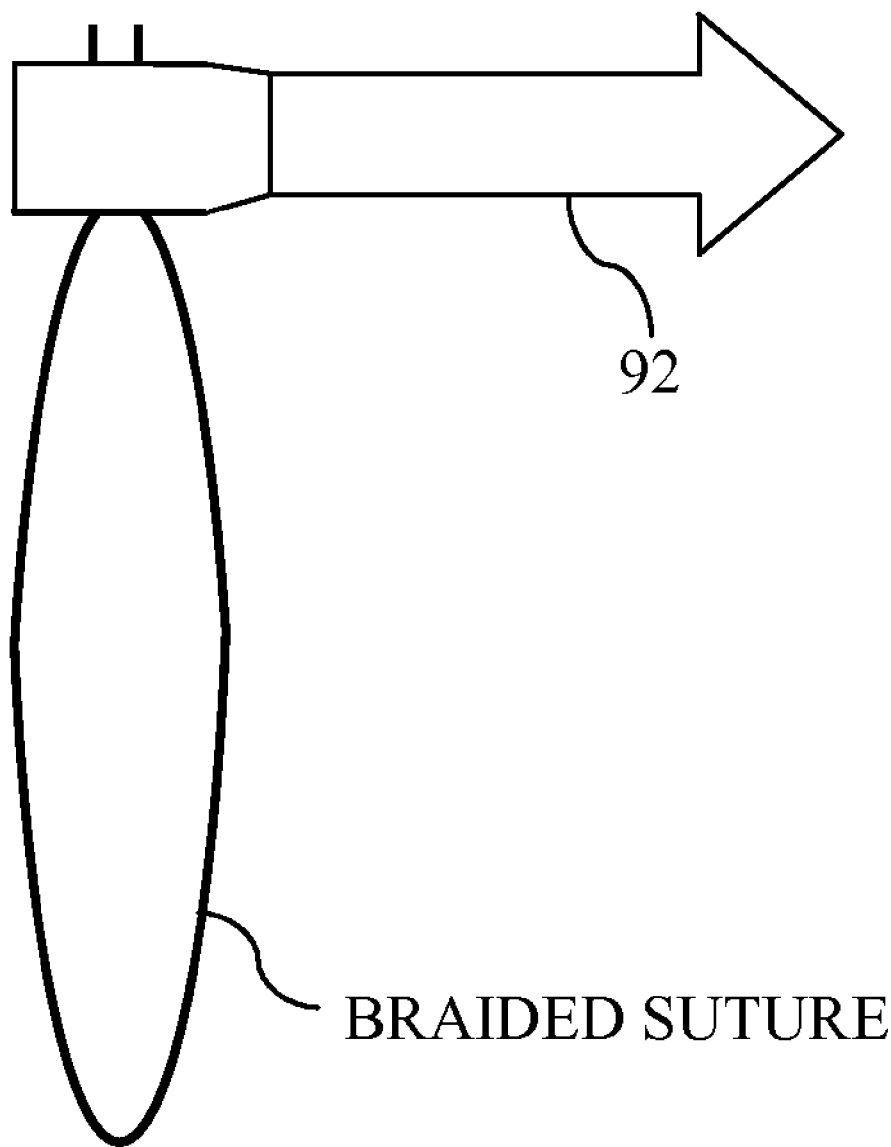
FIG. 47a is a plan view of an alternate suture configuration according to one embodiment of the invention.
Figure 53:
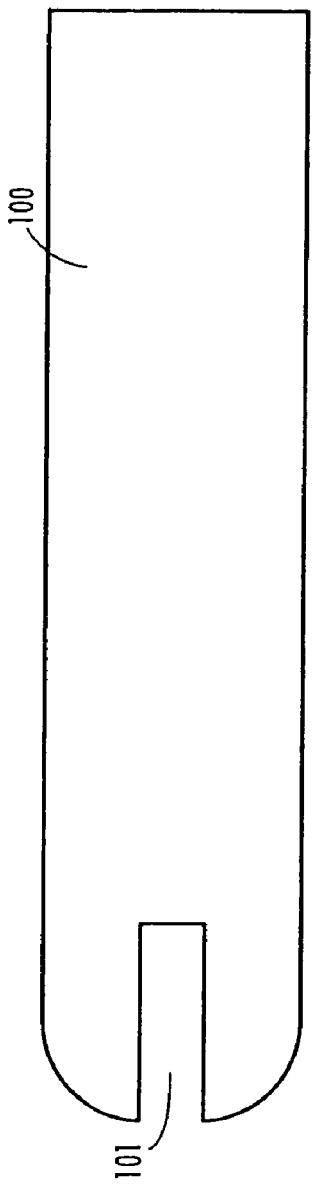
FIG. 53 is a plan view of an alternate top jaw configuration according to the invention.
Figure 54:
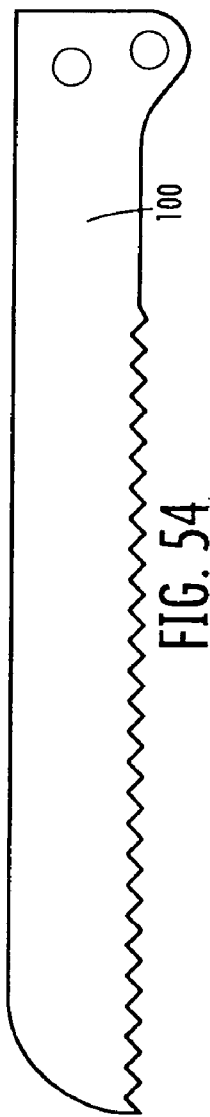
FIG. 54 is a side view of the alternate top jaw configuration of FIG. 53.
Figure 56:
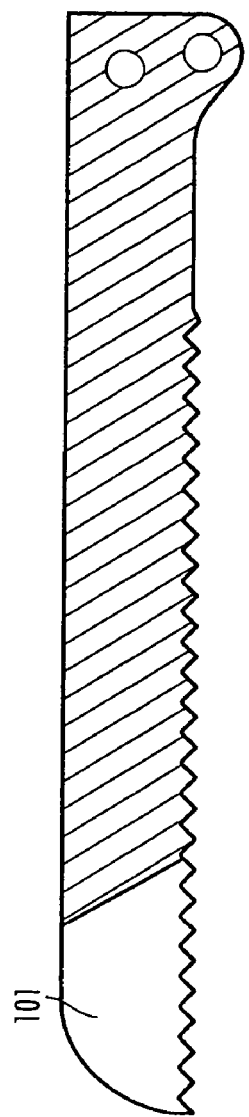
FIG. 56 is a sectional view of the alternate top jaw configuration of FIG. 53.
Figure 55:
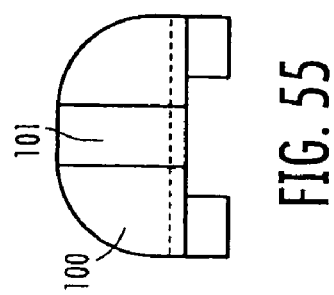
FIG. 55 is an end view of the alternate top jaw configuration of FIG. 53.

Although the above description references "needle 20," various other needle designs are equally applicable to the invention. In another embodiment, shown in FIGS. 47 through 49, needle 92 has a cross-section with two parallel sides, the lateral faces having a nearly radial profile, a shape producible by coining a cylindrical needle. Additionally, prior to delivery of the suture material, the suture material may be a standard suture or may be a smaller suture. As shown in FIG. 47a, the suture material may be looped back into the needle 92 such that when the needle 92 is delivered to the tissue, a loop of suture material is delivered that may then be used for other purposes, such as an eyelet for the transfer of other sutures.

In another embodiment, shown in FIGS. 50 through 52, needle 94 has a non-uniform cross-section, upper and lower surfaces 95 and 96 having a plurality of angled surface segments 98 of angle 95 each surface terminating in a radius 96 so as to form a series of notches useful in engaging corners of passage 60 in upper jaw 3 so as to aid in needle retraction during axial withdrawal of the instrument.

Figure 60:
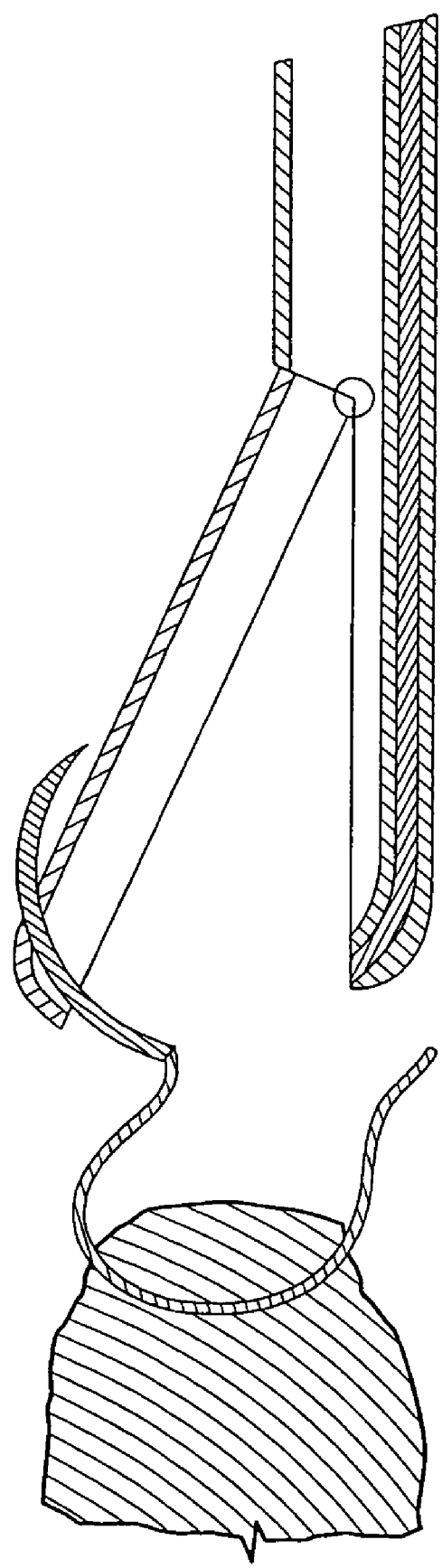
FIG. 60 is a sectional view of upper and lower jaws with jaws opened 100 percent and the suture being pulled through the tissue.

In addition to alternative needle designs, jaw construction is likewise variable in accordance with the invention. In another embodiment, best seen in FIGS. 53 through 56, upper jaw 100 is of similar construction to upper jaw 3 except that passage 60 has been replaced with slot 101. As is best seen in FIGS. 57 through 59, the distal protrusion 62 of upper jaw 4 beyond lower jaw 3 is required to allow needle 20 to enter passage 60 throughout the range of positions of upper jaw 4. FIG. 60 is a sectional view of upper and lower jaws with jaws opened 100 percent and the suture being pulled through the tissue.

Figure 61:
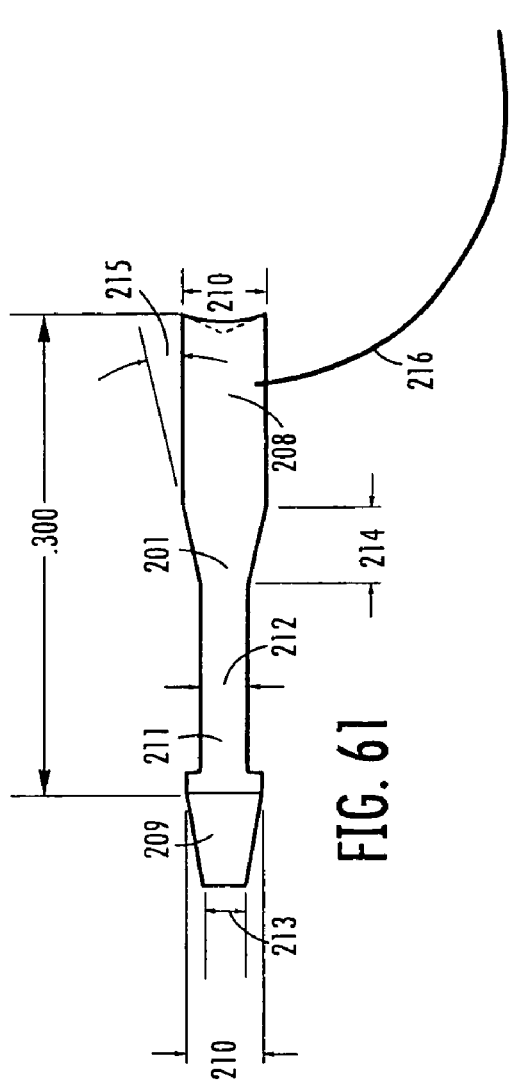
FIG. 61 is a plan view of yet a different alternate needle according to the invention.
Figure 62:
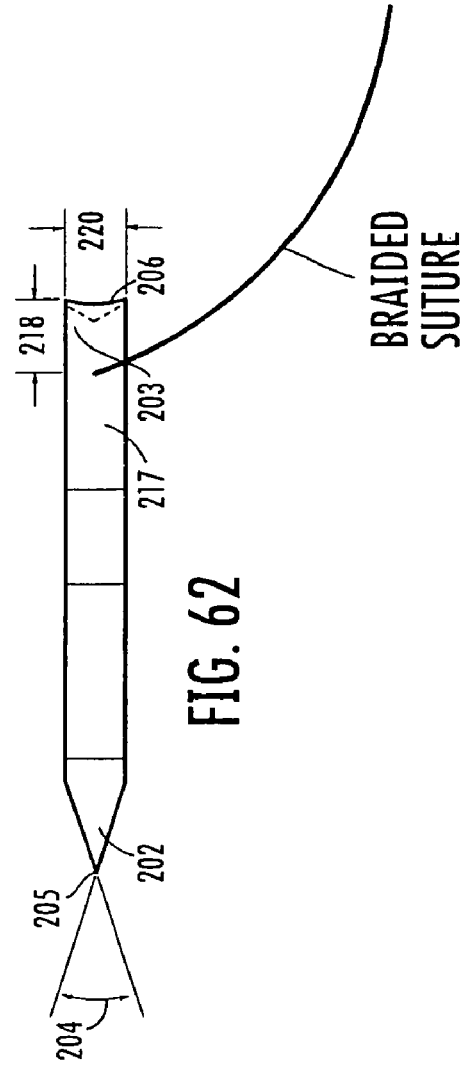
FIG. 62 is a lateral side view of the different alternate needle of FIG. 61.
Figure 63:
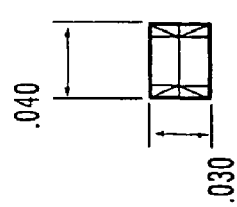
FIG. 63 is an end-on view of the alternate needle of FIG. 61 viewed from the distal tip.

A further alternate needle 201 is shown in FIGS. 61 through 63. As is best seen in FIG. 62, the needle of thickness 220 has a distal end 202 and a proximal end 203, with the distal end formed to a wedge shape having included angle 204 so as to form a cutting edge 205. The proximal end 203 has a conical shape 206 formed therein and having an angle 207 equal to angle 83 on the distal tip of trocar 70 shown in FIGS. 18 through 22. As is best seen in plan view FIG. 61, needle 201 has three sections distinguished by their width. Proximal section 208 and distal section 209 have a width 210, while medial section 211 has a width of 212 than width 211. Distal section 209 is not of constant width, but rather tapers to a width 213 at its distal tip. The transition from middle section 211 to proximal section 208 is a taper of length 214 and angle 215. Suture 216 is connected to lateral surface 217 of proximal section 208 a distance 218 from proximal end 203.

An alternate upper jaw to be used in conjunction with alternate needle 201 is shown in FIGS. 64 through 71. As is best seen in FIGS. 64, 66 and 68, upper jaw 110 is constructed like upper jaw 4 having a distal end 111 and a proximal end 112, except that upper jaw 110 has a distal end slot 113, the distal slot having a proximal portion 114 and a distal portion 120, and the portions being distinguished by their width. Proximal portion 114 has a length 125 and a width 115 which is slightly larger than width 210 of proximal section 208 and distal section 209 of needle 201 as shown in FIG. 61. Distal portion 120 has a width of 121 which is slightly larger than width 212 of middle section 211 of needle 201 shown in FIG. 61.

As is best seen when viewing jaw 110 laterally as in FIG. 65, distal portion 111 of jaw 110 has a hooked portion 126 formed therein, the hooked portion having a radius 127 and a height 128, height 128 being somewhat larger than thickness 220 of needle 201 as seen in FIG. 62. As is best seen in axial sectional view FIG. 71, proximal portion 114 of slot 113 has a portion 130 of height 131 with parallel sides and a portion 132 of height 133 whose lateral facing sides are angled outward at angle 134 so that the bottom of the slot is wider than the top of the slot.

Figure 72:
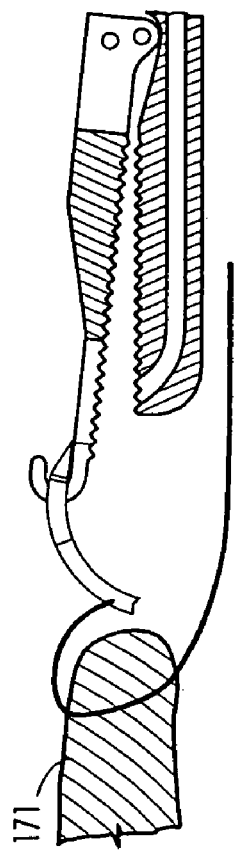
FIG. 72 is a sectional view of the upper jaw of FIG. 64 assembled to the lower jaw and with the needle of FIG. 61 deployed in tissue and ready for retrieval.

The functioning of alternate needle 201 and alternate jaw 110 is best seen in FIG. 72 through 75. Functioning of the needle and jaw are as explained previously except, referring to FIG. 72, needle 201 being of a shorter length than that of needle 20 and trocar 170 being of a shorter length than trocar 70, when trocar 70 is fully inserted to the limit of its travel, the portion of needle 201 remaining within tissue 171 is greater than that remaining in the previously explained embodiments. The length 175 of the portion of needle 201 protruding beyond tissue 171 is sufficient to cause the distal end of medial portion 211 of needle 201 to extend above surface 172, needle 201 having passed through proximal portion 114 of slot 113, and, as shown in FIG. 72 passed into distal portion 120 of slot 113 due to movement of the instrument proximally.

Figure 73:
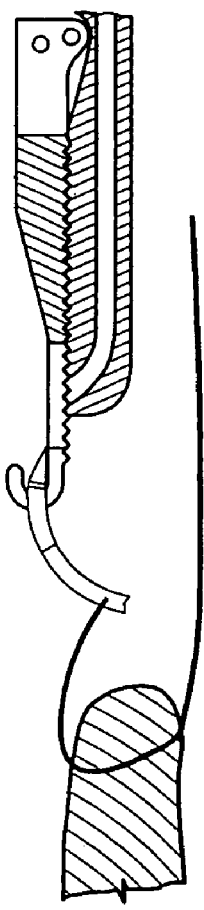
FIG. 73 is a sectional view of the upper jaw of FIG. 64 assembled to the lower jaw and with the needle of FIG. 61 captured in the upper jaw.
Figure 74:
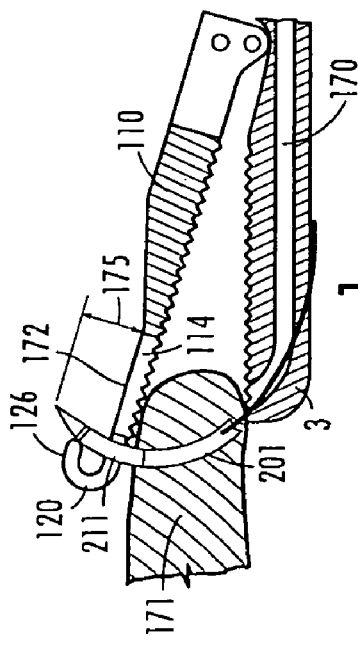
FIG. 74 is a sectional view of the upper jaw of FIG. 64 assembled to the lower jaw and with the needle of FIG. 61 captured in the upper jaw and withdrawn from the tissue.
Figure 75:
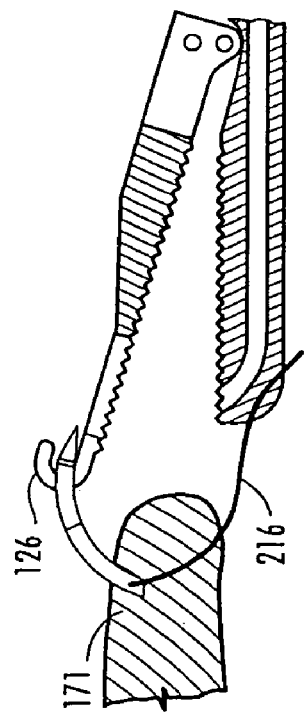
FIG. 75 is a sectional view of the upper jaw of FIG. 64 assembled to the lower jaw and with the needle of FIG. 61 captured by the instrument and positioned for withdrawal through a cannula.

In this embodiment, needle 201 is prevented from disengagement from the distal portion 120 of slot 113 because the width 210 of needle distal portion 209 is greater than width 121 of slot distal portion 120. Needle 201 is able to move freely within slot 113 parallel to the axis of the slot as width 212 of needle medial portion 211 is less than width 121 of distal portion 209 of slot 113. Referring to FIG. 73, withdrawing the instrument proximally causes needle 201 to move distally and pivot within distal portion 120 of slot 113 so as to engage with the hook segment 126 of jaw 110, thereby allowing needle 201 to be extracted from tissue 171, causing suture 216 to be pulled through the tissue. As is best seen in FIG. 74, after needle 201 is free of tissue 171 upper jaw 110 may be closed and additional suture pulled through the tissue. As seen in FIG. 75, jaw 110 may be closed totally thereby allowing needle 201 and suture 216 to be withdrawn through a cannula.

Figure 77:
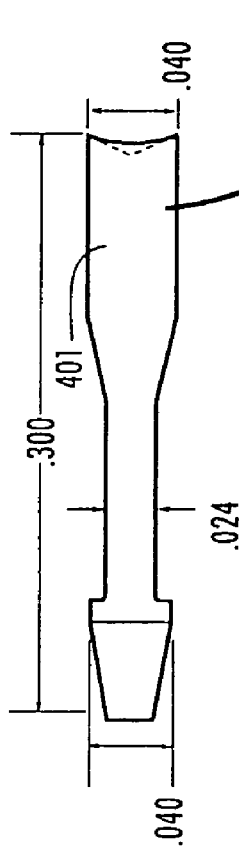
FIG. 77 is a plan view of the needle of FIG. 76 prior to forming.
Figure 76:
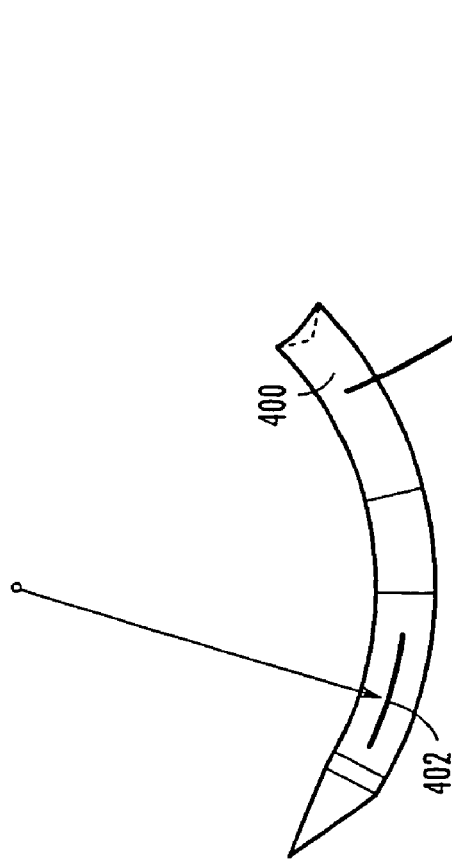
FIG. 76 is an alternate needle having a radial shape and made of Nitinol.
Figure 78:
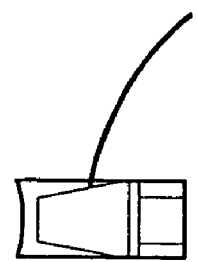
FIG. 78 is an end view of the needle of FIG. 76.

An alternate needle made of Nitinol and formed to a radial shape during manufacture is shown in FIGS. 76 through 78. Manufacture of needle 400 is accomplished in two steps, namely the cutting of the needle blank profile 401 from sheet material, and forming of the needle to a shape having radius 402, with radius 402 being equal to forming radius 50 of lower jaw 3 as shown in FIG. 10. Needle 400 may be used in the same manner as previous embodiments as it will be constrained in a straightened state by channel 47 (FIG. 9) prior to deployment. Needle capture and retrieval are accomplished in the same manner as needle 201 described previously and shown in FIGS. 72 through 75. Conversely, a Nitinol needle may be used having a linear shape, which is constrained into the radial shape as the needle passes through the radius of the lower jaw 3. Additionally, in other embodiments, a smaller Nitinol needle, i.e. having a smaller diameter, may be used for creating a looped suture in the tissue wherein the smaller needle creates a loop in the suture material as it is delivered due to the reduced diameter of the needle.

Figure 79:
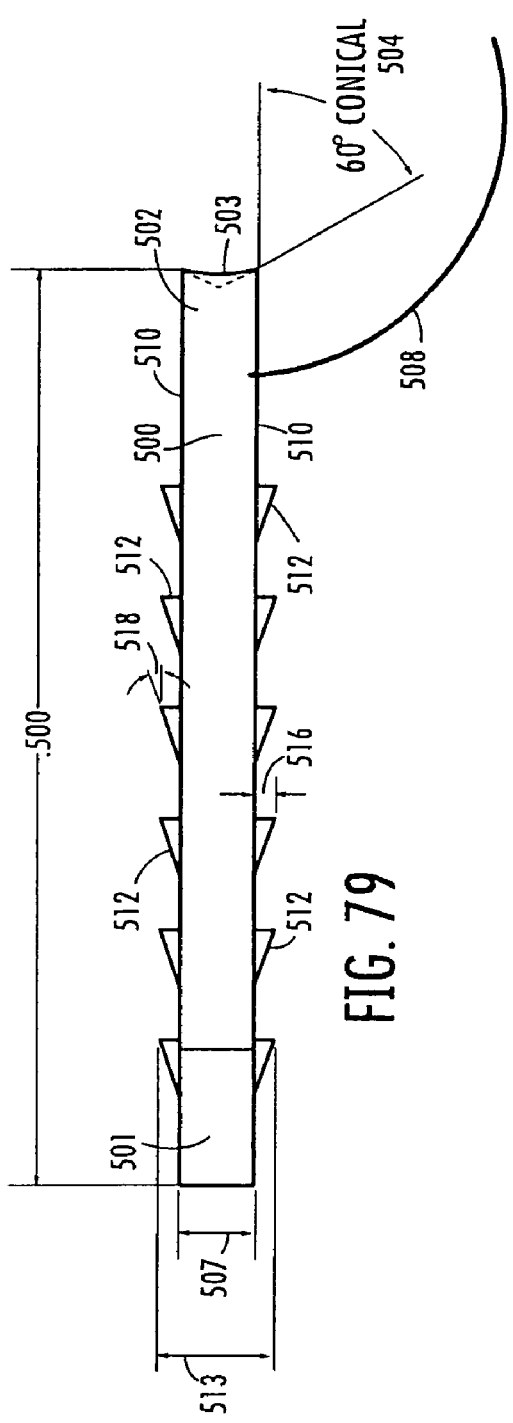
FIG. 79 is a plan view of an alternate needle according to the invention.
Figure 80:
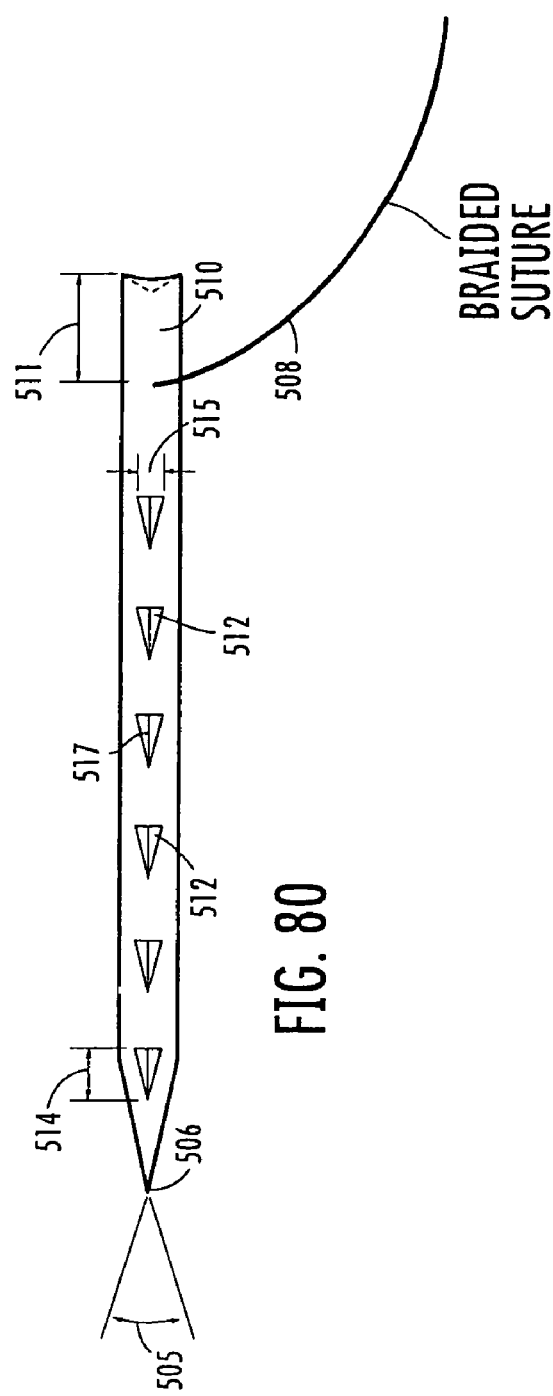
FIG. 80 is a side view of the needle of FIG. 79.
Figure 81:
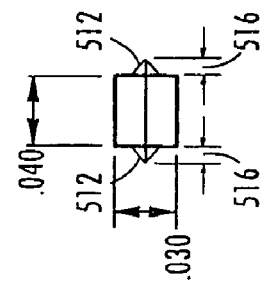
FIG. 81 is an end view of the needle of FIG. 79.

An alternate needle 500 having multiple "barbs" displaced along its lateral surfaces is shown in FIGS. 79 through 81. The needle features a distal end 501 shaped to a cutting edge 506 having included angle 507, and a proximal end 502 having a convex conical shape 503 with conical angle 504. The conical angle is, in one embodiment, equal to distal tip angle 83 of trocar 70, shown in FIG. 21. Suture 508 is attached to a lateral face 510 a distance 511 from distal end 502. Needle 500 has a width 507 and a number of pyramid-shaped "barbs" 512 displaced along lateral surfaces 510, the lateral distance 513 between barb tips being greater than width 507. The barb protrusions are pyramidal in shape having a length 514, width 515 and height 516, the distal edge 517 forming an angle 518 with the lateral surface 510.

FIGS. 82 through 86 show an alternate upper jaw for use with needle 500. Jaw 600 in constructed in the manner of jaw 4, except that jaw 600 includes a hollow structure of wall thickness 602 forming a capture space 601. The capture space 601 is defined by the walls of the jaw and by the inner surface 603 of the jaw lower wall 604. Jaw lower wall 604 has a slot 605 of width 606, width 606 being greater than width 507 of needle 500, but less than distance 513 between barb tips of needle 500. The lower section of slot 605 is tapered outward so as to aid needle 500 in entering slot 605.

Needle 500 and upper jaw 600 are used in the same manner as needle and jaw configurations previously disclosed; that is, needle 500 is formed to a radial shape by the instrument, passes through tissue confined by pressure from the upper and lower jaws, and enters the upper jaw where it is captured for retrieval. Needle 500 and jaw 600 vary in the method of capture. Distal tip 501 of needle 500 enters slot 605 of jaw 600, and via the slot enters space 601. Slot 605, being less in width than distance 513 between the needle barb tips, causes the barb tips to deform as they pass into space 601 via slot 605. Also, because wall thickness 602 is rather thin, jaw 600 will spread slightly so as to allow the barbs to pass. Because the barb proximal surfaces are square rather than tapered, the needle is retained in the slot.

The embodiments described thus far included a pair of jaws, beneficially a fixed jaw and movable jaw, with the later being additionally responsible for any capture of a needle having been radially deformed and passed through tissue. Although the invention has been described in terms of a fixed jaw and a movable jaw, it will be apparent to those of skill in the art of mechanical design that versions of the invention wherein both jaws move are also anticipated, assuming appropriate interaction associated with needle curvature and any capture of the needle.

Figure 87:
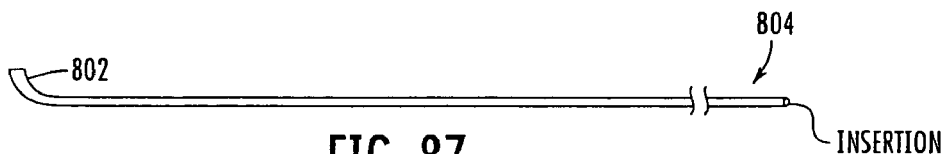
FIG. 87 is a drawing of a jawless suture punch according to the present invention.
Figure 88:
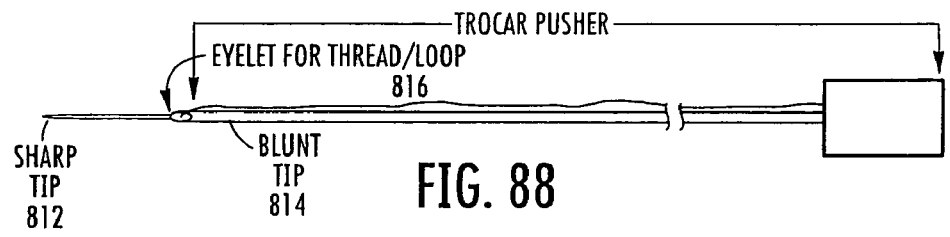
FIG. 88 is a drawing of a trocar pusher adapted for use with the jawless punch of FIG. 87.

In addition, there are situations, and embodiments of this invention, where capture is performed not by a jaw coupled to the same instrument, but rather, through the use of an additional instrument. Reference to FIGS. 87-91, which illustrate a simpler suture punch according to the invention, which is similar to the embodiments described above, but does not include an upper jaw to hold tissue and/or retain a needle once formed. Nevertheless, the same type of malleable needle according to the invention having a suture/suture loop is inserted into these simpler devices, and pushed down the channel by a pusher, which acts as the force-supplying mechanism. Since the terminal action of the needle is the same as that used with the more sophisticated device as described herein, the shaft of the channel must be stiff enough to resist a perpendicular vector force required to push the needle through the tissue. One advantage of these alternative designs is that such instruments may be used to plicate the shoulder capsule from the inside arthroscopically. FIG. 87 is a drawing of a jawless suture punch according to the invention, including a curved distal end 802, and a proximal end 804 including an insertion point 806. FIG. 88 is a drawing of a pusher adapted for use with the jawless punch of FIG. 87. The pusher includes a sharpened malleable/spring steel tip 812 coupled to a blunt 814 through an eyelet 816 to receive a thread or suture loop. In operation, the curved tip 802 is placed next to tissue to be sutured, and the sharp tip inserted into the insertion point 806. The sharp tip is then advanced with the pusher of FIG. 88 through the tissue, allowing the suture to be pulled through the tissue as well.

Figure 89:
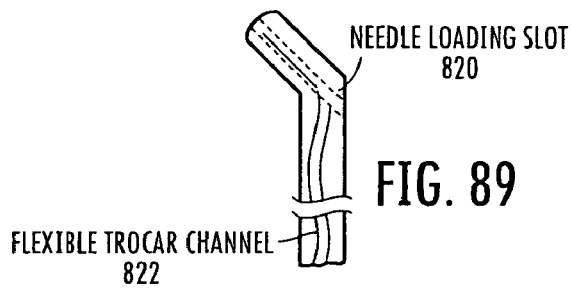
FIG. 89 is a drawing of the distal tip of an angled jaw or jaw-less design according to the present invention.
Figure 90:
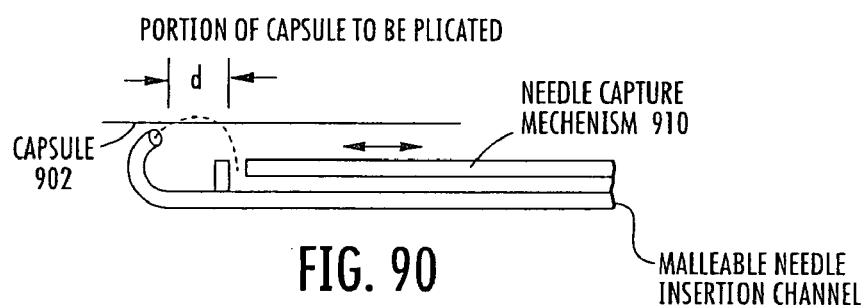
FIG. 90 is a drawing of a particularized capsular plication suture punch for the shoulder according to the present invention.
Figure 91:
FIG. 91 is a simplified drawing which shows the way in which three rigidly positioned points may be used to curve a needle into a selected radius according to the present invention.

FIG. 89 is a drawing of a lower jaw of a suture punch or a jaw-less design according to the invention. According to this embodiment, a malleable needle is inserted into a loading slot 820 such that the tip of the needle is proximate to the distal end by a distance of ⅛ inch, or thereabouts. The instrument is inserted through cannula, upon which time the tissue is grasped and a flexible trocar is pushed down trocar channel 822. As the flexible tip of the trocar nears the needle slot 820, the bend in the channel directs the tip down the needle slot, engaging the proximal end of the needle. As the trocar is advanced further, the needle is pushed through the forming section of the lower jaw, resulting in a deformation similar if not identical to the other embodiments described herein. FIG. 90 is a drawing of a particularized capsular plication suture punch for the shoulder according to the invention. Distance d indicates the portion of the capsule to be plicated, with the capsule surface being shown at 902. A malleable needle is inserted into the proximal end of the device, which penetrates into and out of the capsule, with the entire instrument remaining on one side of the surface 902. The depth of the penetration may be controlled for the curvature of the insertion channel, and the malleability characteristics of the needle. FIG. 91 is a simplified drawing which shows the way in which three rigidly positioned points may be used to curve a needle into a selected radius according to the invention. Once the needle and suture passes through the capsule, a separate needle capture mechanism 910 may be used to pull the suture through, as described elsewhere herein.

Figure 92:
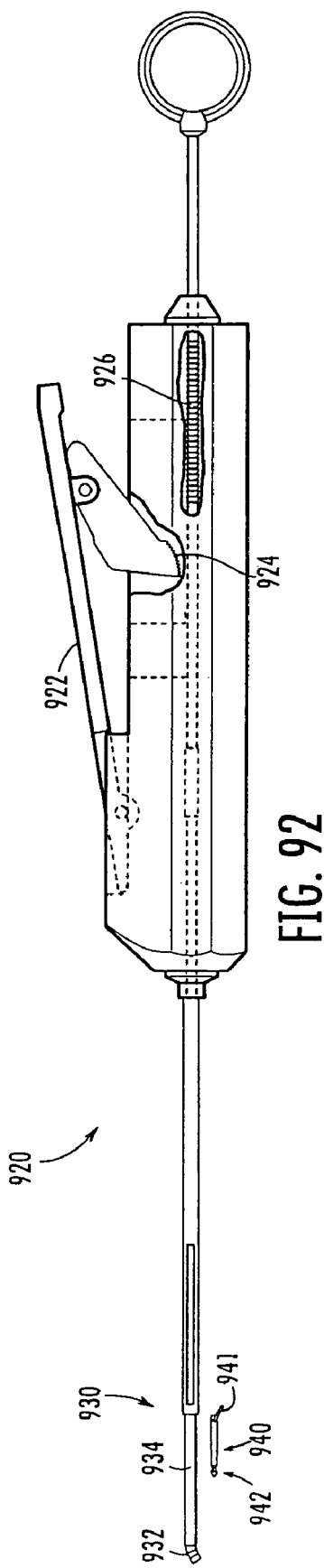
FIG. 92 is a drawing depicted in partial transparent form, illustrating a more sophisticated jawless punch according to the present invention.
Figure 93:
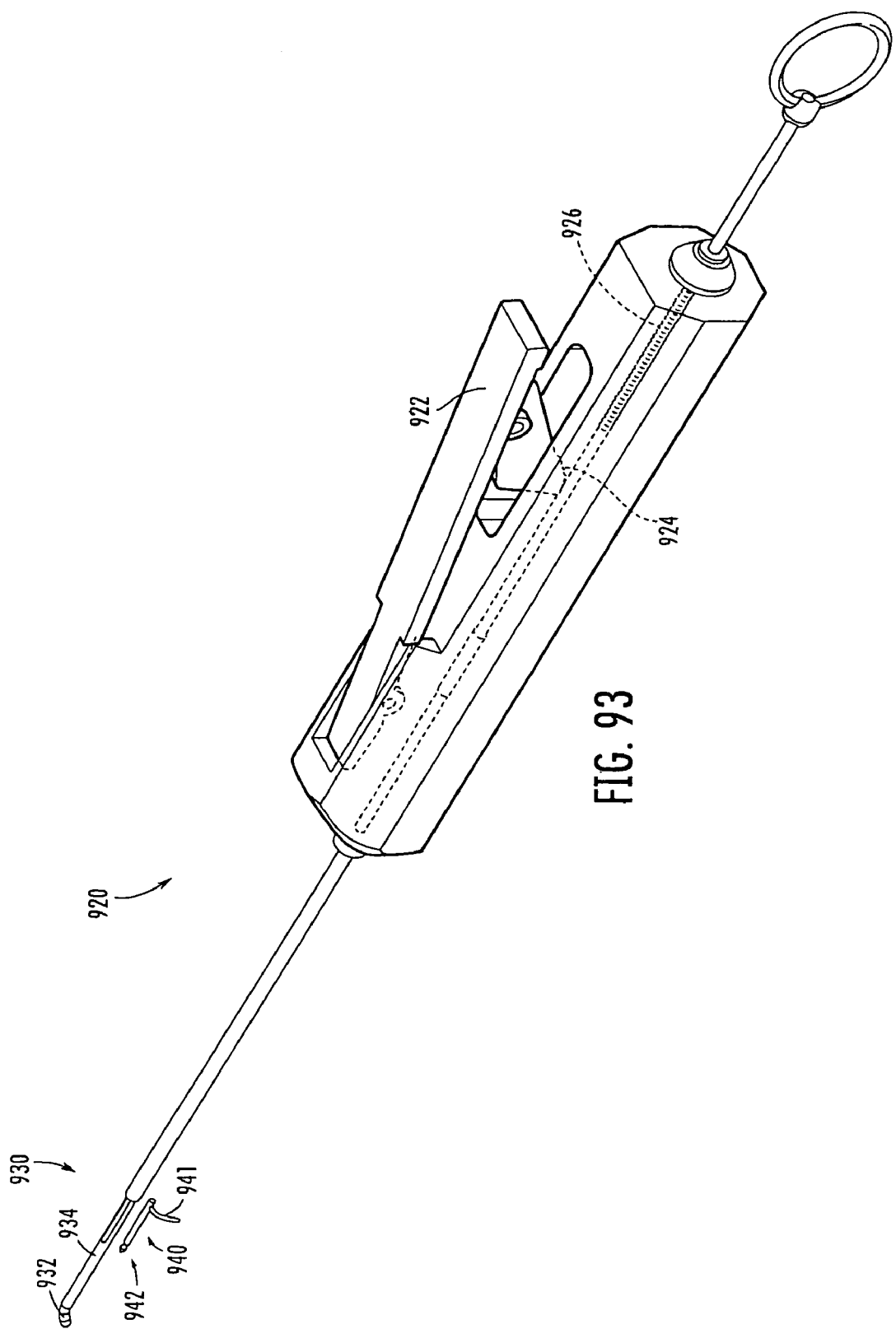
FIG. 93 is an oblique view of the device of FIG. 92.
Figure 94:
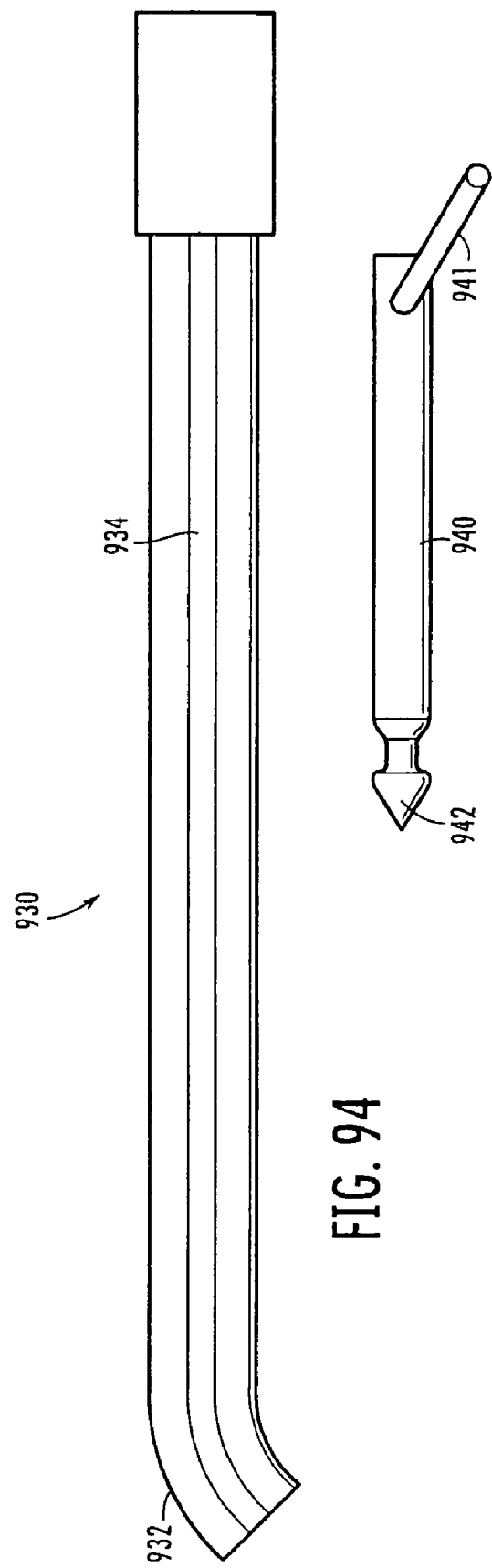
FIG. 94 is a close-up view of the distal end including the curved tip.
Figure 95:
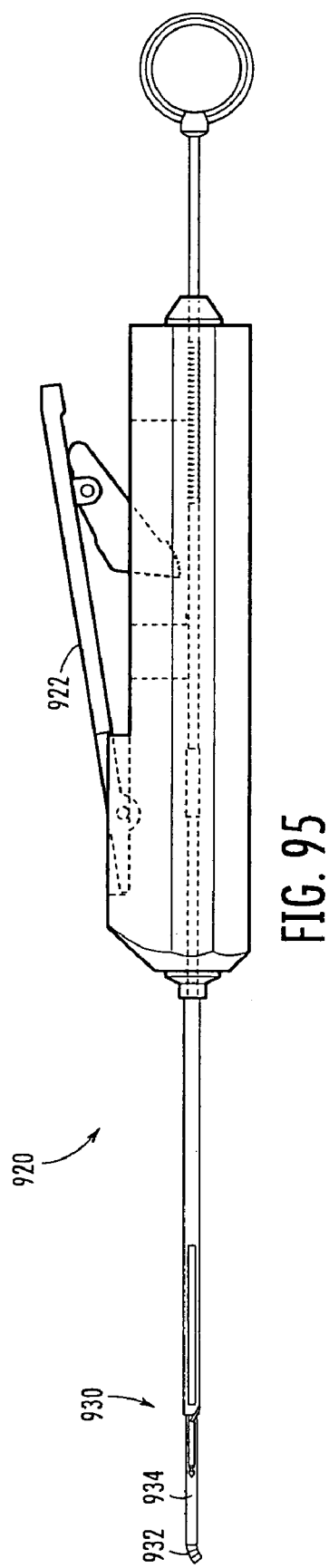
FIG. 95 is a side-view of the device of FIG. 93 with the needle loaded in position.
Figure 96:
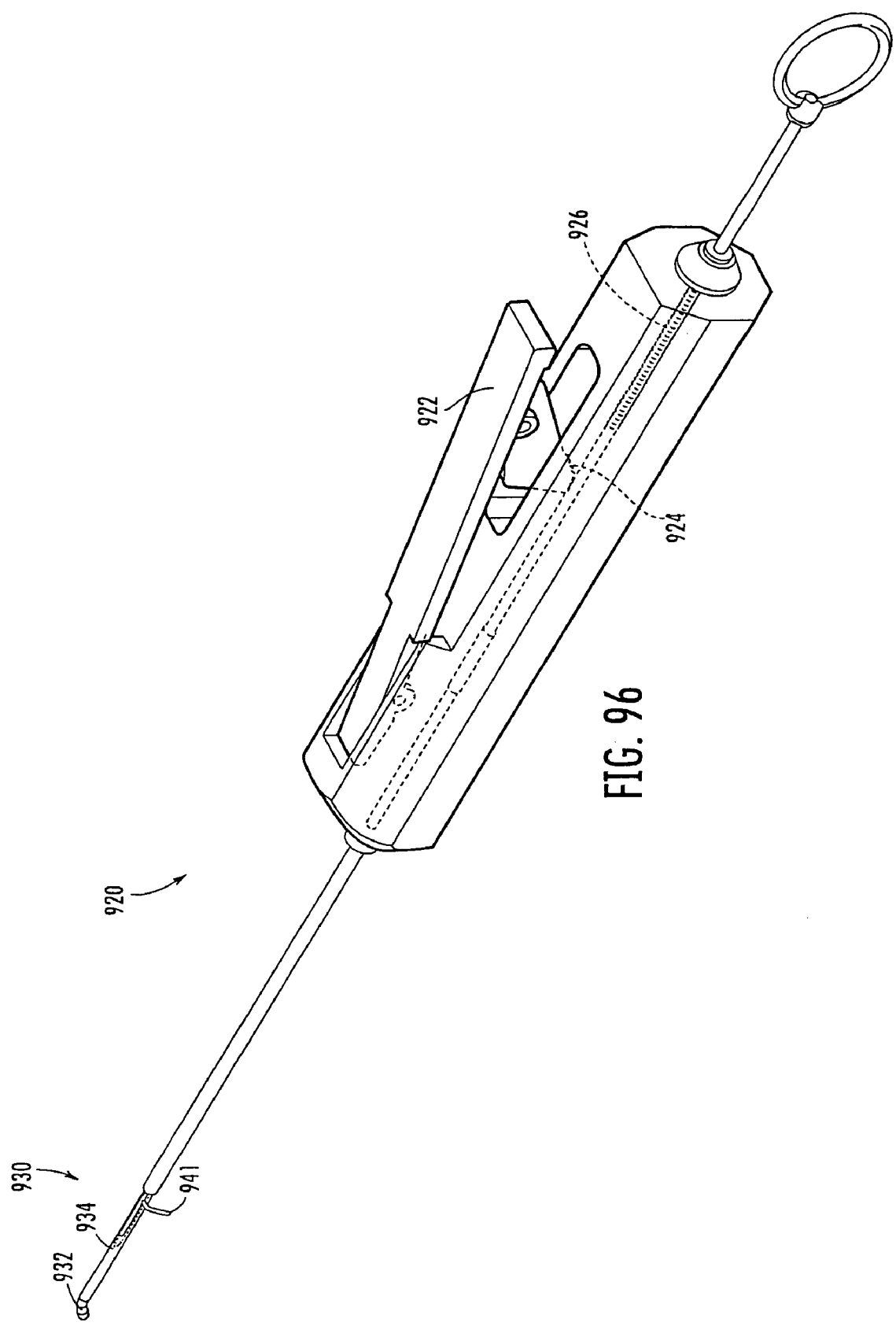
FIG. 96 is a perspective-view of the configuration shown in FIG. 95.

FIG. 92 is a drawing depicted in partial transparent form, illustrating a more sophisticated jawless punch according to one embodiment of the invention, including yet a further alternative needle including a distal tip configured for grasping with a separate instrument. The instrument depicted generally at 920 includes a body portion having a squeeze handle 922 coupled to a ratchet 924 which engages with barbs 926 on a pusher mechanism. The pusher mechanism extends through the barrel of the instrument down to the distal tip 930, which terminates in a curved portion 932, and includes a breach loading slot 934 to receive a needle 940 attached to suture 941 and including a distal tip 942 configured for grasping. FIG. 93 is an oblique drawing of the device of FIG. 92. FIG. 94 is a close-up view drawing of the distal end 930 including curved tip 932, breach loading slot 934 and specialized needle 940 having a tip 942 configured for manual grasping, the needle 940 being attached at its proximal end to suture material 941. FIG. 95 is a side-view drawing of the device of FIG. 93 with the needle loaded in position; FIG. 96 is a perspective-view drawing of the configuration shown in FIG. 95. FIG. 97 is a side-view drawing showing the trocar being advanced by pushing on the proximal end of the pusher rods. FIG. 98 is a detail drawing showing the needle being pushed passed the breached loading position, with the suture material extending out from a slot, and with the needle in position just prior to deformation. FIG. 99 is a drawing which shows the needle being deformed and pushed out the distal end, as handle 922 is compressed, causing the ratchet 924 to advance the barbs 926 on the pusher rod. FIG. 100 is a drawing which shows the needle fully advanced, now free of the distal tip of the instrument. FIG. 101 is a close-up, detail view of the needle emerging from the curved distal tip of the instrument.

Figure 103A:
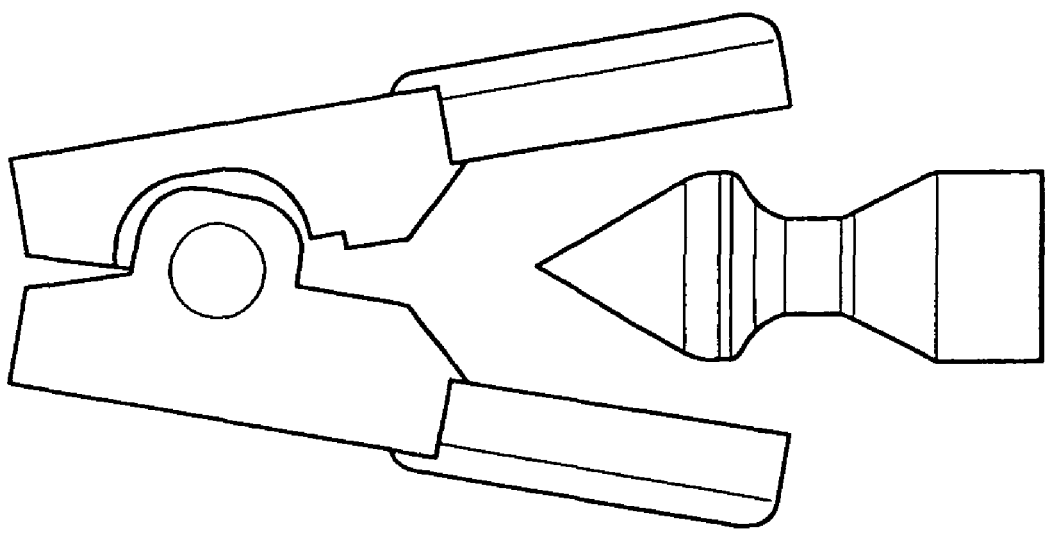
FIGS. 103A-103C are side views of the embodiments of FIGS. 102A-102C.
Figure 103B:
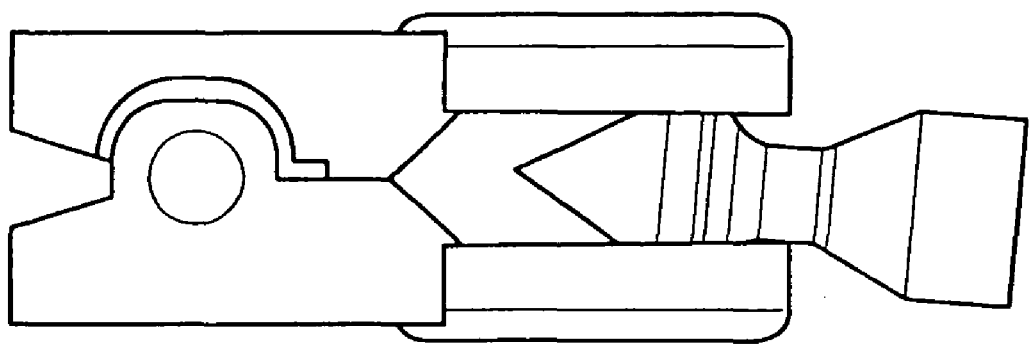
Figure 103C:
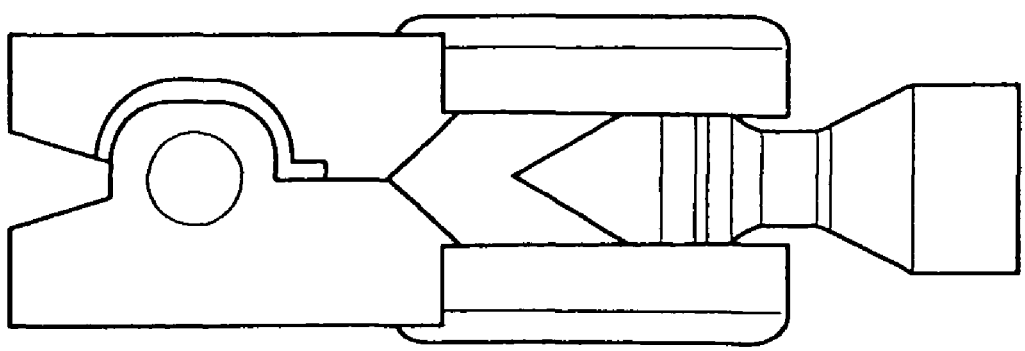
Figure 104:
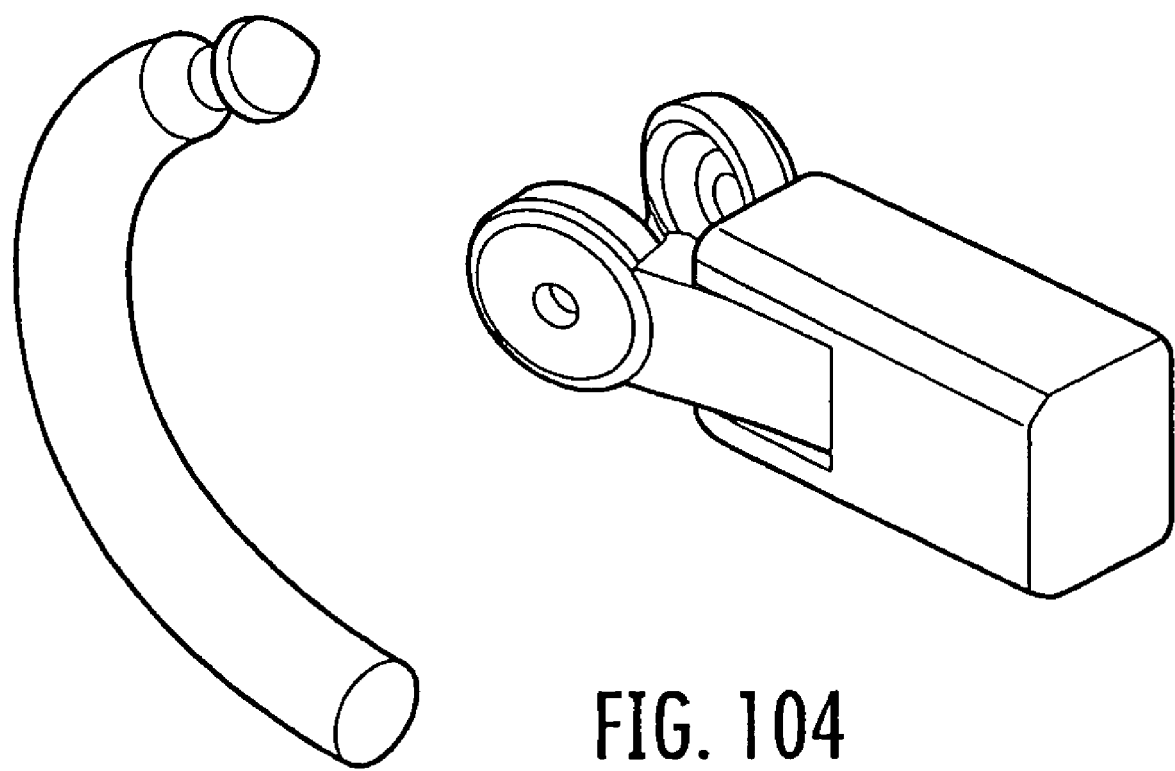
FIG. 104 is a perspective view of the grasping mechanism in conjunction with the tip of the needle.

As discussed above, with respect to the jawless embodiments of this invention, a separate instrument would generally be used to grasp the formed needle, having passed through tissue to be sutured. While conventionally available tools such as forceps, and the like, may be used for such purpose, particularly with respect to the specialized needle shown in FIG. 94 and elsewhere herein, specialized needle grasping instruments may be provided, as shown in FIGS. 102-104. FIG. 103A is a drawing which shows a grasping mechanism 1002 having a specially shaped set of jaws to capture the tip of certain needles described herein. In particular, the embodiments of FIGS. 102-104 are specially suited to grasp the tip of the needle best seen in FIG. 94. FIG. 102A shows the jaws open ready to grab the tip of the needle. FIG. 102B shows the needle grasped, and FIG. 102C shows how, even once grasped, the tip of the needle may rotate within the jaws. FIGS. 103A-103C are side views of the embodiments of FIG. 102A-102C, and FIG. 104 is a perspective view of the grasping mechanism in conjunction with the tip of the needle.

Yet a further embodiment, intended for applications such as the repair of torn meniscus, torn labrum, capsular reefing to the labrum and other applications, is described in the following text and FIGS. 105 through 109. This embodiment is different from the previous embodiments in that the distal end of the insertion instrument is configured so that the needle exits the instrument in a direction that is axial to the instrument, wherein a normal to the distal-most surface is parallel to the axis of the instrument. The needle is formed to a somewhat larger radius so that when it is fully inserted the needle tip protrudes from the upper (or lower) surface of the tissue undergoing repair, the needle being formed, in one embodiment, less than 90 degrees. When the needle is fully inserted, the insertion instrument is removed leaving the needle and suture embedded in the tissue with its distal tip exposed.

The retrieval instrument distal end is somewhat like the upper jaw of certain previous embodiments in that it has a hook shape designed to allow the captured needle to pivot freely in the plane in which it is formed. A feature allows the tool to exert a force on a needle tip in the distal as well as the proximal direction. The retrieval instrument distal end is also slotted, the slot having a width slightly greater than that of the reduced width region of the needle, but less than the width of the needle distal tip.

In use, the wedge shaped distal end of the instrument is inserted so that the reduced region of the needle is engaged by the slot in the instrument. Moving the instrument distally causes the needle to be pulled further through the tissue. When the head is fully engaged in the slot the needle is pulled the rest of the way through the tissue by moving the instrument distally a distance sufficient to free the needle from the tissue and expose a short length of suture. The retrieval instrument is then moved proximally with the needle pivoting in the distal hook so that it may be withdrawn through the cannula. After the needle is freed from the tissue, the retrieval instrument may be rotated about its axis so that the needle pivots in a plane in which there is sufficient space for this to occur.

Referring to the drawings, as best seen in FIGS. 105A through 105C, needle 2001 of width $W_1$ (2004) and height $H_1$ (2005) has a distal end 2002 and a proximal end 2003. A middle region 2009 having a width $W_2$ (2006) forms "shoulders" 2012 at its distal end 2002 which is sharpened. A suture 2007 is attached to lateral surface 2008 a distance $L_1$ (2010) from distal-most surface 2011.

Figure 106:
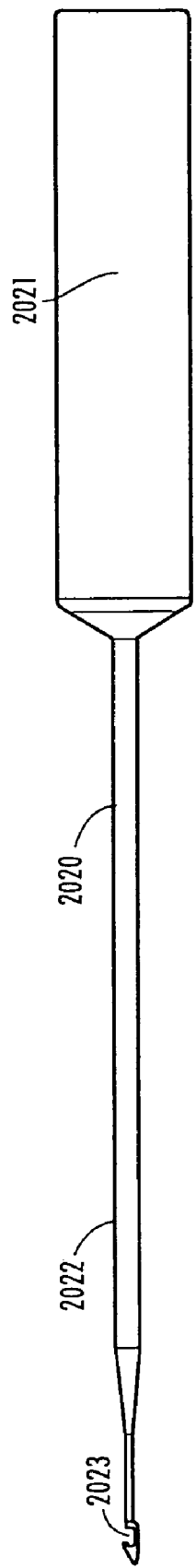
FIG. 106 is a retrieval instrument associated with the needle of FIG. 105.
Figure 107A:
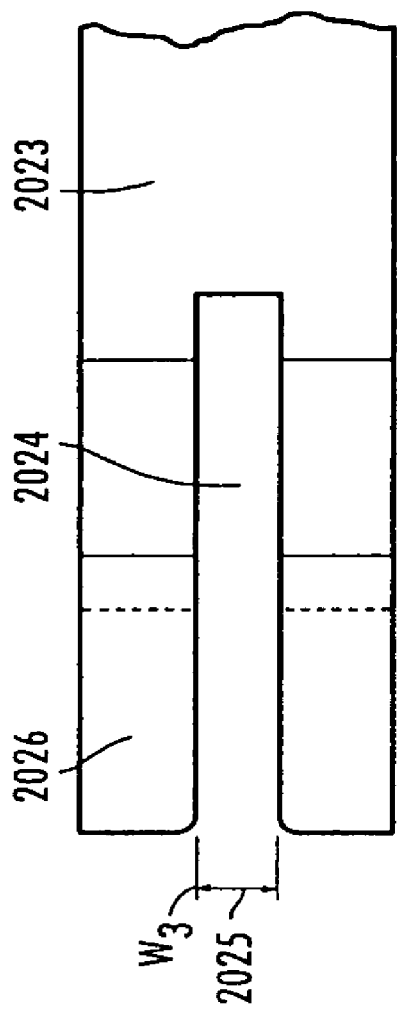
FIG. 107A is a close-up view drawing of the retrieval tip of the instrument of FIG. 106.
Figure 107B:
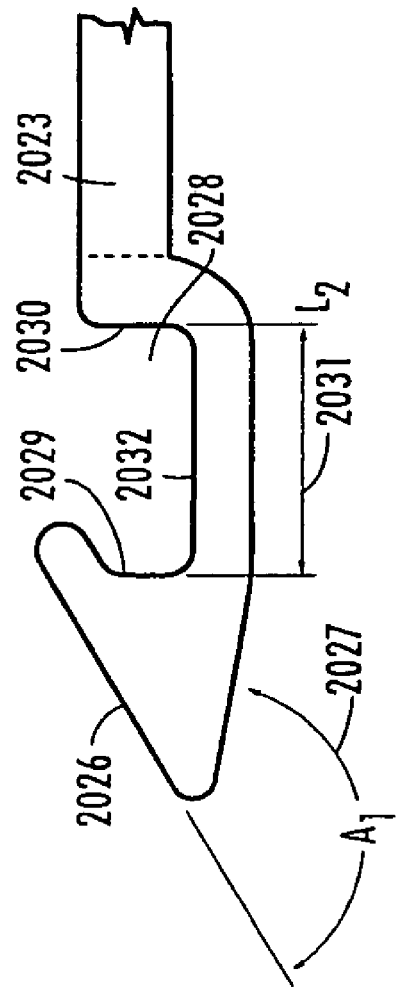
FIG. 107B is a different view of the retrieval tip.
Figure 107C:
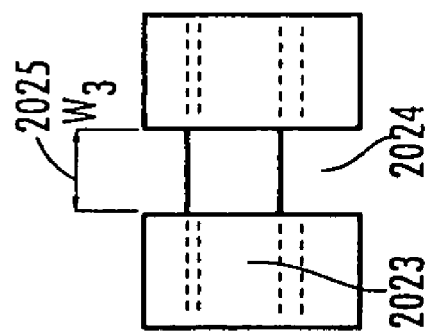
FIG. 107C is an end-on view of the retrieval tip.

Referring to FIG. 106, retrieval instrument 2020 has a proximal portion 2021 formed to a handle shape and an elongated distal portion 2022 terminating in distal tip 2023. Referring to FIGS. 107A through 107C, distal tip 2023 has a slot 2024 of width $W_3$ (2025) which is slightly larger than width $W_2$ (2006 in FIG. 105A) but less than $W_1$ (2004). The profile of distal end 2023 has a distal surface 2026 inclined at an angle $A_1$ (2027) and a capture region 2028 bounded on its distal end by hook-shaped surface 2029 and on its proximal end by lateral surface 2030 displaced from surface 2029 a distance $L_2$ (2031) and surface 2032.

Figure 108:
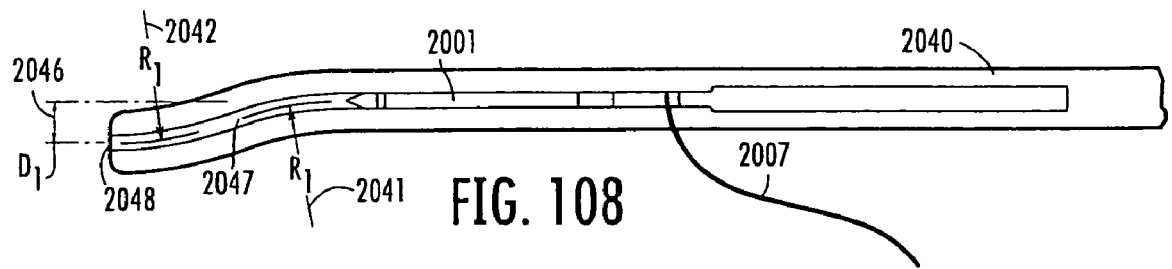
FIG. 108 shows a distal portion of an insertion instrument.

FIG. 108 shows the distal portion 2040 of an insertion instrument of this embodiment. Needle 2001 is positioned in the forming channel 2047 and suture 2007 is affixed to the needle. Distal portion 2040 has two radii, $R_1$ (2041) and $R_2$ (2042) which together displace forming channel 2045 a distance $D_1$ (2046). Radius $R_2$ (2042) forms the needle to a radial shape having a radius $R_3$ (2049 in FIG. 109C) slightly larger than $R_2$ (2042). A normal to distal-most surface 2048 is coaxial with the axis of the axis of portion 2040.

Figure 109A:
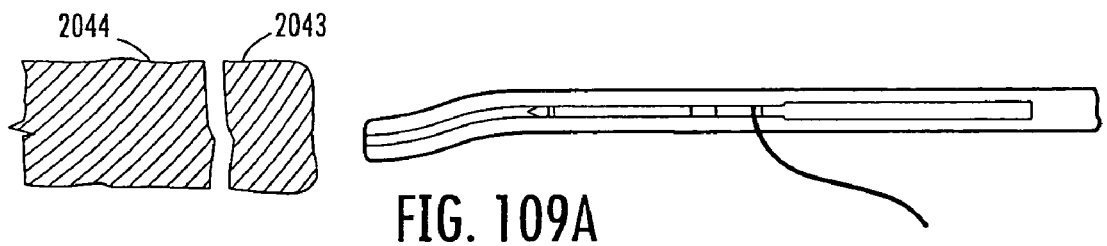
FIGS. 109A through 109K show the way in which the needle of FIG. 105, insertion of FIG. 108 and retrieval instrument of FIGS. 106 and 109 are used.
Figure 109B:
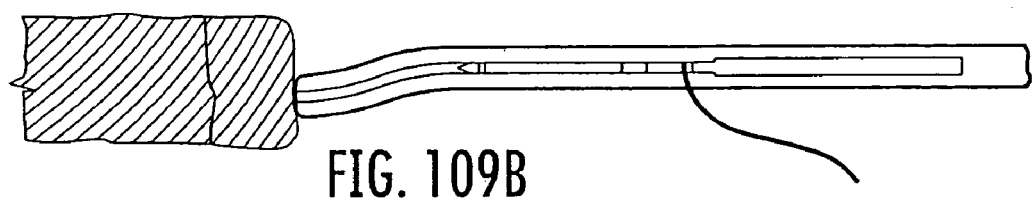
Figure 109C:
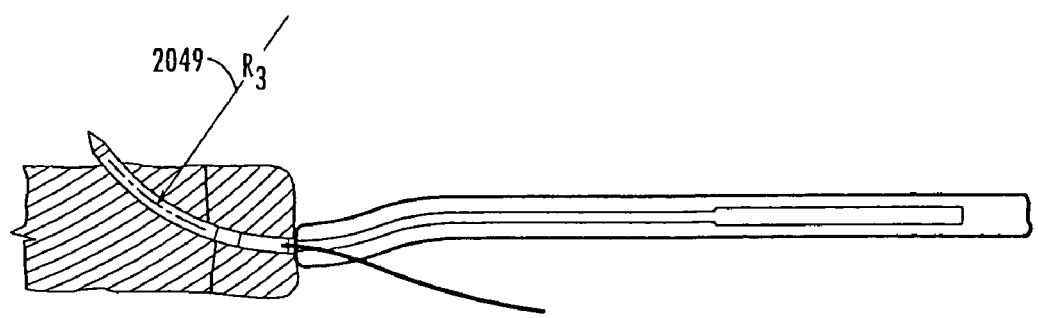
Figure 109D:
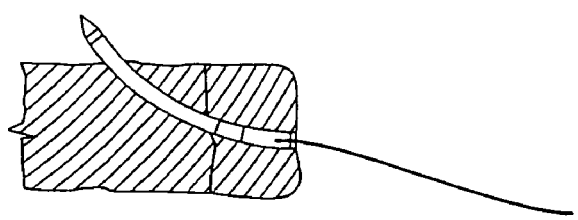
Figure 109E:
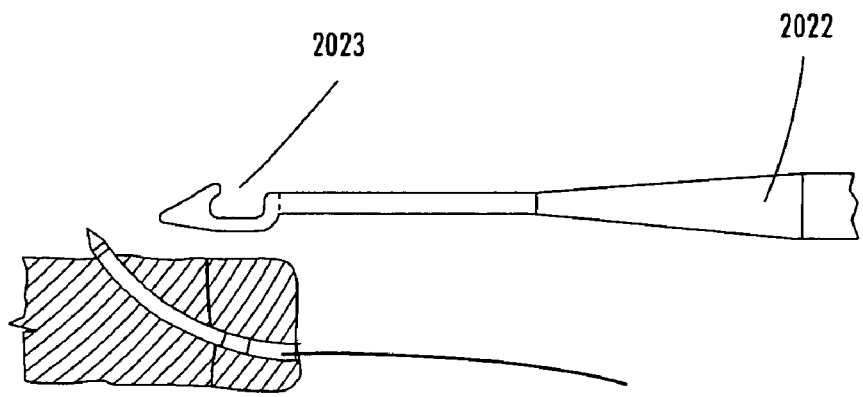
Figure 109F:
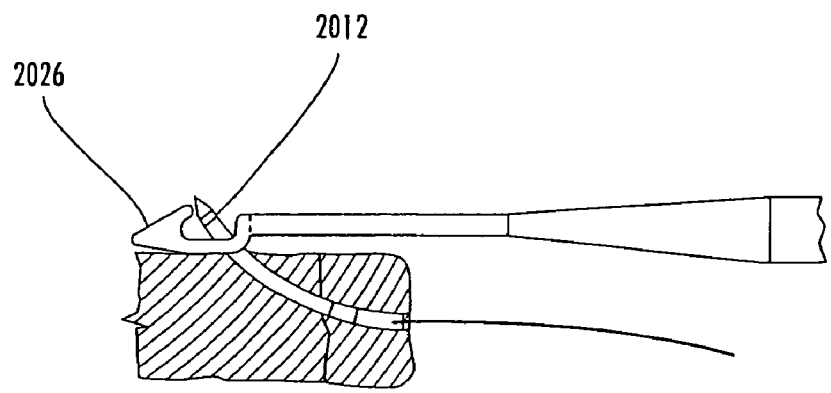

Referring to FIG. 109A, tissue 43 is to be sutured to tissue 2044. In FIG. 109B, the "tear" is closed by applying force to tissue 2043 using distal portion 2040. In FIG. 109C, needle 2001 has been inserted in the same manner as in the previous embodiment. In FIG. 109D, the insertion instrument has been removed and needle 2001 remains in place with suture 2007. In FIG. 109E, retrieval instrument 2020 has been brought into position. FIG. 109F, distal tip 2023 has been inserted such that needle 2001 is engaged in slot 2024 and surface 2026 (see FIG. 107B) acting on shoulders 2012 (FIG. 105A) of needle 2001 has displaced the needle distally in tissue 2043 and 2044.

Figure 109G:
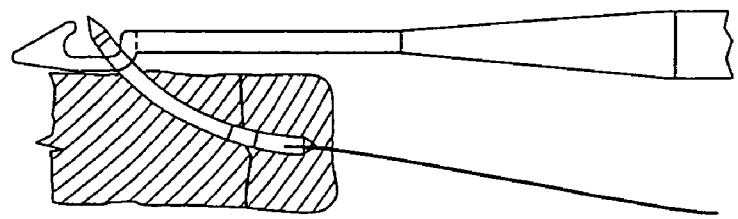
Figure 109H:
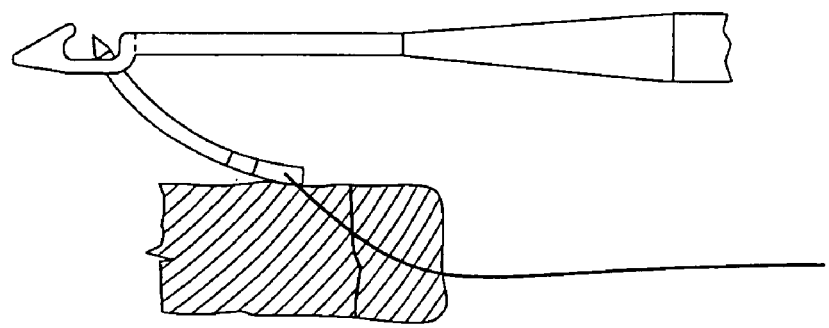
Figure 109I:
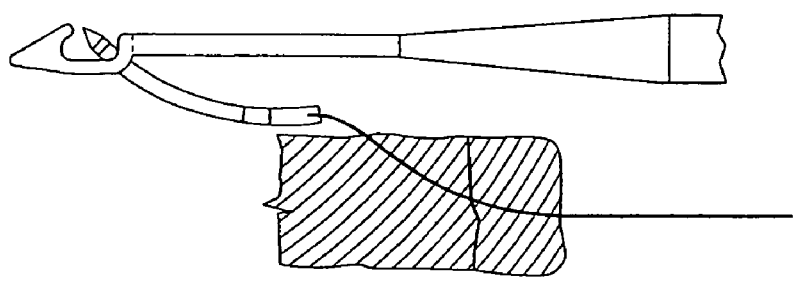
Figure 109J:
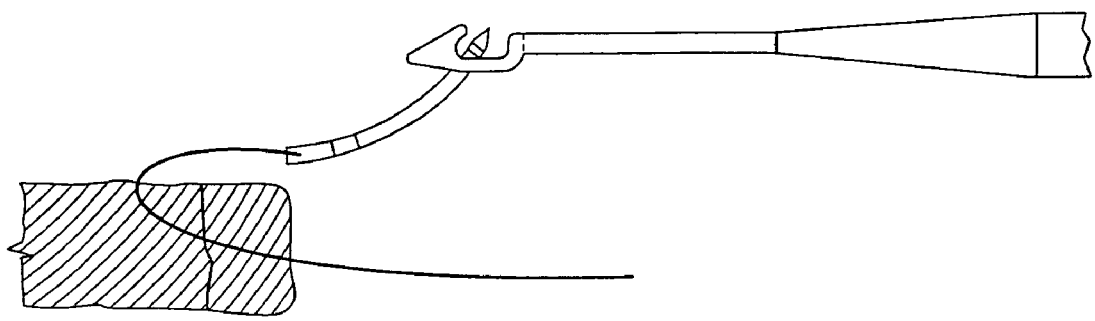
Figure 109K:
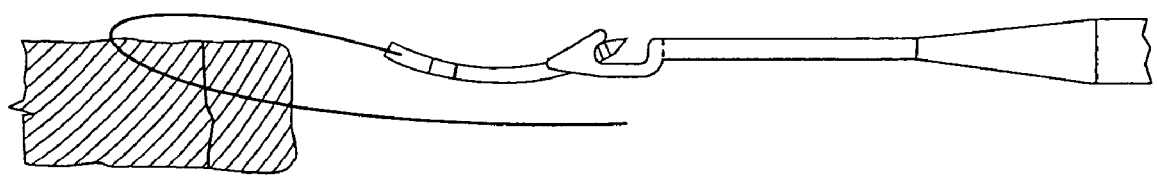

Referring to FIG. 109G, distal end 2002 of needle 2001 is captured in region 20028 (FIG. 107B). Displacing retrieval instrument 2020 distally (FIG. 109H) causes needle 2001 to be extracted from tissue 2043 thereby pulling suture 2007 through the tissue. In FIG. 109I additional suture has been pulled through the tissue. In FIG. 109J, retrieval instrument 2020 has been moved proximally causing needle 2001 to pivot in distal tip 2023. In FIG. 109K, needle 2001 has pivoted into position for retrieval through a cannula.

Although the illustrative embodiments of the present disclosure have been described herein with reference to the accompanying drawings and examples, it is to be understood that the disclosure is not limited to those precise embodiments, and various other changes and modifications may be affected therein by one skilled in the art without departing from the scope of spirit of the disclosure. All such changes and modifications are intended to be included within the scope of the disclosure as defined by the appended claims.

We claim:

1. A suture needle configured for use with a rigid cannula defined by a longitudinal axis and including a non-linear passageway characterized by a radial portion that terminates in an off-axis distal end, the needle comprising:
a length of inelastically malleable material linear along its entire length and having proximal and distal portions, wherein said proximal portion includes a proximal end and at least one lateral surface spaced a distance from said proximal end for receiving a suture and wherein said distal portion is characterized by a sharpened distal tip,
such that when the needle is pushed through the non-linear passageway of the cannula, the needle inelastically deforms in accordance with the radial portion and off-axis distal end to form a curved needle that remains curved after being pushed out of the cannula passageway.

2. The suture needle as set forth in claim 1, wherein the needle includes one or more flat sides that prevent rotation of the needle as it passes through the radial portion and off-axis distal end of the cannula.

3. The suture needle as set forth in claim 2, wherein the needle includes opposing flat sides.

4. The suture needle as set forth in claim 1, wherein the needle includes one or more indented portions that assist with the deformation of the needle as it passes through the radial portion and off-axis distal end of the cannula.

5. The suture needle as set forth in claim 1, wherein the sharpened distal tip of the needle includes a feature to facilitate grasping by a separate instrument.

6. The suture needle as set forth in claim 1, wherein the needle is 15 mm or less.

7. The suture needle as set forth in claim 1, wherein the needle is 10 to 13 mm in length.

8. The suture needle as set forth in claim 1, wherein the needle has a non-circular cross-section.

9. The suture needle as set forth in claim 1, wherein the needle has a substantially rectangular cross-section and includes at least two parallel sides.

10. The suture needle as set forth in claim 1, wherein the cross-section of said needle is non-uniform along its length.

11. A suture punch system capable of directly passing a suture into a tissue of interest, said system comprising:
a rigid cannula defined by a longitudinal axis and including a non-linear passageway characterized by a radial portion that terminates in an off-axis distal end; and
a needle comprising a length of inelastically malleable material that is linear along its entire length, said needle having proximal and distal portions, wherein said proximal portion includes a proximal end and at least one lateral surface spaced a distance from said proximal end for receiving a suture and wherein said distal portion is characterized by a sharpened distal tip,
such that when the needle is pushed through the non-linear passageway of the cannula, the needle inelastically deforms in accordance with the radial portion and off-axis distal end to form a curved needle that remains curved after being pushed out of the cannula passageway.

12. The system of claim 11, further comprising a braided suture attached to said needle at said at least one lateral surface.

13. A curved suture needle for delivering a suture to a tissue of interest, said needle fabricated by the process of:
providing a length of inelastically malleable material that is linear along its entire length, said material having proximal and distal portions, wherein said proximal portion includes a proximal end and at least one lateral surface spaced a distance from said proximal end for receiving a suture and said distal portion is characterized by a sharpened distal tip;
introducing said linear length of inelastically malleable material into a non-linear passageway of a rigid cannula defined by a longitudinal axis, wherein said passageway is characterized by radial portion that terminates an off-axis distal end,
pushing said linear material through said radial portion and off-axis distal end so as to inelastically deform said material into a curved needle that remains curved after being pushed out of the cannula passageway.

* * * * *